(12) United States Patent
Banville et al.

(10) Patent No.: US 6,924,391 B2
(45) Date of Patent: Aug. 2, 2005

(54) ALPHA-AMINO,-THIO,-OXO SUBSTITUTED KETONES AS PHOSPHOLIPASE INHIBITORS

(75) Inventors: Jacques Banville, St-Hubert (CA); Roger Remillard, Napierville (CA); Neelakantan Balasubramanian, Madison, CT (US); Gilles Bouthillier, Canton de Granby (CA); Alain Martel, Delson (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 440 days.

(21) Appl. No.: 09/848,694

(22) Filed: May 3, 2001

(65) Prior Publication Data

US 2002/0037875 A1 Mar. 28, 2002

Related U.S. Application Data

(60) Provisional application No. 60/203,741, filed on May 11, 2000.

(51) Int. Cl.[7] ..................... C07C 229/38; A61K 31/195
(52) U.S. Cl. ..................... 562/441; 562/464; 514/567; 514/529; 514/532; 514/648; 514/620; 514/665; 514/666; 560/36; 560/129; 564/164; 564/165; 564/305; 564/337; 568/27; 568/28; 568/30; 568/41; 568/42
(58) Field of Search ..................... 514/567, 529, 514/532, 648, 620, 665, 666; 562/441, 464; 560/36, 129; 564/164, 165, 305, 337; 568/27, 28, 30, 41, 42

(56) References Cited

U.S. PATENT DOCUMENTS

| | | | |
|---|---|---|---|
| 5,453,443 A | 9/1995 | Perrier et al. | |
| 5,478,857 A | 12/1995 | Clemens et al. | |
| 5,866,318 A | 2/1999 | Rydel et al. | |

FOREIGN PATENT DOCUMENTS

| | | | |
|---|---|---|---|
| JP | 5-222006 | * | 8/1993 |
| JP | 09268153 A | | 4/1996 |
| WO | WO 97/21676 | | 6/1997 |
| WO | WO 98/08818 | | 3/1998 |
| WO | WO 98/25893 | | 6/1998 |
| WO | WO 99/15129 | | 4/1999 |
| WO | 0009114 | * | 2/2000 |

OTHER PUBLICATIONS

I. P. Street, et al, "Slow– and Tight–Binding Inhibitors of the 85–kDa Human Phospholipase $A_2$," BIOCHEMISTRY, 32, pp. 5935–5940, 1993.

K. M. Abdullah, et al, "Synthesis and Preparation of an Affinity Chromatography Column for the Purification of Cytosolic Phospholipase $A_2$," Bioorganic & Medicinal Chemistry Letters, 5(5), pp. 519–522, 1995.

D. L. Boger, et al, "Trifluoromethyl Ketone Inhibitors of Fatty Acid Amide Hydrolase: A Probe of Structural and Conformational Features Contributing to Inhibition," Bioorganic & Medicinal Chemistry Letters, 9, pp. 265–270, 1999.

P. Norman, "Medicinal Chemistry in Eastern England–Ninth Symposium," IDRUGS, 1(1), pp. 49–54, 1998.

L. A. Clemens, et al, "Reactive Glia Express Cytosolic Phospholipase A2 After Transient Global orebrain Ischemia in the Rat," STROKE, 27(3), pp. 527–535, 1996.

D. T. Stephenson, et al, "Cytosolic Phospholipase A2 (cPLA2) Immunoreactivity is Elevated in Alzheimer's Disease Brain," Neurobiology of Disease, 3, pp. 51–63, 1996.

Z. Huang, et al, "Methyl Arachidonyl Fluorophosphonate, a Potent Irreversible cPLA2 Inhibitor, Blocks the Mobilization of Arachidonic Acid in Human Platelets and Neutrophils," Mediators of Inflammation, 3, pp. 307–308, 1994.

A. Gresham, et al, "Increased Synthesis of High–Molecular – Weight cPLA2 Mediates Early UV–Induced PGE2 in Human Skin," American Journal of Physiology, 270, pp. C1037–C1050, 1996.

J. Balsinde, et al, "Distinct Roles in Signal Transduction for Each of the Phospholipase A2 Enzymes Present in P388D1 Macrophages," Journal of Biological Chemistry, 271(12), pp. 6758–6765, 1996.

* cited by examiner

Primary Examiner—Shailendra Kumar
(74) Attorney, Agent, or Firm—Pamela A. Mingo

(57) ABSTRACT

Inhibitors of the cytosolic phospholypase A2 enzymes are provided which are of use in controlling a wide variety of inflammatory diseases. The inhibitors of the present invention have the general formula

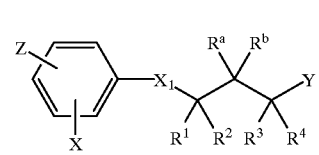

I wherein X, Z, $X_1$, $R^1$, $R^2$, $R^a$, $R^b$, $R^3$, $R^4$ and Y are as defined in the specification.

2 Claims, No Drawings

ALPHA-AMINO,-THIO,-OXO SUBSTITUTED KETONES AS PHOSPHOLIPASE INHIBITORS

CROSS-REFERENCE TO RELATED APPLICATION

This application claims the benefit of U.S. Provisional Application Ser. No. 60/203,741 filed May 11, 2000.

BACKGROUND OF THE INVENTION

1. Field of the Invention

The present invention relates to certain alpha amino, thio, oxo substituted ketone compounds, their salts, hydrates and derivatives thereof, a process for their preparation, intermediates useful in their preparation, and pharmaceutical compositions containing them. Such ketone compounds are inhibitors of phospholipase A2 enzymes that are involved in the human inflammatory diseases and are thus useful agents in the treatment of inflammatory diseases such as asthma, arthritis, inflammatory bowel disease, and neurodegenerative diseases.

2. Background of the Invention and Description of the Prior Art

Inflammatory diseases of the skin, such as psoriasis and atopic dermatitis, afflict greater than 5% of the population. Inflammatory diseases such as asthma affect more than 10 million people in U.S. alone. Currently the treatment of these disorders typically involves the topical and inhalation use of coricosteroids and broncodilators. However, these agents also have undesirable side effects such as skin atrophy which limit the duration of therapy. In addition, topical application of a drug is difficult for many patients where the affected area may be very large.

Phospholipase $A_2$ ($PLA_2$) is the common name for phosphatide 2-acylhydrolase which catalyzes the hydrolysis of the sn-2-acyl ester bond of phosphoglycerides and results in production of lysophospholipids and free fatty acids. When the fatty acid is arachidonic acid, further action by cyclooxygenase and 5-lipoxygenase enzymes results in eicosanoid production, which is implicated in inflammation and leukotrienes which are linked to asthma. Lysophophospholipid metabolism results in production of platelet activating factor and both lysophospholipids and platelet activating factor play a role in inflammation.

$PLA_2$ enzymes exist as secreted forms (MW~12,000–15,000) and cytosolic forms (MW~85,000). The cytosolic or $cPLA_2$ enzymes appear to play a key role in the pathway leading to the formation of platelet activating factor and the eicosanoids.

Inappropriate activation of the cytosolic $PLA_2$ enzymes, therefore, can result in a variety of chronic and acute conditions including asthma, cerebral ischemia (Clemens et al, *Stroke,* 1996, 27, 527–535), Alzheimer's Disease (Stephenson et al, *Neurobiology of Stroke,* 1996, 3, 51–63 and see also U.S. Pat. No. 5,478,857), rheumatoid arthritis, neutrophil and platelet activation (Huang et al, *Mediators of Inflammation,* 1994, 3, 307–308), chronic skin inflammation and damage to the skin resulting from exposure to ultraviolet light (Gresham, et al., *American Journal of Physiology,* 1996, 270; *Cell Physiology* 39:C1037–C1050) and macrophage activation (Balsinde, et al., *Journal of Biological Chemistry,* 1996, 271, 6758–6765).

Inhibitors of the $cPLA_2$ enzymes may, therefore, be of use in controlling a wide variety of inflammatory diseases. The literature describes a significant number of compounds said to be phospholipase $A_2$ inhibitors.

*Biochemistry* (1993) 32: 5935–5940, discloses a trifluoromethyl ketone analog of arachidonic acid having the formula

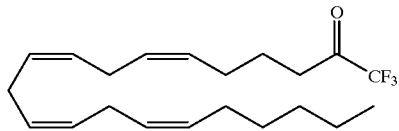

as a selective inhibitor of $cPLA_2$.

*Bioorganic Med. Chem. Lett.* (1995) 5: 519–522, discloses selective $cPLA_2$ inhibitors of the formula

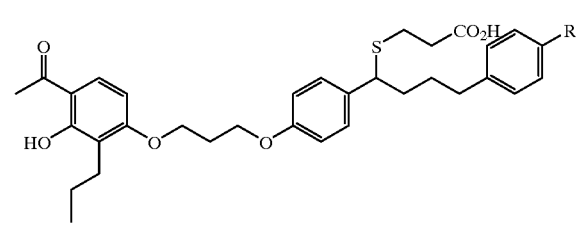

where R is either H or OH.

Japanese published Patent Application JP09268153A (Derwent No. 97-554679/51) discloses $cPLA_2$ inhibitors of the formula $RCOCF_3$ where RCO is an acyl residue of an n-3 series highly unsaturated fatty acid. The compounds are said to be useful as antiinflammatory or anti-allergic drugs.

Certain trifluoromethylketone have been disclosed as inhibitors of fatty acid amide hydrolase in *Bioorg. & Med. Chem. Lett.* (1999) 9, 265–270.

Published PCT Application WO 98/25893 discloses arylsulfonamide compounds of the general formula

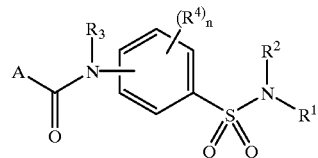

wherein

A represents a $C_4$–$C_{10}$ alkyl group, an aryl group, an arylalkyl group, radicals selected from the group consisting of —CH=CH—B, —O—B, —S—B, and —NH—B, or radicals of formula —CH$_2$—X, wherein B represents a non-aromatic $C_3$–$C_8$ carbocycle, a $C_3$–$C_8$ alkyl group, a heterocycle or an arylalkyl group, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group, and X is a member selected from the group consisting of a halogen atom, —S-aryl, —S-heterocycle, and —PO$_3$R$_2$ wherein each R is independently selected from the group consisting of a hydrogen atom and $C_1$–$C_3$ alkyl;

$R^1$ and $R^2$ each independently represent a hydrogen atom, a lower alkyl group, or a group represented by the formula: —(CH$_2$)$_q$—A' wherein q is an integer of 2 to 4, and A' is a member selected from the group consisting of a hydroxyl group, a group represented by the formula:

wherein $R^5$ and $R^6$ each independently represent a hydrogen atom, a lower alkyl group, or a group represented by the formula:

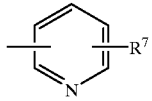

wherein $R^7$ represents a hydrogen atom, a lower alkyl group, or a group represented by the formula:

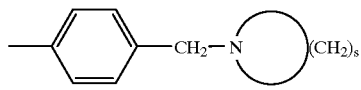

wherein s is an integer of 2 to 5; or
$R^1$ and $R^2$ each independently represent an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

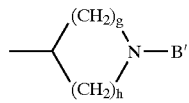

wherein g and h are each an integer of 1 to 4, and B' stands for a lower alkyl group, an arylalkyl group, an arylalkyl group substituted by lower alkyl; halogen or a lower alkoxy group, or a pyridylalkyl group, or a pyridylalkyl group substituted with a lower alkyl group, a halogen or a lower alkoxy group; or
$R^1$ and $R^2$ may be combined together to form a 6- or 7-membered ring which may contain a nitrogen or oxygen atom in addition to the nitrogen atom to which $R^1$ and $R^2$ are bonded, and said 6- or 7-membered ring may be substituted with a lower alkyl, arylalkyl, cycloalkylalkyl or heteroarylalkyl group;
$R^3$ represents a hydrogen atom, a lower alkyl group, or a $C_3$–$C_8$ cycloalkyl group;
$R^4$ represents a hydrogen atom, a lower alkyl group, a lower alkoxy group or a halogen atom;
n is an integer of 1 to 4, provided that when n is 2, the two $R^4$ groups may form a cyclohexenyl or phenyl ring together with two adjacent carbon atoms constituting the benzene ring; and any pharmacologically acceptable salts thereof as inhibitors of phospholipase $A_2$ activity, particularly $cPLA_2$.

The published PCT Application WO 98/08818 discloses Inhibitors of phospholipase enzymes of formulae I, II and III.

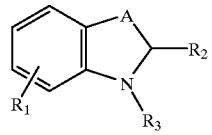

I

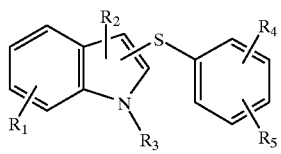

II

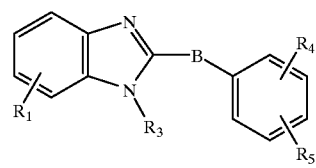

III or a pharmaceutically acceptable salt thereof, wherein:
A is independent of any other group and is selected from the group consisting of —$CH_2$— and —$CH_2$—$CH_2$—;
B is independent of any other group and is selected from the group consisting of —$(CH_2)_n$—, —$(CH_2O)_n$—, —$(CH_2S)_n$—, —$(OCH_2)_n$—, —$(SCH_2)_n$—, —$(CH=CH)_n$—, —$(C\equiv C)_n$—, —$CON(R_6)$—, —$N(R_6)CO$—, —O—, —S— and —$N(R_6)$—;
$R_1$ is independent of any other R group and is selected from the group consisting of —X—$R_6$, —H, —OH—, halogen, —CN, —$NO_2$, $C_1$–$C_5$ alkyl, alkenyl, alkynyl, aryl and substituted aryl;
$R_2$ is independent of any other R group and is selected from the group consisting of —H, —COOH, —$COR_5$, —$CONR_5R_6$, —$(CH_2)_n$—W—$(CH_2)_m$—Z—$R_5$, —$(CH_2)_n$—W—$R_5$, —Z—$R_5$, $C_1$–$C_{10}$ alkyl, alkenyl and substituted aryl;
$R_3$ is independent of any other R group and is selected from the group consisting of —H, —COOH, —$COR_5$, —CON $R_5R_6$, —$(CH_2)_n$—W—$(CH_2)_m$—Z—$R_5$, —$(CH_2)_n$—W—$R_5$, —Z—$R_5$, $C_1$–$C_{10}$ alkyl, alkenyl and substituted aryl;
$R_4$ is independent of any other R group and is selected from the group consisting of —H, —OH, $OR_6$, $SR_6$, CN, —$COR_6$, —$NHR_6$, —COOH, —$CONR_6R_7$, —$NO_2$, —$CONHSO_2R_8$, $C_1$–$C_5$ alkyl, alkenyl and substituted aryl;
$R_5$ is independent of any other R group and is selected from the group consisting of —H, —OH, —$O(CH_2)_n$ $R_6$, —$SR_6$, —CN, —$COR_6$, —$NHR_6$, —COOH, —$NO_2$, —COOH, —$CONR_6R_7$, —$CONHSO_2R_8$, $C_1$–$C_5$ alkyl, alkenyl, alkynyl, aryl, substituted aryl, —$CF_3$, —$CF_2CF_3$ and

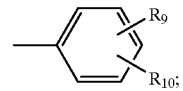

$R_6$ is independent of any other R group and is selected from the group consisting of —H, $C_1$–$C_5$ alkyl, alkenyl, alkynyl, aryl and substituted aryl;

R$_7$ is independent of any other R group and is selected from the group consisting of —H, C$_1$–C$_5$ alkyl, alkenyl, alkynyl, aryl and substituted aryl;

R$_8$ is independent of any other R group and is selected from the group consisting of C$_1$–C$_3$ alkyl, aryl and substituted aryl;

R$_9$ is independent of any other R group and is selected from the group consisting of —H, —OH, a halogen, —CN, —OR$_6$, —COOH, —CONR$_6$R$_7$, tetrazole, —CONHSO$_2$R$_8$, —COR$_6$, —(CH$_2$)$_n$CH(OH)R$_6$ and —(CH$_2$)$_n$CHR$_6$R$_5$;

R$_{10}$ is independent of any other R group and is selected from the group consisting of —H, —OH, a halogen, —CN, —OR$_6$, —COOH, —CONR$_6$R$_7$, tetrazole, —CONHSO$_2$R$_8$, —COR$_6$, —(CH$_2$)$_n$CH(OH)R$_6$ and —(CH$_2$)$_n$CHR$_6$R$_5$;

W is, independent each time used including within the same compound, selected from the group consisting of —O—, —S—, —CH$_2$—, —CH=CH—, —C≡C— and —N(R$_6$)—;

X is independent of any other group and is, independently each time used including within the same compound, selected from the group consisting of —O—, —S— and —N(R$_6$)—;

Z is independent of any other group and is, independently each time used including within the same compound, selected from the group consisting of —CH$_2$—, —O—, —S—, —N(R$_6$)—, —CO—, —CON(R$_6$)— and —N(R$_6$)CO—;

m is, independently each time used including within the same compound, an integer from 0 to 4; and n is independently of m and is, independently each time used including within the same compound, an integer from 0 to 4.

*Drugs* 1998, Vol. 1, No. 1, pp. 49–50 discloses a limited series of cPLA$_2$ inhibitors as shown below

| R$_1$ | R$_2$ | X |
|---|---|---|
| CH$_3$ | CH$_3$(CH$_2$)$_9$— | O |
| (1) | CH$_3$(CH$_2$)$_9$— | O |
| (1) | Ph(CH$_2$)$_5$ | S |
| (1) | CH$_3$(CH$_2$)$_9$— | SO$_2$ |

U.S. Pat. No. 5,866,318 relates to methods for inhibiting cell death in mammalian cells, particularly in neuronal cells, by administering a suitable inhibitor of phospholipase A$_2$ activity, typically an inhibitor of cPLA$_2$.

WO 97/21676 Patent discloses certain azetidinone compounds as phospholipase inhibitors in the treatment of atherosclerosis.

U.S. Pat. No. 5,453,443 discloses a series of biaryl ketones which are reported to inhibit PLA$_2$ enzymes. These compounds have the generic formula wherein:

R$^1$ is selected from
(a) hydrogen,
(b) —C$_{1-6}$ alkyl, and
(c) —C$_{1-6}$ alkyl-phenyl;

or wherein R$^1$ and R$^5$ are joined such that together with the carbon atoms to which they are attached there is formed a saturated or unsaturated carbon ring of 3, 4, 5, 6, 7 or 8 atoms;

R$^2$ and R$^3$ are each independently selected from
(a) hydrogen,
(b) —C$_{1-6}$ alkyl, and
(c) —C$_{1-6}$ alkyl-phenyl;

or wherein two R$^2$ or two R$^3$ are joined such that together with the carbon atoms to which they are attached there is formed a saturated or unsaturated carbon ring of 3, 4, 5, 6, 7 or 8 atoms;

R$^5$ is as defined above or is selected from
(a) hydrogen
(b) —C$_{1-6}$ alkyl,
(c) —C$_{1-6}$ alkyl-phenyl C$_{1-6}$ alkyl,
(d) —OH,
(e) —O—C$_{1-6}$ alkyl, or
(f) —C$_{1-6}$ alkyl-phenyl C$_{1-6}$ alkyl;

R$^6$ is selected from
(a) hydrogen
(b) —C$_{1-6}$ alkyl, and
(c) —C$_{1-6}$ alkyl-phenyl, wherein the phenyl is optionally substituted with C$_{1-2}$ alkyl;
(d) —OH,
(e) —O—C$_{1-6}$ alkyl, or
(f) —O—C$_{1-6}$ alkyl-phenyl, wherein the phenyl is optionally substituted with C$_{1-2}$ alkyl;

or wherein two R$^6$ are joined to form O= or are joined together such that together with the carbon atom to which they are attached there is formed a saturated or unsaturated carbon ring of 3, 4, 5, 6, 7 or 8 atoms;

R$^8$, R$^9$ and R$^{14}$ are each independently selected from
(a) H,
(b) —C$_{1-6}$ alkyl,
(c) halo
(d) —CN,
(e) —OH,
(f) —OC$_{1-6}$ alkyl,
(g) —OC$_{1-6}$ alkyl-phenyl,
(h) —SR$^{11}$,
(i) S(O)R$^{11}$, or
(j) S(O)$_2$R$^{11}$;

R$^{10}$, R$^{15}$, R$^{16}$ and R$^{17}$ are each independently selected from
(a) hydrogen,
(b) —C$_{1-6}$ alkyl, and
(c) —C$_{1-6}$ alkyl-phenyl;

R$^{11}$ is selected from
(a) —C$_{1-6}$ alkyl,
(b) —C$_{2-6}$ alkenyl, (c) —CF$_3$,
(d) -phenyl(R$^{12}$)$_2$, or
(e) —C$_{2-6}$ alkenyl-phenyl(R$^{12}$)$_2$, R$^{12}$ is
(a) hydrogen,
(b) —C$_{1-6}$ alkyl,
(c) Cl, F, I or Br;

R$^{13}$ is perfluoroC$_{1-6}$alkyl;

A and B are each independently
(a) covalent bond,
(b) O,
(c) S,
(d) S(O), or
(e) S(O)$_2$;

Q is selected from
(a) —CH(OH)R$^{13}$,
(b) —COR$^{13}$,
(c) —COR$^{16}$, or
(d) —C$_{1-6}$ alkylCOCOOR$^{17}$;

X$^1$ is selected from
(a) —O—,
(b) —S—,
(c) —S(O)—,
(d)

Z is
(a) H, or
(b) -phenyl-(R$^{14}$)$_3$, m is 0, 1, 2, 3 or 4;
n is 2, 3, 4, 5, 6 or 7; and
r and s are each independently 0, 1, 2, 3, 4, 5, 6, 7 or 8.

Published application WO 99/15129 discloses selective cPLA$_2$ inhibitors having the formula

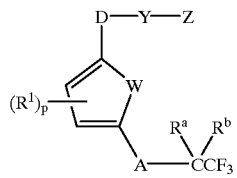

wherein W is CH=CH, CH=N, O or S;
R$^1$ is (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkylthio, halo, hydroxy, cyano,

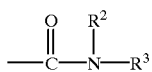

in which R$^2$ and R$^3$ are each independently hydrogen or (C$_1$-C$_6$)alkyl, —COO—(C$_1$-C$_6$)alkyl, CF$_3$, (C$_1$-C$_6$) alkylphenyl, phenyl or phenyl substituted by one or more, preferably 1–3, of (C$_1$-C$_6$)alkyl, —COO—(C$_1$-C$_6$)alkyl,

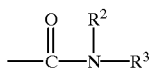

in which R$^2$ and R$^3$ are as defined above, halo, hydroxy, —O—(C$_1$-C$_6$)alkyl, —S—(C$_1$-C$_6$)alkyl or (C$_2$-C$_6$) alkenyl;
p is 0, 1 or 2;

A is V—(R$^c$)$_n$—;
R$^c$ is a straight or branched chain alkyl group;
n is 0 or an integer of from 1 to 6;
R$^a$ and R$^b$ when taken together form an oxo (=O) group, or R$^a$ and R$^b$ are each independently hydrogen or OH;
V is O, —S—, —SO—, —SO$_2$, —CONH or NHCO when n is an integer of from 1 to 6 or V is (C$_2$-C$_6$) alkenyl or a bond when n is 0 or an integer of from 1 to 6;
D is —(CH$_2$)$_m$ or a bond linking the

ring to Y;
m is an integer of from 1 to 6;
Y is —O—, —S—, —SO—, —SO$_2$;

or a bond;
R$^4$ is as defined below for R$^7$;
Z is

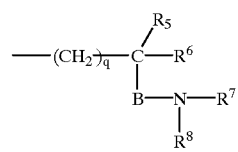

(a)

in which B is:

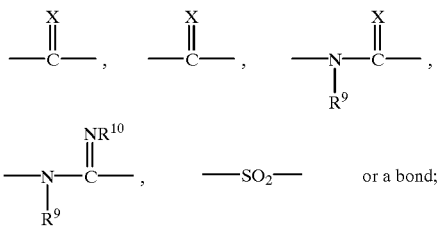

X is S or O;
q is an integer from 1 to 6;
R$^9$ is hydrogen or (C$_1$-C$_6$)alkyl;
R$^{10}$ is hydrogen, CN, NO$_2$, OH, —O—(C$_1$-C$_6$)alkyl, (C$_1$-C$_6$) alkyl, phenyl or (C$_1$-C$_6$)alkylphenyl;
R$^5$ and R$^6$ are each independently hydrogen or (C$_1$-C$_{18}$) alkyl;
R$^7$ and R$^8$ are each independently
(a) hydrogen;
(b) (C$_1$-C$_{18}$)alkyl;
(c) (C$_1$-C$_{18}$)alkyl substituted by one or more of
(1) phenyl;
(2) phenyl substituted by 1–5 fluoro, 1–3 (for each of the following phenyl substituents) halo (other than fluoro), 1–3 (C$_1$-C$_6$)alkoxy, 1–3(C$_1$-C$_6$)alkyl, nitro, cyano, hydroxy, trifluoromethyl, (C$_1$–C$_6$) alkylthio, amino, 1–3 (C$_1$–C$_6$) alkylamino, di(C$_1$–C$_6$)alkylamino, —CO$_2$H, —COO—(C$_1$–C$_6$)alkyl, —SO$_3$H, —SO$_2$NHR$^{15}$ in which R$^{15}$ is hydrogen or (C$_{1-6}$)alkyl, or

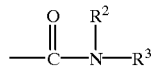

in which R$^2$ and R$^3$ are as defined above;
(3) heterocyclic selected from oxadiazolyl, isoxazolyl, oxazolyl, furyl and thiazolyl;
(4) heterocyclic substituted by one or more of, preferably 1–3, phenyl, phenyl substituted by 1–3 (for each of the following) halo, (C$_1$–C$_6$)alkoxy, (C$_1$–C$_6$)alkyl, nitro, cyano, hydroxy, trifluoromethyl, (C$_{1-6}$)alkylthio, amino, (C$_1$–C$_6$) alkylamino, di(C$_1$–C$_6$)alkylamino, CO$_2$H, —OO—(C$_1$–C$_6$)alkyl, —SO$_3$H, SO$_2$NHR$^{15}$ in which R$^{15}$ is hydrogen or (C$_1$–C$_6$)alkyl, or

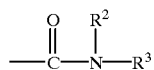

in which R$^2$ and R$^3$ are as defined above, (C$_1$–C$_6$) alkyl or (C$_1$–C$_6$)alkyl substituted by one or more, preferably 1–3, phenyl or heterocyclic groups, said phenyl or heterocyclic group being unsubstituted or substituted by 1–3 (for each of the following) halo, 1–3 (C$_1$–C$_6$)alkoxy, 1–3 (C$_1$–C$_6$) alkyl, nitro, cyano, hydroxy, trifluoromethyl, (C$_1$–C$_6$)alkylthio, amino, 1–3 (C$_1$–C$_6$)alkylamino, di(C$_1$–C$_6$)alkylamino, COOH, —COO—(C$_1$–C$_6$) alkyl, —SO$_3$H, —SO$_2$NHR$^{15}$ in which R$^{15}$ is hydrogen or (C$_1$–C$_6$)alkyl, or

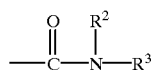

in which R$^2$ and R$^3$ are each independently hydrogen or (C$_1$–C$_6$)alkyl, the heterocyclic radical being selected from imidazolyl, oxadiazolyl, isoxazolyl, pyrrolyl, pyrazolyl, oxazolyl, furyl, thianyl or thiazolyl;
(5) carboxy or —COO—(C$_1$–C$_6$)alkyl;
(6) hydroxy, halo, —O—(C$_1$–C$_6$) alkyl or —S—(C$_1$–C$_6$)alkyl, with the proviso that the OH, ethers or thioethers cannot be on the carbon bearing the heteroatoms;
(7) cyano;
(8) halo, trifluoromethyl or trifluoroacetyl;
(9) CH$_2$ L—R$^{16}$ in which L is

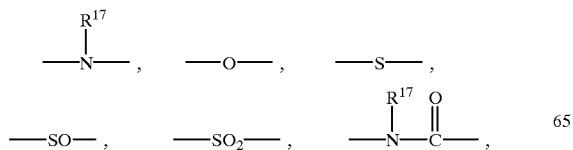

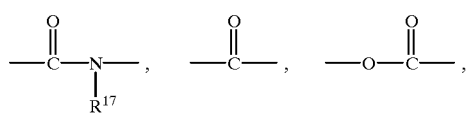

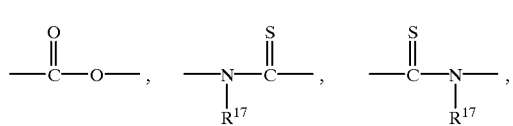

or —O—SiR$^{16}$R$^{18}$R$^{19}$ or a bond in which R$^{16}$ and R$^{17}$ are each independently (C$_1$–C$_{18}$)alkyl or (C$_2$–C$_{18}$)alkenyl or (C$_1$–C$_{18}$)alkyl or (C$_2$–C$_{18}$) alkenyl substituted by one or more, preferably 1–3, phenyl or heterocyclic radicals, said phenyl or heterocyclic radicals being unsubstituted or substituted by 1–5 fluoro, 1–3 halo (other than fluoro), 1–3 (C$_1$–C$_6$)alkoxy, 1–3(C$_1$–C$_6$)alkyl, nitro, cyano, hydroxy, 1–3 trifluoromethyl, 1–3 (C$_1$–C$_6$)alkylthio, amino, 1–3(C$_1$–C$_6$)alkylamino, 1–3 di(C$_1$–C$_6$)alkylamino, CO$_2$H, 1–3 —COO (C$_1$–C$_6$)alkyl,

or —SO$_2$NHR$^9$ in which R$^9$ is hydrogen or (C$_1$–C$_6$)alkyl and R$^2$ and R$^3$ are as defined above;

(b)

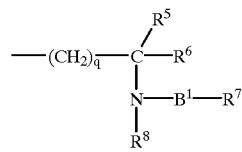

in which B$^1$ is

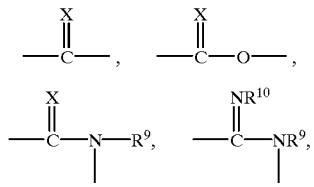

—SO$_2$—, —PO(OR$^9$)$_2$ or a bond; providing that when B$^1$ is —PO(OR$^9$)$_2$, then R$^7$ becomes R$^9$, and when B$^1$ is

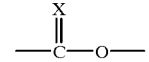

or —SO$_2$—, then R$^7$ cannot be hydrogen;

X, q, $R^5$, $R^6$, $R^7$, $R^8$, $R^9$ and $R^{10}$ are as defined in (a);

(c)
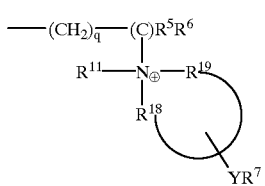

in which q, $R^5$ and $R^6$ are as defined above;

$R^{18}$, $R^{19}$ and $R^{11}$ are as defined above for $R^7$ and $R^8$ except that they may not be hydrogen, or $R^{18}$ and $R^{19}$ taken together with the nitrogen to which they are attached represent a 4, 5- or 6-membered heterocyclic ring and Y, $R^7$ and $R^{11}$ are as defined above, or $R^{18}$, $R^{19}$ and $R^{11}$ taken together with the nitrogen to which they are attached represent pyridinium, said pyridinium group being unsubstituted or substituted by $(C_1-C_{12})$ alkyl, $(C_1-C_{12})$alkoxy, amino, $(C_1-C_{12})$alkylamino, di$(C_1-C_{12})$alkylamino,

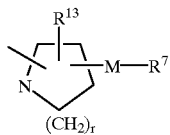

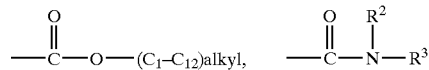

in which $R^2$ and $R^3$ are as defined above, phenyl or phenyl $(C_1-C_{10})$alkyl;

(d)
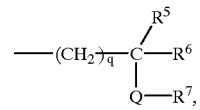

in which $R^{13}$ is $(C_1-C_{18})$alkyl or $(C_1-C_{18})$alkyl substituted by carboxy,

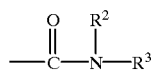

in which $R^2$ and $R^3$ are as defined above, hydroxy, —O—$(C_1-C_6)$ alkyl, —O—$(C_1-C_6)$ alkyl or —S—$(C_1-C_6)$ alkyl substituted by 1 or 2 phenyl or substituted phenyl groups, the substituents for the substituted phenyl groups being 1–5 fluoro or 1–3 (for each of the following phenyl substituents) halo (other than fluoro), $(C_1-C_6)$alkoxy, $(C_1-C_6)$alkyl, nitro, cyano, hydroxy, trifluoromethyl, $(C_1-C_6)$alkylthio, amino, $(C_1-C_6)$ alkylamino, di$(C_1-C_6)$ alkylamino, $CO_2H$, COO—$(C_1-C_6)$ alkyl, $SO_3H$, $SO_2NHR^{15}$ in which $R^{15}$ is hydrogen or $(C_1-C_6)$ alkyl or

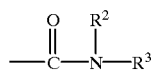

in which $R^2$ and $R^3$ are as defined above;

r is 0 or an integer of from 1 to 3;

$R^7$ is as defined above;

M is —$(CH_2—)_m$T where T is

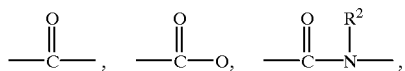

in which $R^2$ is as defined above, —$SO_2$— or a bond when $MR^7$ is on nitrogen and providing that when T is

or —SO— or —$SO_2$—, then $R^7$ cannot be hydrogen, and T is

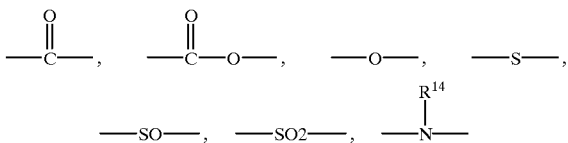

or a bond when $MR^7$ is on a carbon atom of the heterocyclic ring;

$R^{14}$ is hydrogen or $(C_1-C_6)$alkyl;

m is 0 or an integer of 1–6;

(e)
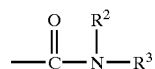

wherein Q is —O—, —S—, —SO— or —$SO_2$—, and q, $R^5$, $R^6$ and $R^7$ are as defined above, providing that when Q is —SO— or —$SO_2$—, $R^7$ cannot be hydrogen;

(f) $R^7$ wherein $R^7$ is defined above, providing that when Y is —SO— or —$SO_2$—, $R^7$ cannot be hydrogen; and $R^{18}$ and $R^{19}$ are phenyl or phenyl substituted by 1–3 halo, $(C_1-C_6)$alkoxy, $(C_1-C_6)$alkyl, nitro, cyano, hydroxy, trifluoromethyl, $(C_1-C_6)$alkylthio, amino, $(C_1-C_6)$ alkylamino, di$(C_1-C_6)$alkylamino, $CO_2H$, —COO—$(C_1-C_6)$alkyl, —$SO_3H$, $SO_2NHR^{15}$ in which $R^{15}$ is hydrogen or $(C_1-C_6)$alkyl, or

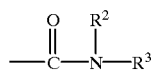

in which $R^2$ and $R^3$ are as defined above; or pharmaceutically acceptable salts, solvates or prodrugs thereof.

$R^{18}$ and $R^{19}$ are phenyl or phenyl substituted by 1–3 halo, $(C_1-C_6)$alkoxy, $(C_1-C_6)$ alkyl, nitro, cyano, hydroxy, trifluoromethyl, $(C_1-C_6)$ alkylthio, amino, $(C_1-C_6)$ alkylamino, di$(C_1-C_6)$alkylamino, $CO_2H$, —COO—$(C_1-C_6)$alkyl, —$SO_3H$, $SO_2NHR^{15}$ in which $R^{15}$ is hydrogen or $(C_1-C_6)$alkyl, or

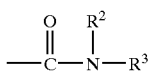

in which $R^2$ and $R^3$ are as defined above; or pharmaceutically acceptable salts, solvates or prodrugs thereof.

There is nothing in any of the foregoing references, or in the general prior art, to suggest the novel alpha-amino, thio, oxo substituted ketones of the present invention as cytosolic phospolipase A2 inhibitors.

SUMMARY OF THE INVENTION

An object of the present invention is to provide novel alpha- and gamma-hetero substituted ketone compounds which inhibit cytosolic phopholipase A2 enzymes that are pro-inflammatory mediators.

This invention relates to novel cytosolic phospholipase inhibitors represented by formula I, or a pharmaceutically acceptable salt thereof

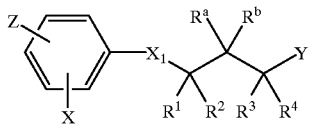

wherein $X_1$ is $O$, $S(O)_n$,

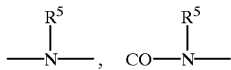

or $—CH_2—$, with the proviso that when $X_1$ is $—CH_2—$, $R_1$ and $R_2$ are only halogen;

n is 0, 1 or 2;

$R^a$ and $R^b$ when taken together form an oxo (=O) group, or $R^a$ and $R^b$ are each independently hydrogen, OH, $OCOR^9$, $NH_2$, $N_3$, $NHCOOR^9$, $NHCOCOR^9$, $NHSO_2R^9$ or F;

X is H, $CF_3$, $OCF_3$, halogen, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^8$, CN, $C(O)NR^6R^7$, $PO_3R^8$, $SO_3R^8$, heterocyclic, $OR^8$, SH, $S(O)_nR^9$, $NR^6R^7$, $NH(CO)NR^6R^7$, $NH(CO)OR^9$, aryl or heteroaryl, said aryl or heteroaryl being optionally substituted by one or two groups independently selected from $NR^6R^7$, $OR^8$, $COOR^8$, $SO_3R^8$, $OCOR^9$, $PO_3R^8$, $C(O)NR^6R^7$ or heterocyclic;

$R^1$ and $R^2$ are each independently H, halogen, $OR^9$, $C_1$–$C_7$ alkyl, $C_2$–$C_7$ alkynyl, $C_2$–$C_7$ alkenyl or $C_3$–$C_7$ cycloalkyl, said alkyl, alkenyl, alkynyl or cycloalkyl group being optionally substituted by $COOR^8$, CN, $C(O)NR^6R^7$, $PO_3R^8$, $SO_3R^8$, heterocyclic, $OR^8$, SH, $S(O)_nR^9$, $NR^6R^7$, $NH(CO)NR^6R^7$, $NH(CO)OR^9$, $OC(O)OR^9$, aryl or heteroaryl, said aryl or heteroaryl being optionally substituted with one or two groups independently selected from $NR^6R^7$, $OR^8$, $COOR^8$, $SO_3R^8$, $OCOR^9$, $PO_3R^8$, $C(O)NR^6R^7$ or heterocyclic;

$R^3$, $R^4$ and Y are each independently H, halogen, $OR^{10}$, $S(O)_nR^{10}$, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^8$, CN, $C(O)NR^6R^7$, $PO_3R^8$, $SO_3R^8$, heterocyclic, $OR^8$, SH, $S(O)_nR^9$, $NR^6R^7$, $NH(CO)NR^6R^7$, $NH(CO)OR^9$, $OC(O)OR^9$, aryl or heteroaryl, said aryl or heteroaryl being optionally substituted by one or two groups independently selected from $NR^6R^7$, $OR^8$, $COOR^8$, $SO_3R^8$, $OCOR^8$, $PO_3R^8$, $C(O)NR^6R^7$ or heterocyclic, with the proviso that not all of $R^3$, $R^4$ and Y may be the same halogen;

$R^5$, $R^6$ and $R^7$ are each independently H, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^8$, CN, $OR^8$, $NR^8R^9$, $SO_3R^8$, $PO_3R^8$, halogen, aryl or heteroaryl, said aryl or heteroaryl being optionally substituted by one or two groups independently selected from $COOR^8$, $SO_3R^8$, $PO_3R^8$ or heterocyclic;

$R^8$ is H, $C_1$–$C_7$ saturated straight chain alkyl or cycloalkyl, $CF_3$ or $CH_2CF_3$;

$R^9$ is same as $R^8$ but is not hydrogen;

$R^{10}$ is $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^8$, CN, $C(O)NR^6R^7$, $PO_3R^8$, $SO_3R^8$, heterocyclic, $OR^8$, SH, $S(O)_nR^9$, $NR^6R^7$, $NH(CO)NR^6R^7$, $NH(CO)OR^9$, aryl or heteroaryl, said aryl or heteroaryl being optionally substituted by one or two groups independently selected from $NR^6R^7$, $OR^8$, $COOR^8$, $SO_3R^8$, $OCOR^8$, $PO_3R^8$, $C(O)NR^6R^7$ or heterocyclic;

Z is $OR^{11}$, $S(O)_nR^{11}$, $NR^{11}R^{12}$ or $CHR^{11}R^{12}$;

$R^{11}$ and $R^{12}$ are each independently hydrogen, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $NR^{13}R^{14}$, $S(O)_nR^{13}$ or $OR^{13}$, with the proviso that both $R^{11}$ and $R^{12}$ may not be hydrogen;

$R^{13}$ and $R^{14}$ are each independently H, $SiR^{15}R^{16}R^{17}$, $C_1$–$C_7$ alkyl, $C_2$–$C_7$ alkenyl, $C_2$–$C_7$ alkynyl, aryl or $C_3$–$C_7$ cycloalkyl, said alkyl, alkenyl, alkynyl, aryl or cycloalkyl group being optionally substituted by one to three groups independently selected from $COOR^8$, $OR^8$, $SiR^{15}R^{16}R^{17}$, $OR^{15}$, aryl, biaryl or heteroaryl, said aryl, biaryl or heteroaryl being optionally substituted with one to three groups independently selected from halogen, $CF_3$, $OR^8$, $COOR^8$, $NO_2$, or CN;

$R^{13}$ and $R^{14}$ when taken together may form a 5–7 membered heterocyclic ring with one or more heteroatoms selected from O, N and S; said ring being optionally substituted by $OR^8$, $COOR^8$, or $C(O)NR^5R^6$;

$R^{15}$, $R^{16}$, $R^{17}$ are each independently aryl, benzyl, benzhydryl, biaryl, heteroaryl, $(C_1$–$C_6)$ alkyl-aryl or $(C_1$–$C_6)$ alkyl-heteroaryl, said aryl radical being optionally substituted by halogen, $CF_3$, $OR^8$, $COOR^8$, $NO_2$, CN, or $C_1$–$C_7$ alkyl.

This invention also provides methods for inhibiting cytosolic $PLA_2$ in a mammal in need thereof which comprise administering to said mammal a therapeutically effective amount of a compound of formula I and methods for using the compounds of formula I to treat various diseases characterized by inappropriate activation of the cytosolic $PLA_2$ enzymes such as asthma, allergic rhinitis, cerebral ischemia, Alzheimer's Disease, rheumatoid arthritis, acute pancreatitis, inflammatory bowel disease, psoriasis, gout, neutrophil and platelet activation, chronic skin inflammation, shock, trauma-induced inflammation such as spinal cord injury, damage to the skin resulting from UV light or burns and macrophage activation. In further aspects, the present invention provides pharmaceutical compositions comprising a therapeutically effective amount of a compound of formula I and a pharmaceutically acceptable carrier and processes for preparing the compounds of formula I.

DETAILED DESCRIPTION

The object of this invention was to discover a selective $cPLA_2$ inhibitor which is active, both topically and orally, in treating inflammatory disease of the skin and other tissues as well as other chronic and acute conditions which have been linked to inappropriate activation of the $cPLA_2$ enzymes. Preferably such compound would also be devoid of undesirable lipid-perturbing activities associated with skin irritation.

The above-mentioned objectives have been met by the compounds of formula I described above.

Definitions

In the present application the numbers in the subscript after the symbol "C" define the number of carbon atoms a particular group can contain. For example, "$C_1$–$C_7$ alkyl" refers to straight and branched chain alkyl groups with 1 to 7 carbon atoms. Similarly, "$C_2$–$C_7$ alkenyl" or "alkynyl" refers to an unsaturated hydrocarbon group containing form 2 to 7 carbon atoms and at least one carbon-carbon double bond or triple bond.

The term "halogen" or "halo" as used herein refers to fluorine, chlorine, bromine or iodine, preferably fluorine and chlorine.

"Aryl" as used herein refers to a $C_6$ monocyclic aromatic ring system or a $C_9$ or $C_{10}$ bicyclic carbocyclic ring system having one or two aromatic rings such as phenyl or naphthyl. It may also refers to a $C_{14}$ tricyclic carbocyclic ring system having two or three aromatic rings such as anthracenyl or phenanthrenyl. Unless otherwise indicated, "substituted aryl" refers to aryl groups substituted with one or more (preferably from 1 to 3) substituents independently selected from ($C_1$–$C_6$)alkyl, haloalkyl, ($C_1$–$C_6$)alkoxy, ($C_1$–$C_6$) alkoxy-carbonyl, ($C_1$–$C_6$)alkanoyl, hydroxy, halo, mercapto, nitro, amino, cyano, ($C_1$–$C_6$)alkylamino, di($C_1$–$C_6$)alkylamino, carboxy, aryl, aryl ($C_1$–$C_6$)alkyl, aryl ($C_1$–$C_6$)alkoxy, heterocyclic, heterocyclic ($C_1$–$C_6$)alkyl and the like. The term "biaryl" refers to two $C_6$ monocyclic aromatic ring systems or two $C_9$ or $C_{10}$ bicyclic carbocyclic ring systems linked together such as o-, m- and p-biphenyl or o-, m- and p-binaphthyl. The term "heteroaryl" refers to a 5- or 6-membered aromatic ring system or a 9- or 10-membered bicyclic aromatic ring system containing one, two or three heteroatoms selected from N, O and S. The term "benzhydryl" refers to a carbon atom bearing two aryl, bis-aryl or heteroaryl groups.

The term "heterocyclic" as used herein refers to a 4-, 5- or 6-membered ring containing one, two or three heteroatoms selected from N, O and S. The 5-membered ring has 0–2 double bonds and the 6-membered ring has 0–3 double bonds. The nitrogen heteroatoms can be optionally quaternized or N-oxidized. The sulfur heteroatoms can be optionally S-oxidized. The term "heterocyclic" also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolidinyl, pyridyl, piperidyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, benzimidazolyl, benzothiazolyl, benzoxazolyl, benzofuranyl, furyl, dihydrofuranyl, tetrahydrofuranyl, pyranyl, dihydropyranyl, dioxolanyl, thienyl, benzothienyl and diaxanyl.

Some of the compounds described herein contain one or more asymmetric centers and may thus give rise to diastereomers and optical isomers. The present invention is meant to include such possible diastereomers as well as their racemic and resolved, enantiomerically pure forms, and pharmaceutically acceptable salts thereof.

As mentioned above the invention also includes pharmaceutically acceptable salts of the compounds of formula I. A compound of the invention can possess a sufficiently acidic, a sufficiently basic, or both functional groups. Accordingly, a compound may react with any of a number of inorganic bases, and organic and inorganic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogen phosphate, dihydrogen phosphate, metaphosphate, pyrophosphate, chloride, bromide, iodide, acetate, propionate, decanoate, caprylate, acrylate, formate, isobutyrate, caproate, heptanoate, propionate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylene-sulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Suitable organic bases include trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine, or the like pharmaceutically acceptable amines. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

A preferred embodiment of the present invention includes compounds and pharmaceutically acceptable salts thereof in which $R^3$, $R^4$ and Y are each independently H, halogen, $OR^{10}$, $S(O)_nR^{10}$, $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^8$, CN, $C(O)NR^6R^7$, $PO_3R^8$, $SO_3R^8$, heterocyclic, $OR^8$, SH, $S(O)_nR^9$, $NR^6R^7$, $NH(CO)NR^6R^7$, $NH(CO)OR^9$, $OC(O)OR^9$, aryl or heteroaryl, said aryl or heteroaryl being optionally substituted by one or two groups independently selected from $NR^6R^7$, $OR^8$, $COOR^8$, $SO_3R^8$, $OCOR^8$, $PO_3R^8$, $C(O)NR^6R^7$ or heterocyclic, with the proviso that not all of $R^3$, $R^4$ and Y may be the same halogen.

Within this embodiment, more preferred compounds are those in which $X_1$ is O, $S(O)_n$ or —$CH_2$— with the proviso that when $X_1$ is —$CH_2$—, $R_1$ and $R_2$ are only halogen and Y is $OR^{10}$ or $S(O)_nR^{10}$ in which $R^{10}$ is $C_1$–$C_7$ alkyl, $C_2$–$C_7$ alkenyl, $C_2$–$C_7$ alkynyl or $C_3$–$C_7$ cycloalkyl, said alkyl, alkenyl, alkynyl or cycloalkyl group being optionally substituted by $COOR^8$, CN, $C(O)NR^6R^7$, $PO_3R^8$, $SO_3R^8$, heterocyclic, $OR^8$, SH, $S(O)_nR^9$, $NR^6R^7$, $NH(CO)NR^6R^7$, $NH(CO)OR^9$, $OC(O)OR^9$, aryl or heteroaryl, said aryl or heteroaryl being optionally substituted by one or two groups independently selected from $NR^6R^7$, $OR^8$, $COOR^8$, $SO_3R^8$, $OCOR^8$, $PO_3R^8$, $C(O)NR^6R^7$ or heterocyclic. The above embodiment in which $R^a$ and $R^b$ are each independently hydrogen or OH is a most preferred embodiment. Another most preferred embodiment comprises compounds in which $R^a$ and $R^b$ are each independently hydrogen, F, $OCOR^9$, $NH_2$, $N_3$, $NHCOOR^9$ or $NHCOCOR^9$ in which $R^9$ is as defined above.

For all of the above-described embodiments, the most preferred Z substituent is

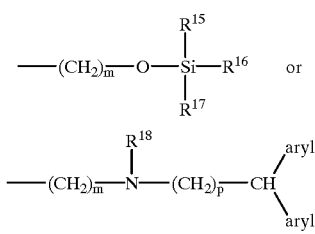

in which m and p each independently represent an integer of one to six, $R^{15}$, $R^{16}$, $R^{17}$ are each independently $C_1$–$C_7$ alkyl, $R^{18}$ is $C_1$–$C_7$ alkyl and aryl represents

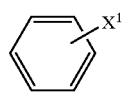

in which $X^1$ is halogen.

The present invention also includes solvated forms of the compounds of formula I, particularly hydrates, in which the ketone group exists as a mixture of ketonic I and hydrated forms II and are each independently interconvertible and pharmacologically active.

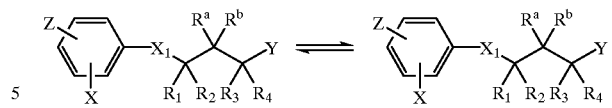

Biological Activity

Assay for determining activity as $cPLA_2$ inhibitors:

$^3$H-arachidonate-labeled U937 membranes were prepared from U937 cells grown in RPMI 1640 medium containing L-glutamine supplemented with 10% fetal calf serum and 50 µg/ml gentamycin in a 5% $CO_2$ incubator at 37° C. Sixteen hours prior to harvesting the cells, $^3$H-arachidonate (100 Ci/mmol) was added to the cell culture (1×10$^6$ cells/ml, 0.5 µCi/ml). After washing the cells with HBSS (Hank's Balanced Salts) containing 1 mg/ml HSA (Human Serum Albumin), the cells were lysed by nitrogen cavitation and the homogenate was centrifuged at 2,000×g for 10 minutes. The supernatant was further centrifuged at 50,000×g for 30 minutes after which the pellet was resuspended in water and autoclaved at 120° C. for 15 minutes to inactivate any residual phospholipase $A_2$ activity. This suspension was then recentrifuged at 50,000×g for 30 minutes and the pellet resuspended in distilled water.

Assays of $cPLA_2$ activity using these $^3$H-arachidonate-labeled U937 membranes as substrate typically employ human recombinant $cPLA_2$ (see Burke et al., *Biochemistry* 34: 15165–15174, 1995) and membrane substrate (22 µm phospholipid) in 20 mm HEPES [N-(2-hydroxyethyl) piperazine-N$^1$-(2-ethanesulfonic acid)] buffer, pH 8, containing 6 mm $CaCl_2$, 0.9 mg/ml albumin and 4 m glycerol. Enzyme assays are allowed to proceed for 3 hours at 37° C. before removing the non-hydrolyzed membranes. The hydrolyzed, radiolabeled fatty acid is then measured by liquid scintillation counting of the aqueous phase.

The effects of inhibitor are calculated as percent inhibition of $^3$H-arachidonate formation, after correcting for nonenzymatic hydrolysis, as compared to a control lacking inhibitor according to the following formula:

percent inhibition=((Control DPM−Inhibitor DPM)/Control DPM)×100%

Various concentrations of an inhibitor were tested, and the percent inhibition at each concentration was plotted as log concentration (abscissa) versus percent inhibition (ordinate) to determine the $IC_{50}$ values.

In this assay the compounds of Examples 1–39 below exhibited $cPLA_2$ $IC_{50}$ values in the range of from about 1 to 50 µm.

Since the compounds of the present invention are selective inhibitors of cytosolic phospholipase $A_2$, they are of value in the treatment of a wide variety of clinical conditions.

Inflammatory disorders which may be treated by inhibition of cytosolic $cPLA_2$ include such conditions as arthritis, psoriasis, asthma, inflammatory bowel disease, gout, trauma-induced inflammation such as spinal cord injury, Alzheimer's Disease, cerebral ischemia, chronic skin inflammation, shock, damage to skin resulting from exposure to ultraviolet light or burns, allergic rhinitis, acute pancreatitis, and the like.

The compounds of the present invention have also been found to be very stable towards keto-reduction. It has been shown that a reliable method to assess keto-stability of compounds is to measure the percent of such compounds remaining after incubation with erythrocyte lysates [Rady-Pentek P., et al., Eur. J. Clin. Pharmacol., 1997, 52(2): 147–153]. The assay is the following.

Male Wistar rates were anesthetized with $CO_2$ and then blood was removed by direct cardio-puncture or through a pre-inserted jugular vein canula into syringes that were pre-rinsed with heparin. The blood was then inserted into heparanized tubes and placed on ice. The blood was centrifuged at 3000 rpm for 5 minutes to separate the plasma. The plasma was removed and an equivalent volume of sterile water was mixed with the erythrocyte fraction. This was mixed by inversion and left on ice for several minutes to lyse the erythrocytes. The erythrocyte-water mixture was then centrifuged at 3000 rpm for 5 minutes to pellet the cellular debris.

Each compound was dissolved in methanol (1 ml) to produce a 2 mM solution. From this solution, 50 μl aliquot was made up to 1 ml in 50% methanol to produce a 100 μM stock solution. From this solution, a dose solution was prepared by diluting 100 μl to 2 ml of a 0.1 M potassium phosphate buffer (pH=7.4) to produce a 2 μM final incubation dilution.

The lysate (250 μl) was then aliquoted into eppendorf tubes, 6 for each compound, i.e. 0 time, 15 minutes, 60 minutes in duplicate. To these aliquots was added 200 μl of the dose solution and this was preheated to 37° C. for 2–3 minutes prior to the addition of NADPH (1 mM final concentration) to start the reactions. The reactions were terminated with the addition of either 0.5 ml or 1 ml of acetonitrile. Following centrifugation at 8000×g for 5 minutes, the supernatant was removed and stored at −20° C. until analysis could proceed by quantitative LC/MS. Samples were analyzed by electrospray ionization (ESI) on a Micromass ZMD 2000® single quadrupole mass spectrometer coupled to a Shimadzu HPLC system. The percent of compound remaining following 15 minutes and 60 minutes incubation is calculated relative to the 0 time point.

Administration Modes

The compounds of formula I are usually administered in the form of pharmaceutical compositions. They can be administered by a variety of routes including oral, rectal, transdermal, subcutaneous, intravenous, intramuscular, and intranasal. The compounds are effective as both injectable and oral compositions. Such compositions are prepared in a manner well known in the pharmaceutical art and comprise at least one active compound defined by formula I and a pharmaceutically acceptable carrier.

In making the compositions employed in the present invention the active ingredient is usually mixed with an excipient, diluted by an excipient or enclosed within a carrier which can be in the form of a capsule, sachet, paper or other container. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

The compounds of the present invention can be prepared by various methods which are known in the art. Illustrative methods of preparation are provided in the reaction schemes which follow and in the Examples.

Method of Preparation

Preparation of compounds of formula I may be accomplished via one or more of the synthetic schemes which are described below.

Scheme A

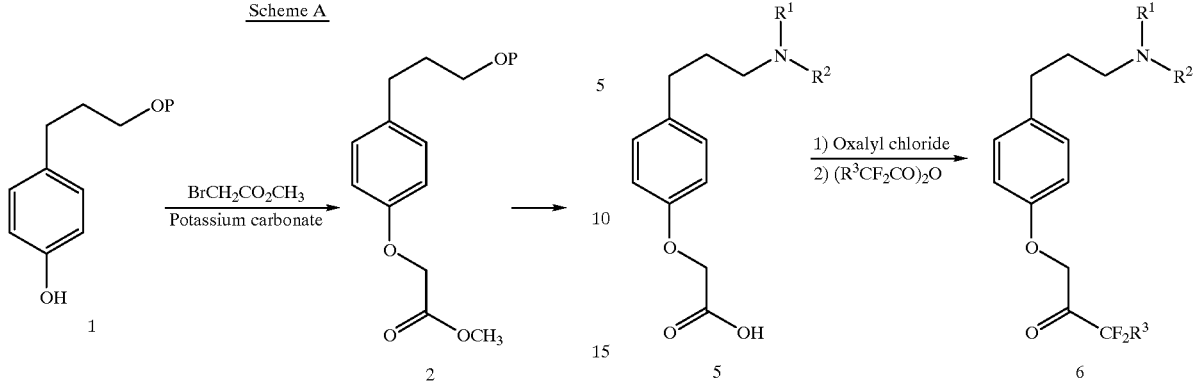

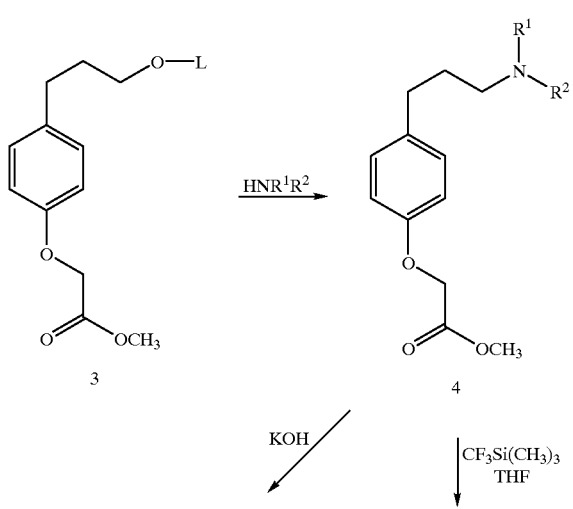

Scheme A describes a method of preparing compounds of generic structure 6. Reaction of phenol 1 in which P is a protecting group such as tert-butyl diphenylsilyl with a bromo ester such as methyl bromoacetate in a solvent like acetonitrile or N,N-dimethylformamide in presence of a base such as potassium carbonate affords 2. Deprotection of 2 with a reagent such as tetrabutyl ammonium fluoride gave the alcohol 2 (P=H) that was activated via a group like a mesyloxy to give 3 (L=Ms). Reaction of 3 with a secondary amine $R^1R^2NH$ in a solvent such as acetonitrile gave the amine 4. Reaction of 4 with a trimethylsilylfluoroalkyl reagent such as trifluoromethyltrimethylsilane in a solvent such as toluene using a catalyst like tetrabutylammonium fluoride gave, after aqueous hydrolysis, ketone 6. Alternatively, the ester 4 can be saponified to the acid 5 by a base such as potassium hydroxide and in a solvent such as aqueous ethanol. The acid 5 can be reacted with a reagent such as oxalyl chloride to give an intermediate acid chloride which is then treated with an anhydride such as trifluoroacetyl anhydride or chlorodifluoroacetic anhydride and a base such as pyridine in a solvent like toluene to give the ketone 6.

Scheme B

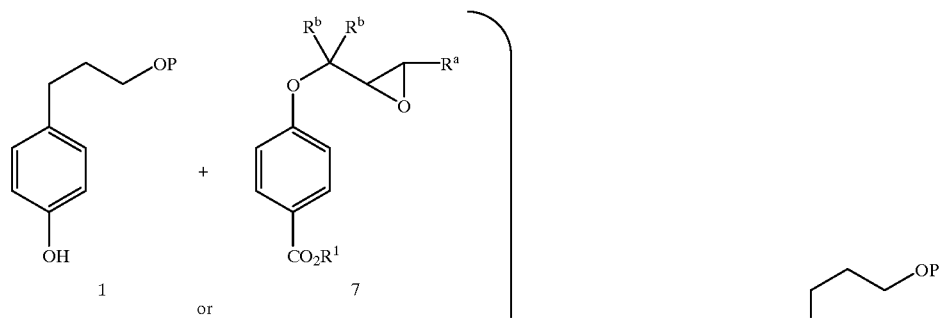

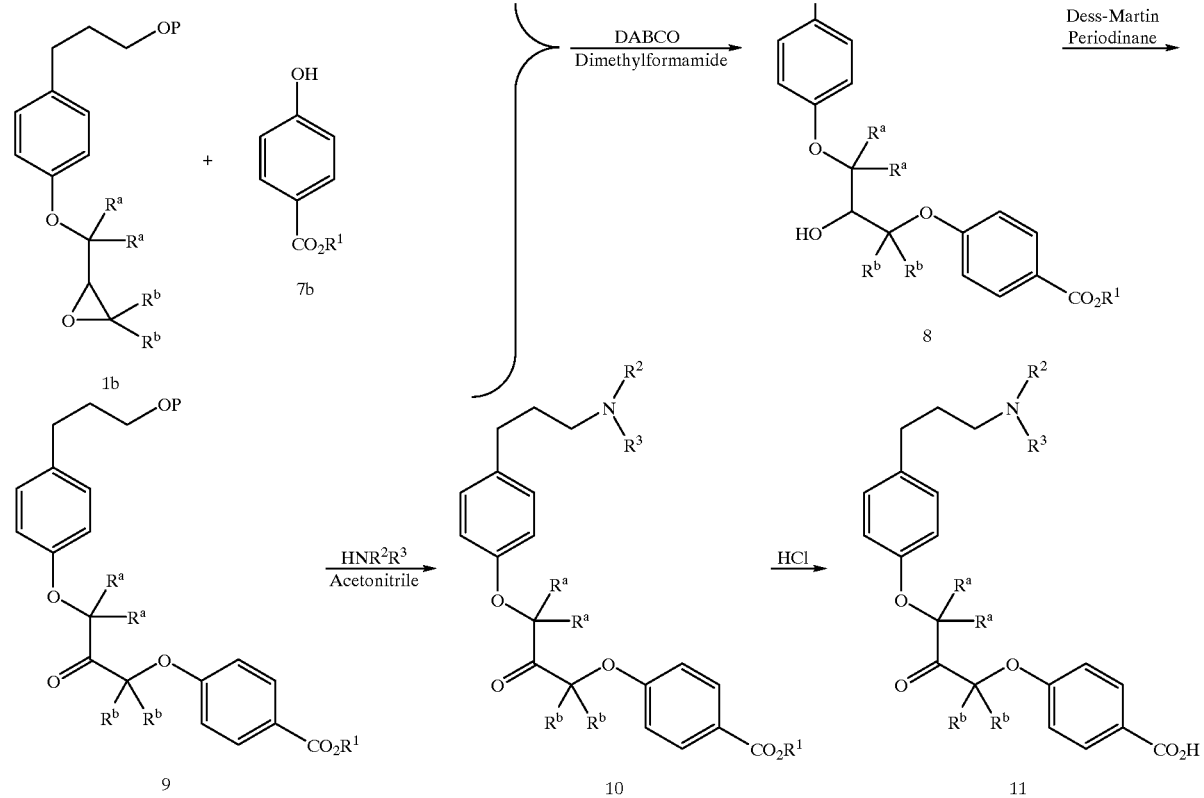

Scheme B describes the preparation of compounds of general structure 11. Reaction of phenol 1 in which P is a protecting group such as tert-butyldiphenylsilyl with an epoxide such as 7 in a solvent such as N,N-dimethylformamide catalysed by a base such as 1,4-diazabicyclo[2,2,2]octane afforded 8. Alternatively, reaction of a phenol 7b with an epoxide 1b in which $R^a$ and $R^b$ can be an hydrogen atom or a lower alkyl like methyl also gave compound 8. Compound 8 can be oxidized to the ketone 9 by reaction with an oxidant such as 1,1,1-triacetoxy-1,1-dihydro-1,2-benziodoxol-3(1H)-one (Dess-Martin periodinane) in a solvent like dichloromethane. Deprotection of the silyl group P in 9 with a reagent such as tetrabutylammonium fluoride and in a solvent like tetrahydrofuran gave the alcohol 9 (P=H). Reaction of the alcohol 9 (P=H) with an alkyl or arylsulfonyl chloride such as methanesulfonyl chloride gave a sulfonate ester 9 (P=Ms) that was reacted with a secondary amine of general formula $R^2R^3NH$ in a solvent like acetonitrile to give 10. Reaction of 10 ($R^1$=tBu) with an acid such as trifluoroacetic acid or hydrochloric acid in a solvent like dichloromethane yielded the amine 11 as the corresponding salt.

Scheme C

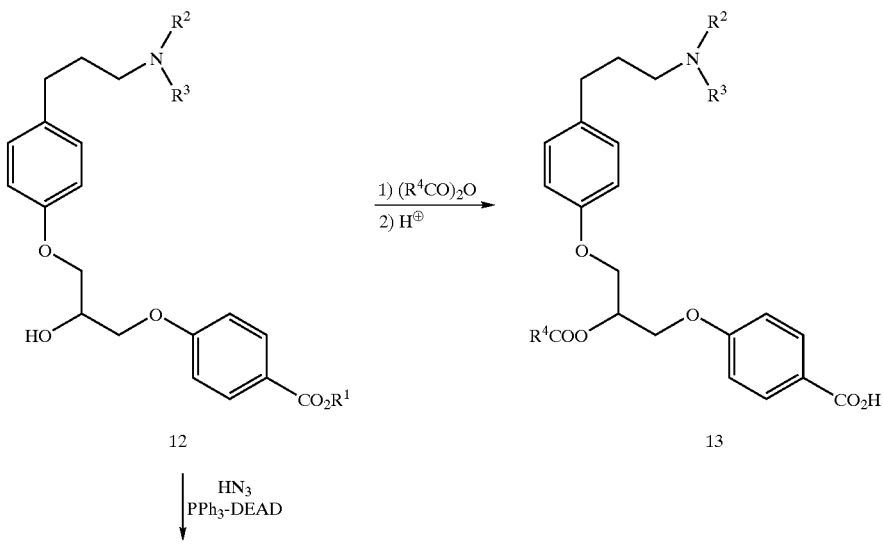

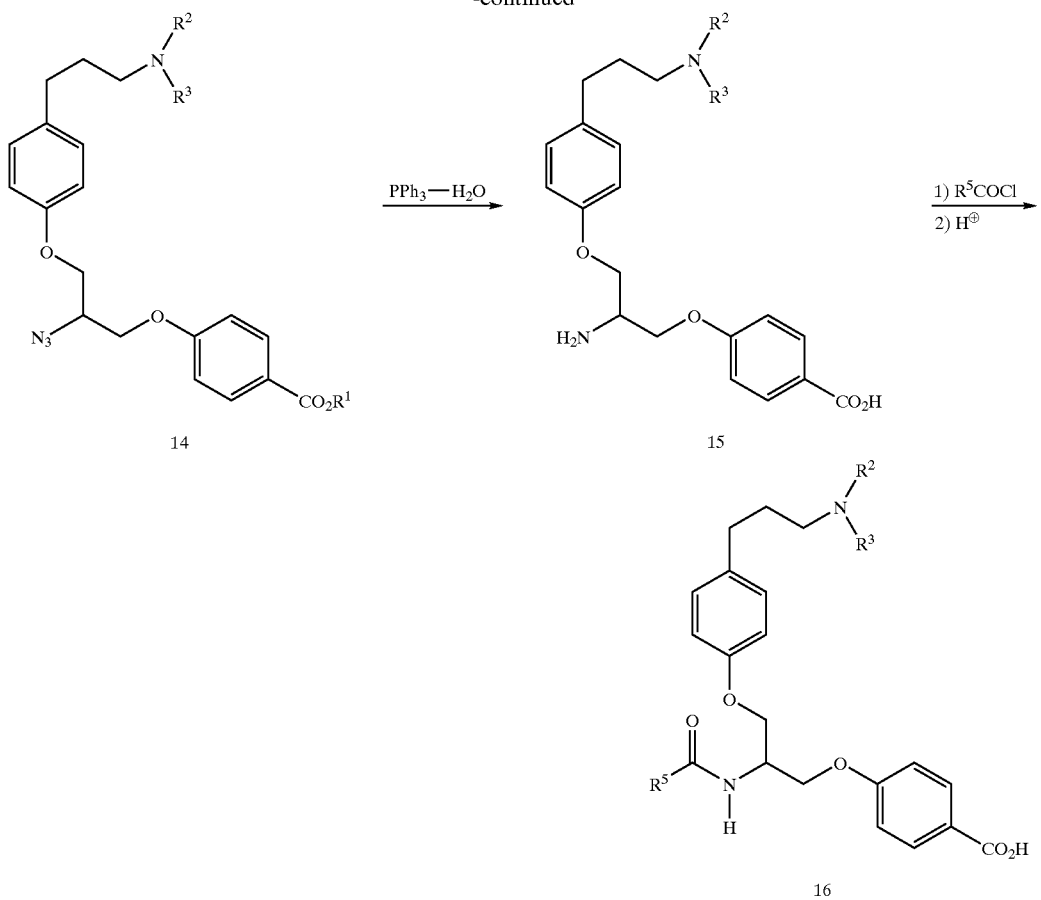

Scheme C describes the preparation of compounds of esters or amides of general structure 13 or 16. Reaction of alcohol 12 with an acid anhydride or an acid chloride in presence of a base such as pyridine gave an ester of general structure 13. Alcohol 12 can also be reacted under Mitsunobu condition with hydrazoic acid or an equivalent azide source to give the azido derivative 14. The azido derivative 14 can be reduced to the amine derivative 15 with a reducing agent like triphenylphosphine and water. Reaction of the amine derivative 15 with an acyl chloride such as acetyl chloride or pyruvyl chloride gave the amide 16 after deprotection of the benzoic ester. Alternatively 16 can be obtained by coupling of an acid $R^5CO_2H$ with the amine 15 in presence of a coupling reagent such as dicyclohexylcarbodiimide or 2-ethoxy-1-ethoxycarbonyl-1,2-dihydroquinoline (EEDQ) followed by deprotection.

Scheme D

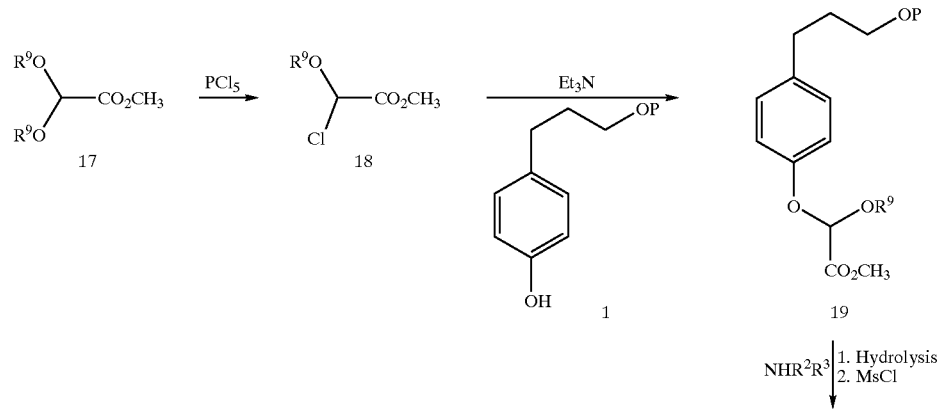

27 28

-continued

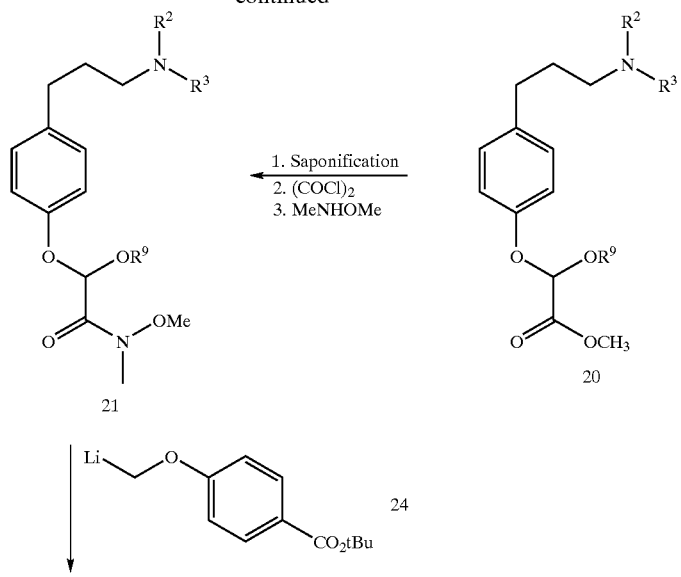

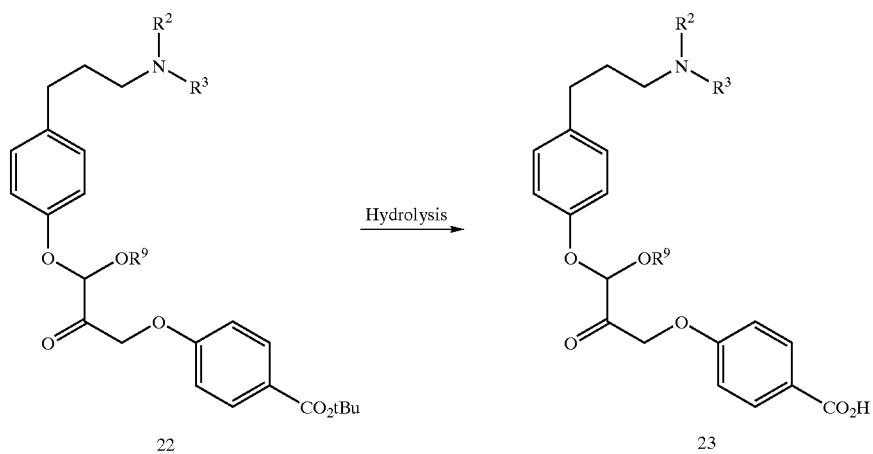

Scheme D describes the preparation of compounds wherein $R^1$ is $OR^9$. Hence, the various alkyl dialkoxyacetates 17 may be treated with a chlorinating agent such as phosphorous pentachloride to give the corresponding chlorides 18. Substitution of these chlorides with phenol 1 afford compound of type 19. Deprotection of 19 with a reagent such as tetrabutylammonium fluoride gave the alcohol (P=H) that was activated via a group like a mesyloxy. Reaction of this compound with a secondary amine $R^1R^2NH$ in a solvent such as acetonitrile gave the amine 20. Saponification of the ester in conditions known in the art followed by activation with oxalyl chloride gave the corresponding acid chloride which was then converted to the Weinreb amide 21 in the usual acylation conditions. Reaction of this compound with a lithium derivative of type 24 afford the coupling adduct 22 which was then hydrolyzed to the acid 23.

SCHEME E

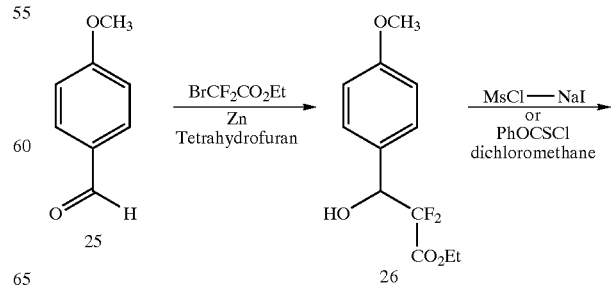

-continued

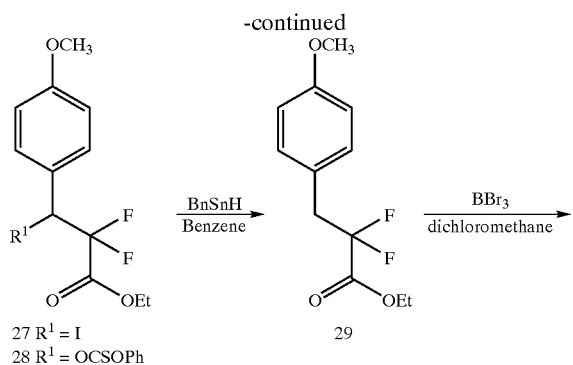

27 R¹ = I
28 R¹ = OCSOPh

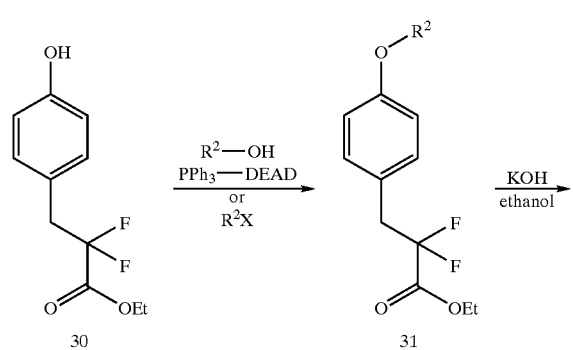

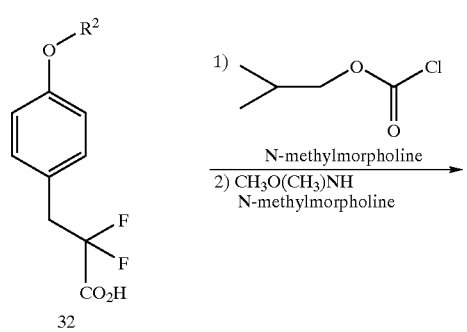

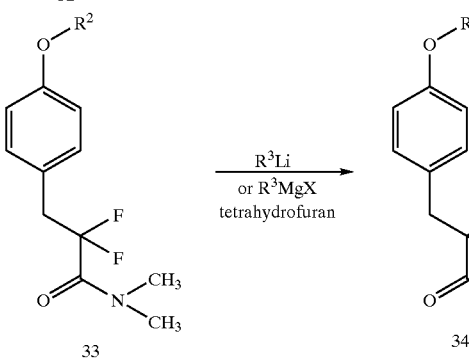

Scheme E shows a method of preparing compounds of general structure 34. Reaction of 4-methoxybenzaldehyde 25 and a bromodifluoro ester such as ethyl bromodifluoroacetate with zinc in a solvent like tetrahydrofuran under Reformatsky conditions gave the alcohol 26. Reaction of the alcohol 26 with an alkyl or aryl sulfonyl chloride such as methanesulfonyl chloride in a solvent like dichloromethane gave an intermediate sulfonate ester. This intermediate sulfonate was treated with sodium iodide in a solvent like acetone to give the iodide 27. Alternatively, the alcohol 26 can be reacted with an aryl chlorothionoformate such as phenylchlorothionoformate to give the phenylthianocarbonate 28. The iodide 27 or the phenylthianocarbonate 28 were then reacted with an alkyltin hydride such as tributyltin hydride in presence of 2,2'-azobisisobutyronitrile and in a solvent such as benzene to give the de-oxygenated ester 29. Compound 29 was then treated with a reagent such as boron tribromide to give the phenol 30. Reaction of the phenol 30 with an alcohol of general formula $R^2OH$ under Mitsunobu conditions gave the ether 31. Alternatively, the phenol 30 can be alkylated with a substituted alkyl halide ($R^2X$) using a basic catalyst such as potassium carbonate and in a solvent such as acetonitrile or dimethylformamide to give the ether 31. Compound 31 was then saponified to the acid 32 by treatment with a base such as sodium hydroxide or potassium hydroxide in a solvent such as aqueous ethanol followed by acidification with a diluted acid. The acid 32 was then activated as the mixed anhydride by reaction with an alkyl chloroformate such as isobutyl chloroformate in presence of a base such as N-methylmorpholine and in a solvent like dichloromethane. Reaction of the mixed anhydride with N,0-dimethyl hydroxylamine in presence of a base such as N-methylmorpholine and in a solvent such as dichloromethane gave the Weinreb amide 33. The amide 33 can be treated with lithium reagents of general formula $R^3Li$ or Grignard reagents of general formula $R^3MgBr$ in a solvent like tetrahydrofuran to give the fluoroketone 34.

SPECIFIC EXAMPLES

The following examples further illustrate the preparation of the compounds of formula I. The examples are illustrative only and are not intended to limit the scope of the invention in any way. The following abbreviations have the indicated meanings:

| | |
|---|---|
| AcOH | acetic acid |
| EWG | electron-withdrawing groups |
| DIAD | diisopropyl azodicarboxylate |
| TFAA | trifluoroacetic anhydride |
| r.t. | room temperature |
| THF | tetrahydrofuran |
| TFA | trifluoroacetic acid |
| DABCO | 1,4-diazabicyclo[2.2.2]octane |
| EEDQ | N-ethoxycarbonyl-2-ethoxy-1,2-dihydroxyquinoline |
| DMF | N,N-dimethylformamide |
| DEAD | diethyl azodicarboxylate |
| mCPBA | m-chloroperbenzoic acid |
| Me | $CH_3$ |
| Ph | phenyl |
| tBu | tert-butyl |

Example 1

3-[4-[3-(tert-Butyldiphenylsilyloxy)propyl]phenoxy]-1-chloro-1,1-difluoro-2-propanone

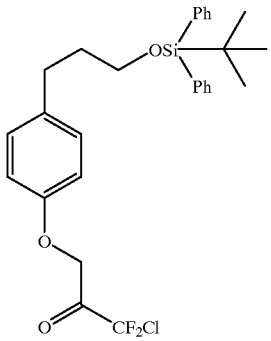

3-(4-Hydroxyphenyl)-1-(tert-butyldiphenylsilyloxy)propane

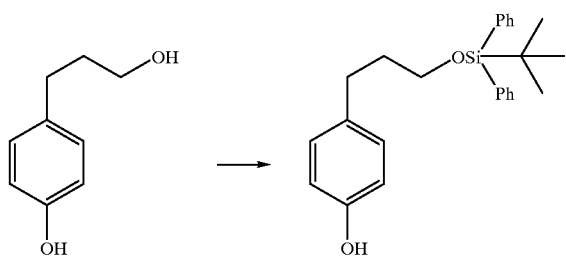

A solution of 3-(4-hydroxyphenyl)-1-propanol (10.0 g, 66.0 mmol) and imidazole (6.7 g, 98.4 mmol) in N,N-dimethylformamide (50 ml) was cooled to 0–5° C. and treated dropwise with tert-butylchlorodiphenylsilane (21.5 g, 78.2 mmol). The resulting mixture was stirred at 0–5° C. for 2 hours and then quenched by addition of water (400 ml) and toluene (500 ml). The organic phase was washed with water, brine and dried over anhydrous magnesium sulfate. Evaporation of the solvent and chromatography of the residue on silica gel (elution toluene-ethyl acetate, 95:5) gave 24.8 g (96%) of the title material as a clear oil.

Anal. Calcd. for $C_{25}H_{30}O_2Si$: C, 76.88; H, 7.74. Found: C, 76.74; H, 7.67.

Methyl [4-[3-(tert-butyldiphenylsilyloxy)propyl]phenoxy]acetate

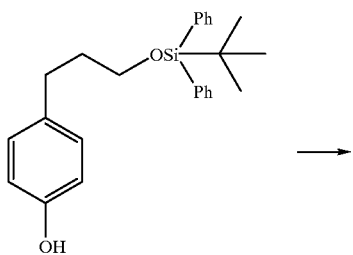

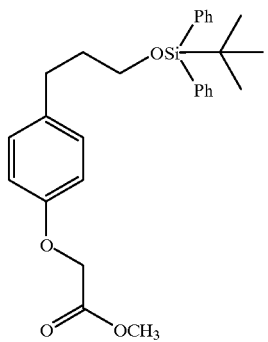

A solution of 3(4-hydroxyphenyl)-1-(tert-butyldiphenylsilyloxy)propane (3.91 g, 10.0 mmol) and methyl bromoacetate (3.0 g, 19.7 mmol) in acetonitrile (100 ml) was treated with powdered anhydrous potassium carbonate (10 g) and the resulting mixture was heated under reflux for 1 hour. The cooled mixture was filtered and the filtrate was concentrated in vacuo. Chromatography of the residue on silica gel (elution toluene-ethyl acetate, 98:2) gave 4.36 g (94%) of the title material as clear oil.

[4-[3-(tert-Butyldiphenylsilyloxy)propyl]phenoxy]acetic acid

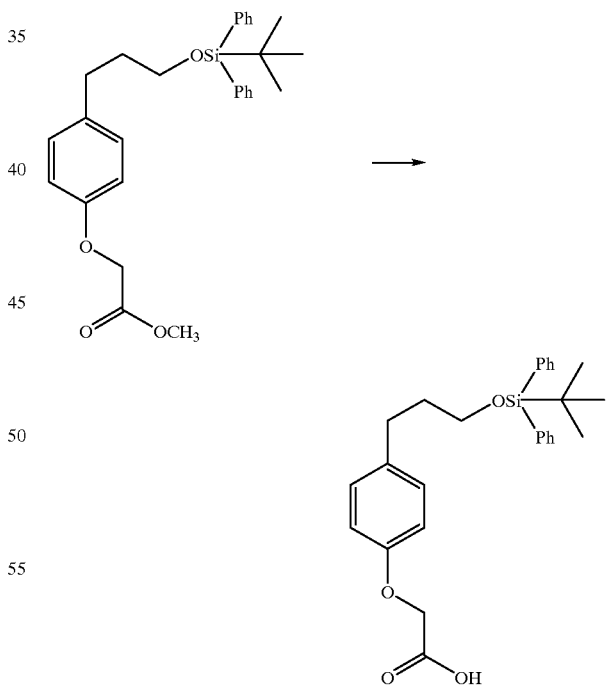

A solution of methyl [4-[3-(tert-butyldiphenylsilyloxy)propyl]phenoxy]acetate (4.36 g, 9.4 mmol) in 80% aqueous ethanol (100 ml) was treated with potassium hydroxide (2 g) and the resulting mixture was heated at 50° C. for 2 hours.

The solvent was then evaporated in vacuo. Ice water and ethyl acetate were added and the aqueous phase was carefully adjusted to pH with 1N hydrochloric acid. The organic phase was then washed with brine, dried (magnesium sulfate) and evaporated under reduced pressure to give a white solid. Recrystallization from hexane gave 3.41 g (81%) of the title acid as white crystals: mp 87–88° C.

3-[4-[3-(tert-Butyldiphenylsilyloxy)propyl]phenoxy]-1-chloro-1,1-difluoro-2-propanone

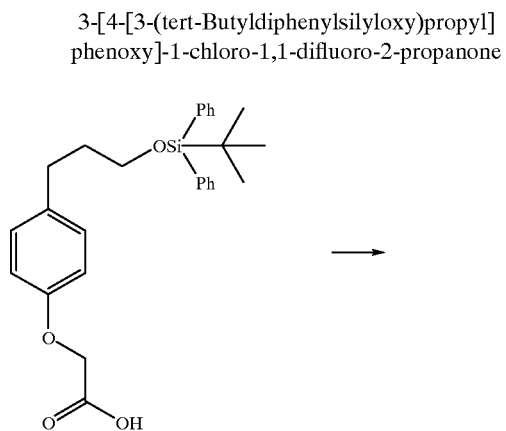

A solution of [4-[3-(tert-butyldiphenylsilyloxy)propyl]phenoxy]acetic acid (3.41 g, 7.6 mmol) in dichloromethane (30 ml) was treated with oxalyl chloride (0.96 g, 7.6 mmol) and a small drop of N,N-dimethylformamide and the resulting solution was stirred at 22° C. for 1 hour. The solvent was then evaporated in vacuo and the residual oil was diluted with toluene (50 ml) and cooled to 0° C. This solution was treated with chlorodifluoroacetic anhydride (5.54 g, 22.8 mol) followed by pyridine (1.80 g, 22.8 mmol) added dropwise over 5 minutes. After 15 minutes at 0° C., the mixture was allowed to warm to 22° C. and stirred for 2 hours. The mixture was then cooled again to 0° C. and treated dropwise with water (5 ml). After 10 minutes at 22° C., the mixture was diluted with ethyl acetate, washed with saturated sodium bicarbonate, brine and dried (magnesium sulfate). Evaporation of the solvent and chromatography of the residue on silica gel (elution toluene-ethyl acetate, 9:1) gave 1.02 g (26%) of the title material as a light yellow oil.

Anal. Calcd. for $C_{28}H_{31}ClF_2O_3Si \cdot 0.6\ H_2O$: C, 63.71; H, 6.15. Found: C, 63.76; H, 6.23.

Example 2

3-[4-[3-[N-[2-Bis-(4-chlorophenyl)ethyl]-N-methylamino]propyl]phenoxy]-1-(4-carboxyphenoxy)-2-propanone

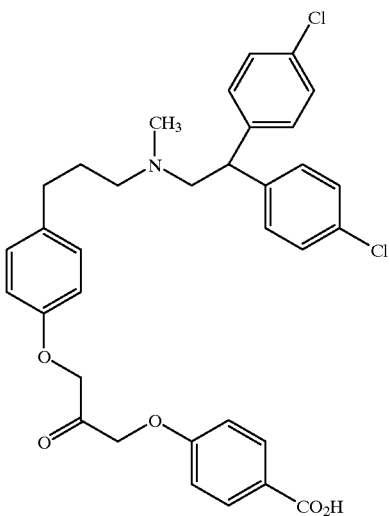

3-[4-[3-(tert-Butyldiphenylsilyloxy)propyl]phenoxy]-1-[4-(tert-butoxy carbonyl)phenoxy]-2-propanol

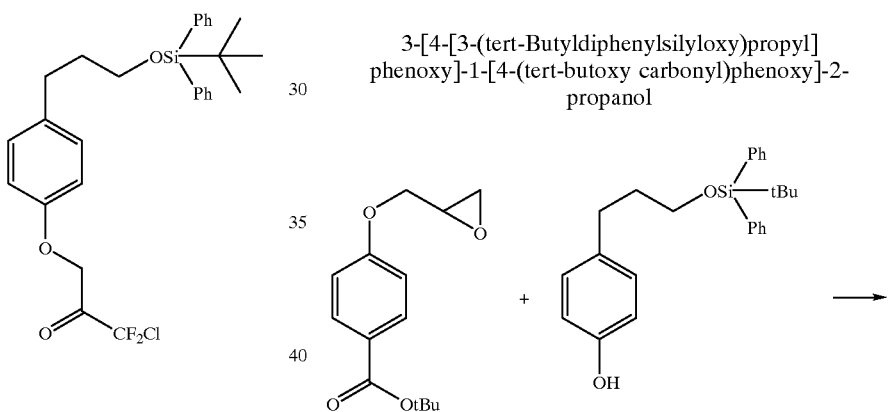

A mixture of 1,2-epoxy-3-[4-(tert-butoxycarbonyl)phenoxy]propane (5.11 g, 20.4 mmol) [S. P. Connors, et al., J. Med. Chem., 1991, 34, 1570] and 3-(4-hydroxyphenyl)-1-(tert-butyldiphenylsilyloxy)propane (7.97 g, 20.4 mmol) in N,N-dimethylformamide (50 ml) was treated with 1,4-diazabicyclo[2,2,2]octane (0.45 g) and the resulting mixture was heated at 70° C. for 48 hours. The cooled mixture was diluted with ethyl acetate, washed with water, saturated sodium bicarbonate and dried (magnesium sulfate). Evaporation of the solvent and chromatography of the residue on silica gel (elution toluene-ethyl acetate, 95:5) gave 7.67 g (58%) of the title material as oil.

Anal. Calcd. for $C_{39}H_{48}O_6Si$: C, 73.09; H, 7.55. Found: C, 73.01; H, 7.47.

3-[4-[3-(tert-Butyldiphenylsilyloxy)propyl]phenoxy]-1-[4-(tert-butoxycarbonyl)phenoxy]-2-propanone

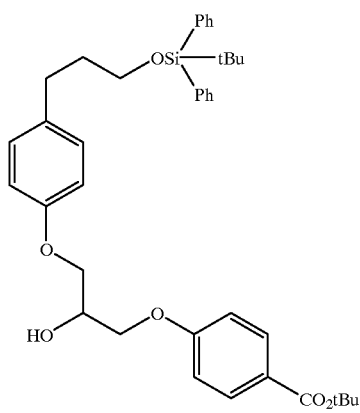

A solution of 3-[4-[3-(tert-butyldiphenylsilyloxy)propyl]phenoxy]-1-[4-(tert-butoxy carbonyl)phenoxy]-2-propanol (2.08 g, 3.25 mmol) in dichloromethane (120 ml) was treated with 1,1,1-triacetoxy-1,1-dihydro-1,2-benziodoxol-3(1H)-one (Dess-Martin periodinane) (5.46 g, 12.9 mmol) and the resulting mixture was stirred at 22° C. for 18 hours. The reaction mixture was then diluted with ethyl acetate, washed with 10% aqueous sodium thiosulfate, saturated sodium bicarbonate, brine and dried (magnesium sulfate). Evaporation of the solvent and chromatography of the residue on silica gel (elution toluene-ethyl acetate, 95:5) gave 1.82 g (88%) of the title material as oil.

Anal. Calcd. for $C_{39}H_{46}O_6Si$: C, 73.32; H, 7.26. Found: C, 73.36; H, 7.19.

3-[4-(3-Hydroxypropyl)phenoxy]-1-[4-(tert-butoxycarbonyl)phenoxy]-2-propanone

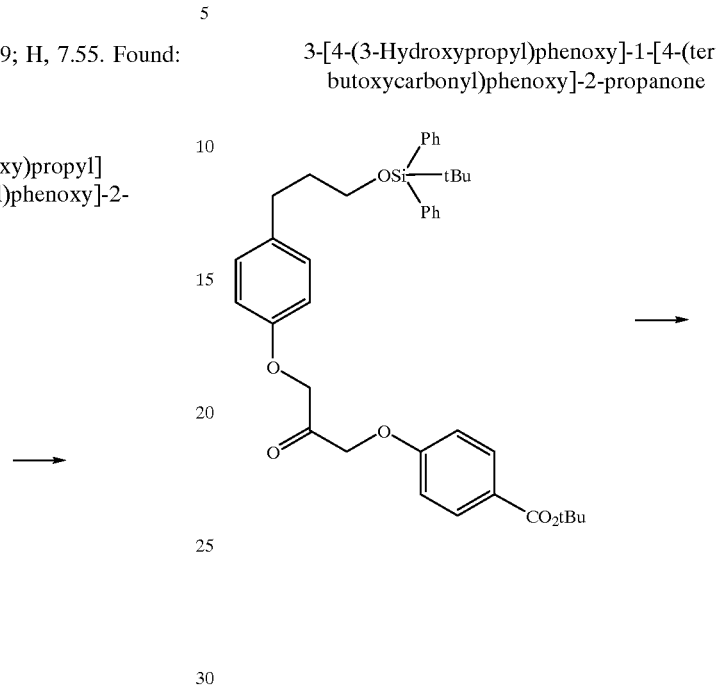

A solution of methyl 3-[4-[3-(tert-butyldiphenylsilyloxy)propyl]phenoxy]-1-[4-(tert-butoxycarbonyl)phenoxy]-2-propanone (1.44 g, 2.25 mmol) in tetrahydrofuran (35 ml) was treated at 22° C. with acetic acid (0.8 ml) followed by 5 ml (5 mmol) of a 1M solution of tetrabutylammonium fluoride in tetrahydrofuran. The mixture was then heated at 70° C. for 4 hours. The cooled reaction mixture was then diluted with ethyl acetate, washed with water, saturated sodium bicarbonate, brine and dried (magnesium sulfate). Evaporation of the solvent and chromatography of the residue on silica gel (elution toluene-ethyl acetate, 7:3) gave 0.88 g (97%) of the title material as oil.

Anal. Calcd. for $C_{23}H_{28}O_6$: C, 68.98; H, 7.05. Found: C, 69.34; H, 6.70.

37

3-[4-(3-Methanesulfonyloxypropyl)phenoxy]-1-[4-(tert-butoxycarbonyl)phenoxy]-2-propanone

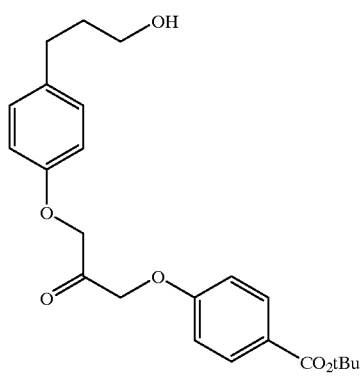

38

3-[4-[3-[N-[2-Bis-(4-chlorophenyl)ethyl]-N-methylamino]propyl]phenoxy]-1-[4-(tert-butoxycarbonyl)phenoxy]-2-propanone

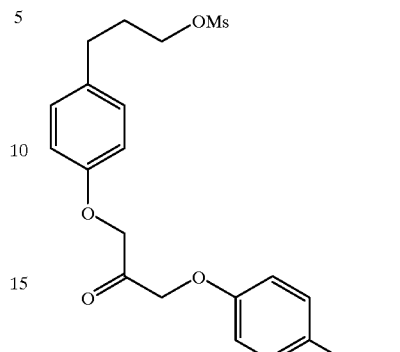

+

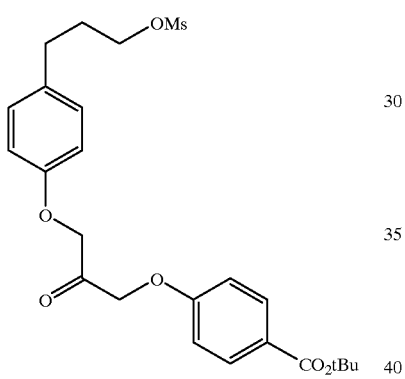

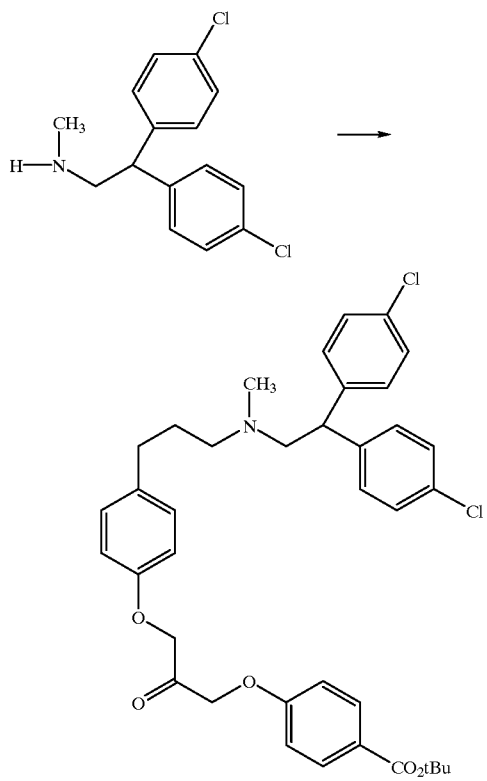

A solution of 3-[4-(3-hydroxypropyl)phenoxy]-1-[4-(tert-butoxycarbonly)phenoxy]-2-propanone (0.70 g, 0.75 mmol) in dichloromethane (10 ml) was cooled to 0° C. and treated with triethylamine (0.51 ml, 3.66 mmol) followed by methanesulfonyl chloride (0.23 ml, 2.97 mmol) added dropwise over 5 minutes. After 1 hour at 0° C., the reaction mixture was quenched by the addition of water and ethyl acetate. The organic phase was washed with water, brine and dried (magnesium sulfate). Evaporation of the solvent and chromatography of the residue on silica gel (elution toluene-ethyl acetate, 8:2) gave 0.66 g, (79%) of the title material as oil.

Anal. Calcd. for $C_{24}H_{30}O_8S \cdot 0.3\ H_2O$: C, 59.56; H, 6.37; S, 6.63. Found: C, 59.54; H, 6.35; S, 7.07.

A mixture of 3-[4-(3-methanesulfonyloxypropyl)phenoxy]-1-[4-(tert-butoxycarbonyl)phenoxy]-2-propanone (0.520 g, 1.09 mmol), N-methyl-2-bis-(4-chlorophenyl)ethylamine [Maryanoff, et al., *J. Med. Chem.* (1984) 27, 1067–1071] (0.76 g, 2.71 mmol) and sodium iodide (0.012 g) in acetonitrile (10 ml) was heated at 70° C. for 20 hours. The cooled mixture was diluted with ethyl acetate, washed with saturated sodium bicarbonate, brine and dried (magnesium sulfate). Evaporation of the solvent and chromatography of the residue on silica gel (elution toluene-ethyl acetate, 8:2) gave 0.57 g (79%) of the title material as syrup.

Anal. Calcd. for $C_{38}H_{41}Cl_2NO_5 \cdot 0.7\ H_2O$: C, 67.59; H, 6.33; N, 2.07. Found: C, 67.59; H, 6.25; N, 2.10.

3-[4-[3-[N-[2-Bis-(4-chlorophenyl)ethyl]-N-methylamino]propyl]phenoxy]-1-(4-carboxyphenoxy)-2-propanone

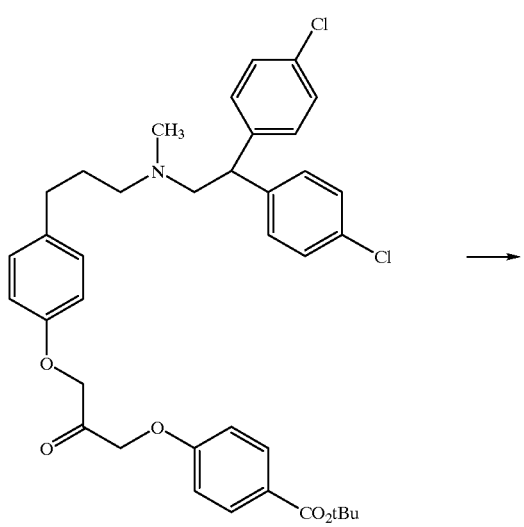

3-[4-[3-[N-[2-Bis-(4-chlorophenyl)ethyl]-N-methylamino]propyl]phenoxy]-1-[4-(tert-butoxycarbonyl)phenoxy]-2-propanone (2.51 g, 3.79 mmol) was dissolved in 15 ml of 1M solution of hydrogen chloride in acetic acid and the resulting mixture was stirred at 22° C. for 1.5 hours. The solvent was then evaporated in vacuo and a mixture of water and dichloromethane was added. The pH of the aqueous phase was adjusted to 4.5 with diluted sodium hydroxide and the two phases were stirred for 5 minutes. The organic phase was collected, washed with brine and dried (magnesium sulfate). Evaporation of the solvent and chromatography of the residue on silica gel (elution ethyl acetate-methanol 0–5%) gave 1.29 g (56%) of the title material as oil. The hydrochloride salt was prepared and obtained as a foam.

Anal. Calcd. for $C_{34}H_{33}Cl_2NO_5 \cdot HCl \cdot H_2O$: C, 61.78; H, 5.49; N, 2.12. Found: C, 61.85; H, 5.21; N, 2.15.

Example 3

(3R and 3S)-3-[4-[3-[N-[2-Bis-(4-chlorophenyl)ethyl]-N-methylamino]propyl]phenoxy]-1-(4-carboxyphenoxy)-2-butanone

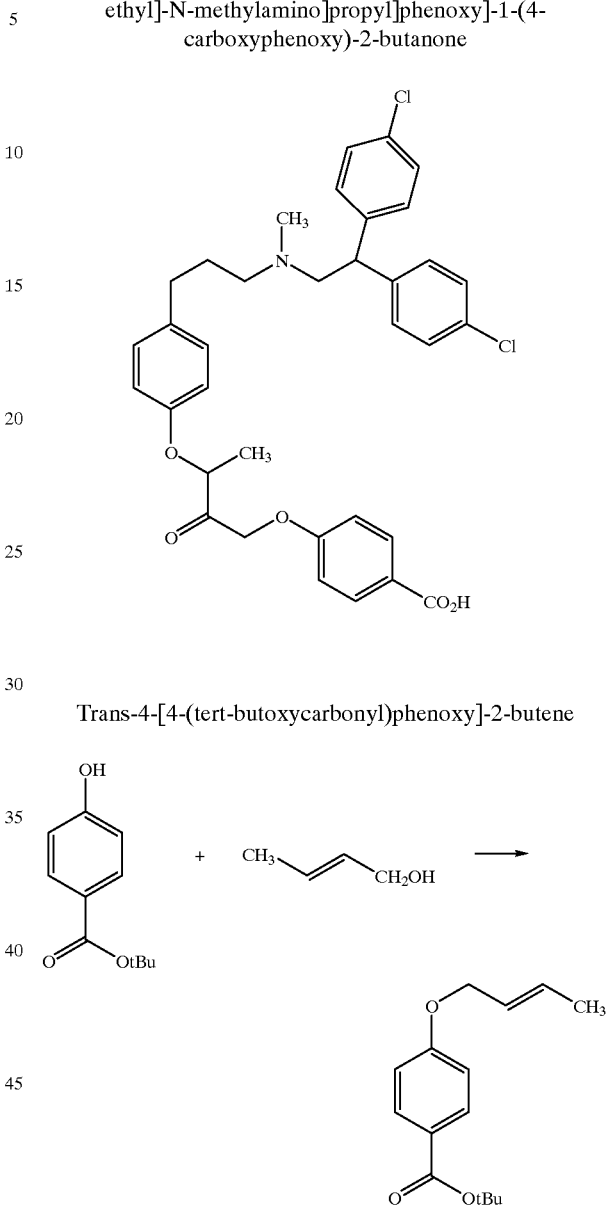

Trans-4-[4-(tert-butoxycarbonyl)phenoxy]-2-butene

A solution of 1,1-dimethylethyl 4-hydroxybenzoate (3.68 g, 18.9 mol) and 2-buten-1-ol (1.37 g, 18.9 mol) in dry benzene (100 ml) at 22° C. was treated with triphenylphosphine (5.48 g, 20.9 mmol) followed by a solution of diisopropyl azodicarboxylate (4.22 g, 20.9 mmol) in dry benzene (10 ml) added dropwise over 7 minutes. After 3 hours at 22° C., the solvent was concentrated under reduced pressure and the residue was chromatographed on silica gel. Elution with a mixture of toluene and ethyl acetate (99:1) gave 3.70 g (79%) of the title material as a clear oil: bp 85–90° C./0.1 torr (bulb to bulb, air bath temperature).

Anal. Calcd. for $C_{15}H_{20}O_3$: C, 72.55; H, 8.12. Found: C, 72.44; H, 8.27.

2,3-Epoxy-4-[4-(tert-butoxycarbonyl)phenoxy] butane

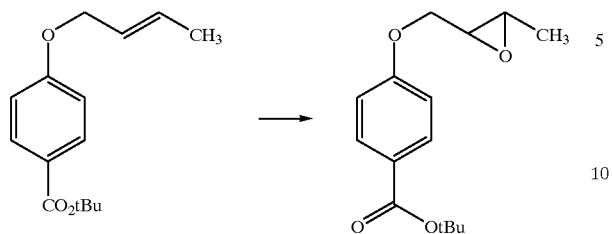

A solution of trans-4-[4-(tert-butoxycarbonyl)phenoxy]-2-butene (3.10 g, 12.48 mmol) in dry dichloromethane (50 ml) was treated at 22° C. with 3-chloroperoxybenzoic acid (4.30 g, 24.9 mmol) and the resulting mixture was stirred at 22° C. for 18 hours. The mixture was then diluted with toluene, washed with 5% sodium thiosulfate, saturated sodium bicarbonate and brine. After drying (sodium sulfate), evaporation of the solvent gave an oil that was chromatographed on silica gel. Elution with a mixture of toluene and ethyl acetate (95:5) gave 3.16 g (96%) of the title material as an oil which solidified upon standing: bp 85–90° C./0.05 torr (bulb to bulb, air bath temperature); mp 47–48° C.

Anal. Calcd. for $C_{15}H_{20}O_4$: C, 68.16; H, 7.63. Found: C, 67.91; H, 7.30.

Erythro-3-[4-(3-tert-butyldiphenylsilyloxy)propyl]phenoxy]-1-[4-(tert-butoxycarbonyl)phenoxy]-2-butanol

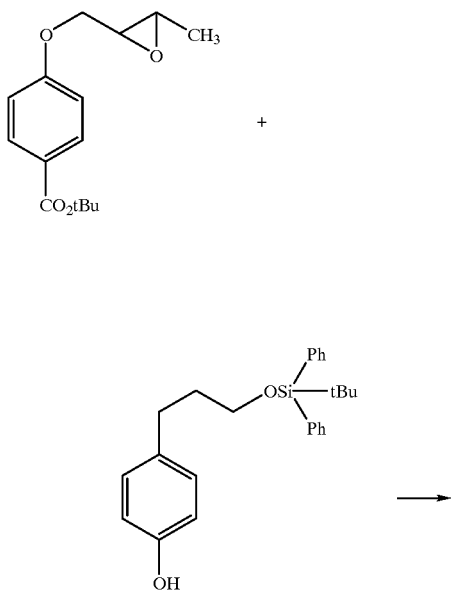

A mixture of 2,3-epoxy-4-[4-(tert-butoxycarbonyl)phenoxy]butane (0.656 g, 2.48 mmol) and 3-(4-hydroxyphenyl)-1-(tert-butyldiphenylsilyloxy) propane (0.970 g, 2.48 mmol) in dry N,N-dimethylformamide (10 ml) was treated with 1,4-diazabicyclo[2,2,2]octane (0.060 g) and the resulting mixture was stirred at 70° C. for 72 hours. The reaction mixture was then diluted with ethyl acetate, washed with water, saturated sodium bicarbonate and brine. After drying (anhydrous magnesium sulfate), evaporation of the solvent gave an oil that was chromatographed on silica gel. Elution with a mixture of toluene and ethyl acetate (98:5) gave 0.206 g (12%) of the title material as an oil.

Anal. Calcd. for $C_{40}H_{50}O_6Si$: C, 73.36; H, 7.70. Found: C, 73.42; H, 7.64.

(3R and 3S)-3-[4-[3-tert-Butyldiphenylsilyloxy)propyl]phenoxy]-1-[4-(tert-butoxycarbonyl)phenoxy]-2-butanone

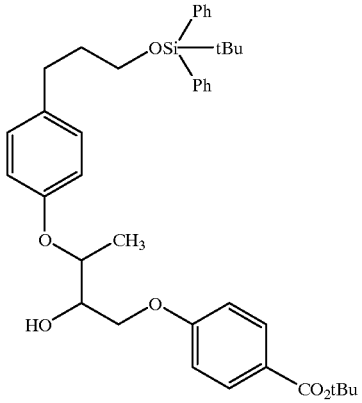

A solution of erythro-3-[4-(3-tert-butyldiphenylsilyloxy)propyl]phenoxy]-1-[4-(tert-butoxycarbonyl)phenoxy]-2-butanol (0.150 g, 0.23 mmol) in dry dichloromethane (10 ml) was treated with 1,1,1-triacetoxy-1,1-dihydro-1,2-benziodoxol-3(1H)-one (Dess-Martin periodinane) (0.38 g, 0.91 mol) and the resulting mixture was stirred at 22° C. for 18 hours. The reaction mixture was then diluted with ethyl acetate, washed with 5% sodium thiosulfate, saturated sodium bicarbonate and brine. After drying (anhydrous sodium sulfate), evaporation of the solvent gave an oil that was chromatographed on silica gel. Elution with a mixture of toluene and ethyl acetate (95:5) gave 0.130 g (87%) of the title material as an oil.

Anal. Calcd. for $C_{40}H_{48}O_6Si$: C, 72.98; H, 7.44. Found: C, 72.96; H, 7.67.

(3R and 3S)-3-[4-(3-Hydroxypropyl)phenoxy]-1-[4-(tert-butoxycarbonyl)phenoxy]-2-butanone

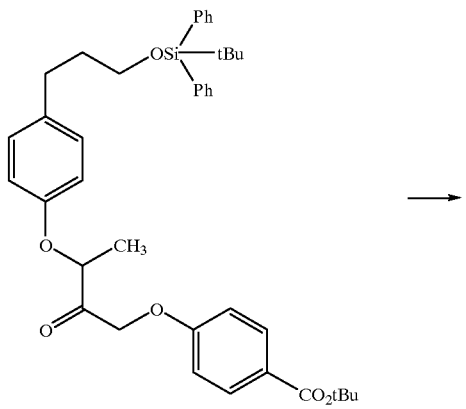

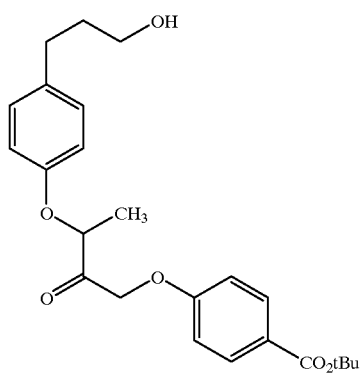

A solution of (3R and 3S)-3-[4-[3-(tert-butyldiphenylsilyloxy)propyl]phenoxy]-1-[4-(tert-butoxycarbonyl)phenoxy]-2-butanone (0.314 g, 0.48 mmol) in tetrahydrofuran (10 ml) was treated with acetic acid (0.7 ml) followed with 1M tetrabutylammonium fluoride in tetrahydrofuran (1.1 ml, 1.1 mmol). The resulting mixture was then heated at 70° C. for 3.5 hours. The cooled mixture was diluted with ethyl acetate, washed with saturated sodium bicarbonate, brine and dried (magnesium sulfate). Evaporation of the solvent and chromatography of the residue on silica gel (elution toluene-ethyl acetate, 8:2) gave 0.106 g (53%) of the title material as a syrup.

$^1$H NMR 400 MHz (CDCl$_3$) δ (ppm): 1.58 (9H, s, t-Bu), 1.61 (3H, d, J=7.2 Hz, CH$_3$), 1.89, (2H, m, CH$_2$), 2.69 (2H, m, CH$_2$), 3.68 (2H, m, CH$_2$O), 4.9 and 5.13 (2×1H, 2d, J=17.8 Hz, OCH$_2$), 4.91 (1H, m, CH), 6.81 and 7.91 (2×2H, 2d, J=8.9 Hz, aromatics) and 6.86 and 7.16 (2×2H, 2d, J=8.62 Hz, aromatics).

MS (ESI$^+$) (m/z): 415 (MH$^+$).

(3R and 3S)-3-[4-(3-Methanesulfonyloxypropyl) phenoxy]-1-[4-(tert-butoxycarbonyl)phenoxy]-2-butanone

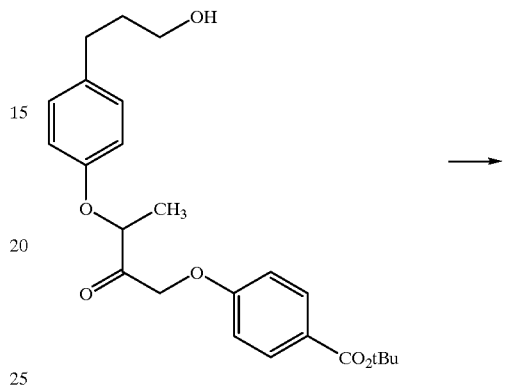

A solution of (3R and 3S)-3-[4-(3-hydroxypropyl) phenoxy]-1-[4-(tert-butoxycarbonyl)phenoxy]-2-butanone (0.092 g, 0.22 mmol) in dry dichloromethane (5 ml) was cooled to 0° C. and treated with triethylamine (0.07 ml, 0.5 mmol) followed by methanesulfonyl chloride (0.03 ml, 0.39 mmol). After 45 minutes at 0° C., the reaction mixture was quenched by addition of ethyl acetate (100 ml) and water. The organic phase was washed with saturated sodium bicarbonate, brine and dried (magnesium sulfate). Evaporation and chromatography of the residue on silica gel (elution toluene and ethyl acetate, 9:1) gave 0.090 g (82%) of the title material as an oil.

$^1$H NMR 400 MHz (CDCl$_3$) δ (ppm): 1.58 (9H, s, t-Bu), 1.61 (3H, d, J=7.3 Hz, CH$_3$), 2.06 (2H, m, CH$_2$), 2.72 (2H, m, CH$_2$), 3.02 (3H, s, OMs), 4.24 (2H, t, J=6.1 Hz, CH$_2$O), 4.90 and 5.13 (2×1H, 2d, J=18.2 Hz, OCH$_2$), 4.92 (1H, q, J=7.3 Hz, CH), 6.84 and 7.92 (2×2H, 2d, J=8.6 Hz, aromatics), 6.86 and 7.15 (2×2H, 2d, J=8.6 Hz, aromatics).

MS (ESI$^+$) (m/z): 510 (M+NH$_4^+$).

(3R and 3S)-3-[4-[3-[N-[2-Bis-(4-chlorophenyl) ethyl]-N-methylamino]propyl]phenoxy]-1-[4-(tert-butoxycarbonyl)phenoxy]-2-butanone

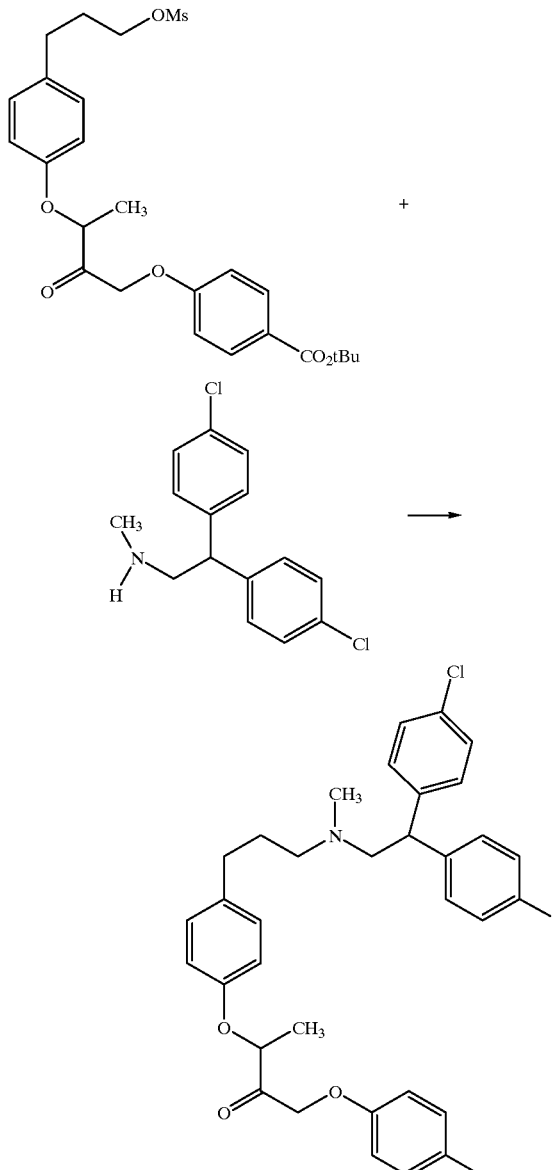

A solution of (3R and 3S)-3-[4-(3-methanesulfonyloxypropyl)phenoxy]-1-[4-(tert-butoxycarbonyl)phenoxy]-2-butanone (0.080 g, 0.162 mmol) and N-methyl-2-bis-(4-chlorophenyl)ethylamine (0.050 g, 0.178 mml) in acetonitrile (5 ml) was treated with N,N-diisopropylethylamine (0.035 ml) and sodium iodide (0.005 g) and the resulting mixture was stirred at 80° C. for 16 hours. The cooled mixture was diluted with ethyl acetate, washed with saturated sodium bicarbonate, brine and dried (magnesium sulfate). Evaporation of the solvent and chromatography of the residue on silica gel (elution toluene and ethyl acetate, 85:15) gave 0.096 g (87%) of the title material as a syrup.

$^1$H NMR 400 MHz ($C_6D_6$) δ (ppm): 1.19 (2H, d, J=7.3 Hz, $CH_3$), 1.49 (9H, s, t-Bu), 1.56 (2H, m, $CH_2$), 2.02 (3H, s, $NCH_3$), 2.19 (2H, t, J=6.9 Hz, $CH_2$) 2.35 (2H, t, J=8.1 Hz, $CH_2$), 2.58 (2H, d, J=7.7 Hz, $NCH_2$), 3.81 (1H, t, J=7.7 Hz, CH), 4.47 and 4.61 (2×1H, 2d, J=17.4 Hz, $OCH_2$), 4.51 (1H, q, J=7.3 Hz, CH), 6.63 and 6.87 (2×2H, 2d, J=8.5 Hz, aromatics), 6.73 and 8.68 (2×2H, 2d, J=8.7 Hz, aromatics), 6.79 and 7.14 (2×4H, 2d, J=8.0 Hz, aromatics).

MS (ESI) (m/z$^+$): 676 (MH$^+$).

(3R and 3S)-3-[4-[3-[N-[2-Bis-(4-chlorophenyl) ethyl]-N-methylamino]propyl)phenoxy]-1-(4-carboxyphenoxy)-2-butanone

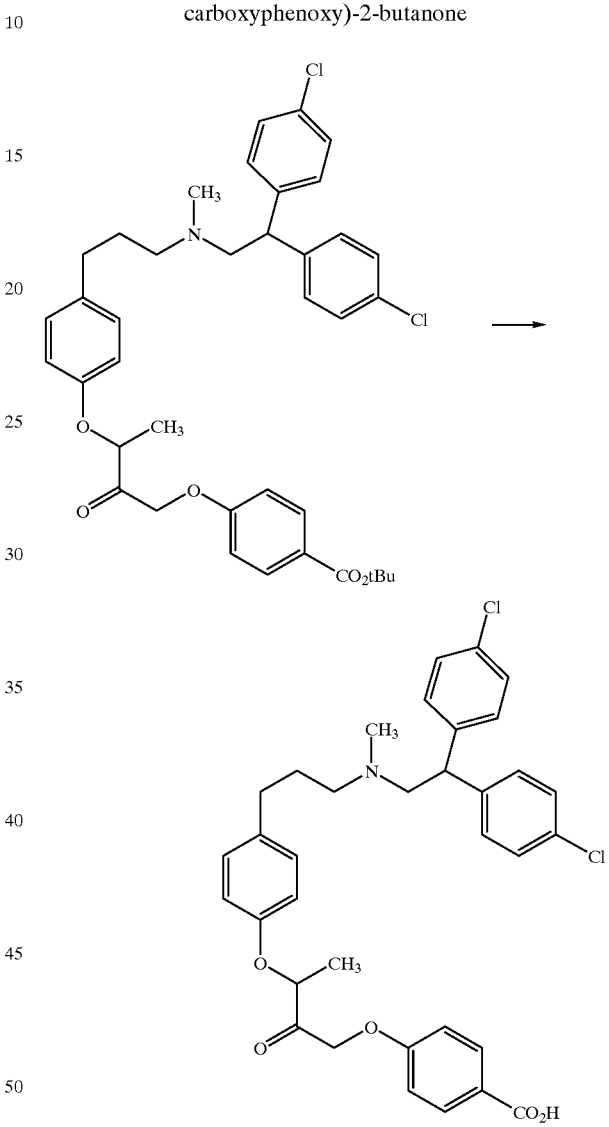

(3R and 3S)-3-[4-[3-[N-[2-Bis-(4-chlorophenyl)ethyl]-N-methylamino]propyl]phenoxy]-1-[4-(tert-butoxycarbonyl) phenoxy]-2-butanone (0.084 g, 0.12 mmol) was treated at 22° C. with 2 ml of 1M hydrochloric acid in acetic acid. After 1.5 hours, the solvent was evaporated in vacuo and the residue was partitioned between dichloromethane (10 ml) and water (10 ml). The pH of the aqueous phase was adjusted to 4.5 with 0.1N sodium hydroxide and the aqueous phase was extracted twice with dichloromethane. The combined organic extracts were dried (magnesium sulfate) and concentrated. Chromatography of the residue on silica gel (elution ethyl acetate-methanol, 0–20%) gave 0.032 g (41%) of the title material as a foam. The hydrochloride salt was prepared and obtained as an amorphous solid.

Hydrochloride salt: $^1$H NMR 400 MHz (DMSO-d$_6$) δ (ppm): 1.5 (3H, d, J=6.8, Hz, CH$_3$), 1.9 (2H, m, CH$_2$), 2.74 (3H, s, NCH$_3$), 2.95–3.07 (2H, m, CH$_2$), 3.76–4.03 (2H, m, CH$_2$), 4.66 (1H, broad t, J=7.3 Hz, CH), 5.14 and 5.37 (2×1H, 2d, J=18.3 Hz, OCH$_2$), 5.18 (1H, q, J=6.8 Hz, CH), 6.92 and 7.12 (2×2H, 2d, J=8.5 Hz, aromatics), 6.96 and 7.86 (2×2H, 2d, J=8.8 Hz, aromatics) and 7.4–7.5 (8H, m, aromatics).

MS (ESI$^+$) m/z: 620 (MH$^+$).

Example 4

(3R and 3S)-1-[4-[3-[N-[2-Bis-(4-chlorophenyl)ethyl]-N-methylamino]propyl]phenoxy]-3-(4-carboxyphenoxy)-2-butanone

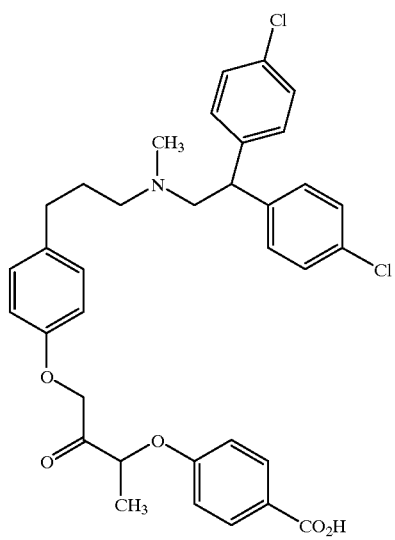

(3R and 3S)-3-[4-(tert-Butoxycarbonyl)phenoxy]-1-butene

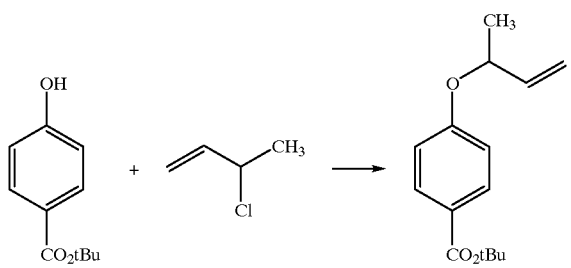

A solution of 1,1-dimethylethyl 4-hydroxybenzoate (5.0 g, 25.7 mmol) in N,N-dimethylformamide (35 ml) was treated with a solution of sodium hydroxide (1.14 g, 35.1 mmol) in water (2 mL). Then 3-chloro-1-butene (3.06 g, 33.8 mmol) was added and the resulting mixture was heated at 45° C. for 5 hours. The cooled mixture was diluted with toluene, washed with water, dried (magnesium sulfate) and concentrated under reduced pressure. Chromatography of the residue on silica gel (elution toluene-hexane, 1:1) gave 3.84 g (60%) of the title material as a clear oil.

$^1$H NMR 400 MHz (CDCl$_3$) δ (ppm): 1.47 (3H, d, J=6.4 Hz, CH$_3$), 1.59 (9H, s, t-Bu), 4.98 (1H, m, CH), 5.2–5.3 (2H, m, olefinic C—H), 5.85–5.95 (1H, m, olefinic C—H), 6.90 and 7.92 (2×2H, 2d, J=8.9 H, aromatic).

Anal. Calcd. for C$_{15}$H$_{20}$O$_3$: C, 72.55; H, 8.12. Found: C, 72.30; H, 8.17.

(2R, 2S and 3R, 3S)-1,2-Epoxy-3-[4-(tert-butoxycarbonyl)phenoxy]-butane

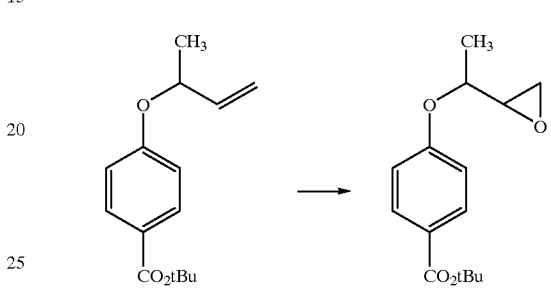

A solution of (3R and 3S)-3-[4-(tert-butoxycarbonyl)phenoxy]-1-butene (3.78 g, 15.2 mmol) in dry dichloromethane (50 ml) was treated at 22° C. with 3-chloroperoxybenzoic acid (4.8 g, 28.0 mmol) and the resulting mixture was stirred for 140 hours. The mixture was then diluted with toluene, washed with 5% sodium thiosulfate, sodium bicarbonate and dried (magnesium sulfate). Evaporation of the solvent and chromatography of the residue on silica gel (elution toluene-ethyl acetate 2%) gave 3.53 g (87%) of the title material as an oil. $^1$H NMR indicated a 6:4 diastereoisomeric mixture which was used as such for the next step.

(2R, 2S and 3R, 3S)-1-[4-[3-tert-Butyldiphenylsilyloxy)propyl]phenoxy]-3-[4-(tert-butoxycarbonyl)phenoxy]-2-butanol

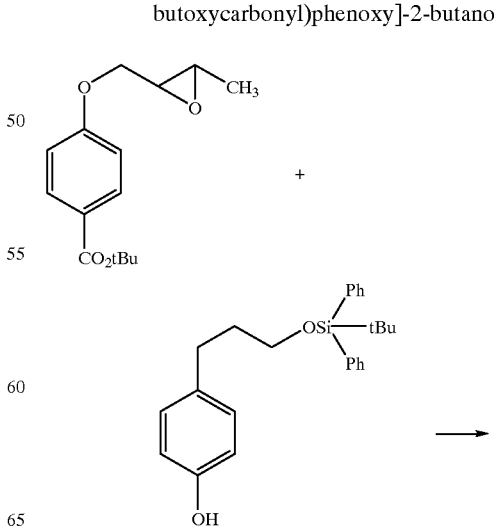

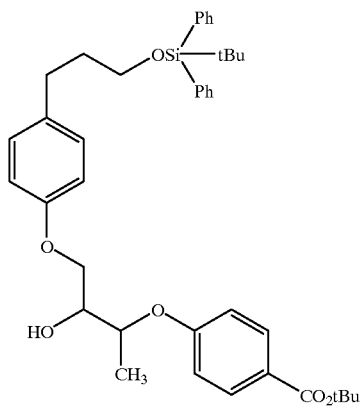

A solution of (2R, 2S and 3R, 3S)-1,2-epoxy-3-[4-(tert-butoxycarbonyl)phenoxy]-butane (3.46 g, 13.1 mmol) and 3-(4-hydroxyphenyl)-1-(tert-butyldiphenylsilyloxy) propane (5.11 g, 13.1 mmol) in dry N,N-dimethylformamide (35 ml) was treated with 1,4-diazabicyclo[2,2,2]octane (0.4 g) and the resulting mixture was heated at 80° C. for 36 hours. The reaction mixture was then diluted with ethyl acetate, washed with water, saturated sodium bicarbonate and brine. After drying (anhydrous magnesium sulfate), evaporation of the solvent gave an oil that was chromatographed on silica gel. Elution with a mixture of hexane and ethyl acetate (85:15) gave 3.27 g (38%) of the title material as an oil. $^1$H NMR indicated a 6:4 diastereoisomeric mixture that was used as such for the next step.

(3R and 3S)-1-[4-[3-tert-Butyldiphenylsilyloxy) propyl]phenoxy]-3-[4-(tert-butoxycarbonyl) phenoxy]-2-butanone

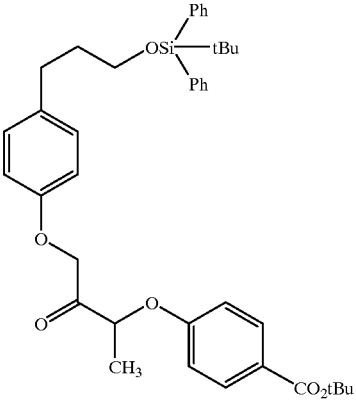

A solution of (2R, 2S and 3R, 3S)-1-[4-[3-tert-butyldiphenylsilyloxy)propyl]phenoxy]-3-[4-(tert-butoxycarbonyl)phenoxy]-2-butanol (3.22 g, 4.9 mmol) in dry dichloromethane (180 ml) was treated with 1,1,1-triacetoxy-1,1-dihydro-1,2-benziodoxol-3(1H)-one (Dess-Martin periodinane) (8.27 g, 19.5 mol) and the resulting mixture was stirred at 22° C. for 16 hours. The reaction mixture was then washed with 5% sodium thiosulfate, saturated sodium bicarbonate and brine. After drying (magnesium sulfate), evaporation of the solvent gave an oil that was chromatographed on silica gel. Elution with a mixture of toluene and ethyl acetate (95:5) gave 3.10 g (96%) of the title material as an oil.

$^1$H NMR 400 MHz (CDCl$_3$) δ (ppm): 1.07 (9H, s, Sit-Bu), 1.59 (9H, s, t-Bu), 1.64 (3H, d, J=7.3 Hz, CH$_3$), 1.83 (2H, m, CH$_2$), 2.66 (2H, m, CH$_2$), 3.68 (3H, t, J=6.05 Hz, OCH$_2$), 4.76 and 4.98 (2×1H, 2d, J=17.7 Hz, OCH$_2$), 4.76 and 4.98 (2×1H, 2d, J=17.7 Hz, OCH$_2$), 5.09 (1H, q, J=7.3 H, CH), 6.78 (2H, d, J=8.6 Hz, aromatic), 6.90 (2H, d, J=8.6 Hz, aromatic), 7.08 (2H, d, J=8.6 Hz, aromatic), 7.42 (6H, m, aromatic), 7.68 (4H, m, aromatic) and 7.96 (2H, d, J=8.6 Hz, aromatic).

Anal. Calcd. for C$_{40}$H$_{48}$O$_6$Si: C, 73.59; H, 7.41. Found: C, 73.25; H, 7.50.

(3R and 3S)-1-[4-(3-Hydroxypropyl)phenoxy]-3-[4-(tert-butoxycarbonyl)phenoxy]-2-butanone

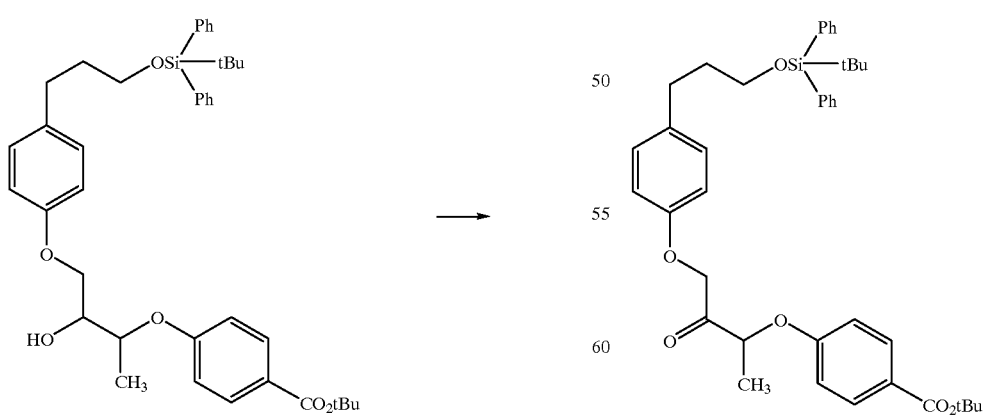

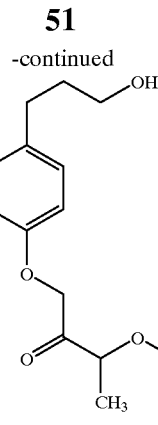

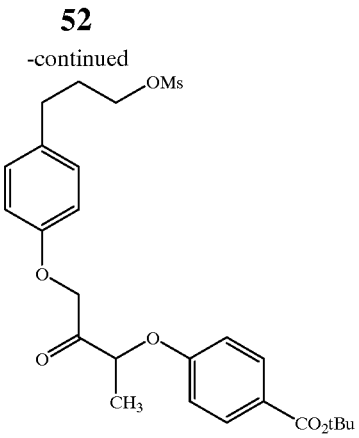

A solution of (3R and 3S)-1-[4-[3-(tert-butyldiphenylsilyloxy)propyl]phenoxy]-3-[4-(tert-butoxycarbonyl)phenoxy]-2-butanone (2.82 g, 4.32 mmol) in tetrahydrofuran (70 ml) was treated with acetic acid (1.5 ml) followed by 1M tetrabutylammonium fluoride in tetrahydrofuran (10 ml, 10.0 mmol). The mixture was then heated at 70° C. for 3.5 hours. The cooled mixture was then diluted with ethyl acetate, washed with saturated sodium bicarbonate, brine and dried (magnesium sulfate). Evaporation of the solvent and chromatography of the residue on silica gel (elution toluene-ethyl acetate 8:2) gave 1.64 g (91%) of the title material as an oil.

$^1$H NMR 400 MHz (CDCl$_3$) δ (ppm): 1.59 (9H, s, t-Bu), 1.64 (2H, d, J=7.3 Hz, CH$_3$), 1.87, (2H, m, CH$_2$), 2.67 (2H, t, J=7.7 Hz, CH$_2$), 3.67 (2H, t, J=6.3 Hz, OCH$_2$), 4.77 and 4.98 (2×1H, 2d, J=17.7 Hz, OCH$_2$), 5.08 (1H, q, J=7.3 Hz, CH), 6.80 (2H, d, J=8.7 Hz, aromatic) 6.88 (2H, d, J=8.5 Hz, aromatic), 7.12 (2H, d, J=8.7 Hz, aromatic) and 7.95 (2H, d, J=8.5 Hz, aromatic).

Anal. Calcd. for C$_{24}$H$_{30}$O$_6$·0.3H$_2$O: C, 68.65; H, 7.35. Found: C, 68.60; H, 7.27.

A solution of (3R and 3S)-1-[4-(3-hydroxypropyl)phenoxy]-3-[4-(tert-butoxycarbonyl)phenoxy]-2-butanone (1.57 g, 3.8 mmol) in dry dichloromethane (25 ml) was cooled to 0–50° C. and treated with triethylamine (1.1 ml, 7.9 mmol) followed by methanesulfonyl chloride (0.5 mL, 6.46 mmol) added dropwise over 2 minutes. After 45 minutes at 0–5° C., the reaction mixture was quenched by addition of ethyl acetate and saturated sodium bicarbonate. The organic phase was washed with brine and dried (anhydrous magnesium sulfate) and evaporated. Chromatography of the residual oil on silica gel (elution toluene-ethyl acetate, 9:1) gave 1.83 g (97%) of the title material as an oil.

$^1$H NMR 400 MHz (CDCl$_3$) δ (ppm): 1.59 (9H, s, t-Bu), 1.64 (3H, d, J=6.9 Hz, CH$_3$), 2.71 (2H, t, J=7.3 Hz, CH$_2$), 3.01 (3H, s, OMs), 4.22 (2H, t, J=6.04 Hz, OCH$_2$), 4.77 and 5.01 (2×1H, 2d, J=17.9 Hz, OCH$_2$), 5.07 (1H, q, J=6.9 Hz, CH), 6.81 (2H, d, J=8.7 Hz, aromatic), 6.90 (2H, d, J=8.5 Hz, aromatic), 7.11 (2H, d, J=8.7 Hz, aromatic) and 7.96 (2H, d, J=8.5 Hz, aromatic).

Anal. Calcd. for C$_{25}$H$_{32}$O$_8$S·H$_2$O: C, 58.81; H, 6.71; S, 6.28. Found: C, 58.80; H, 6.31; S, 6.01.

(3R and 3S)-1-[4-(3-Methanesulfonyloxypropyl)phenoxy]-3-[4-(tert-butoxycarbonyl)phenoxy]-2-butanone (3R and 3S)-1-[4-[3-[N-[2-Bis-(4-chlorophenyl)ethyl]-N-methylamino]propyl]phenoxy]-3-[4-(tert-butoxycarbonyl)phenoxy]-2-butanone

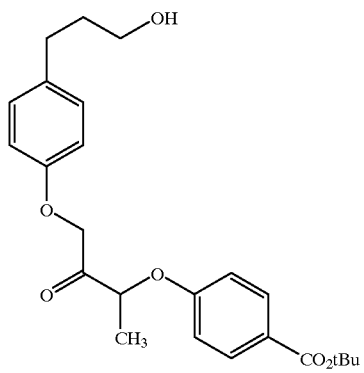  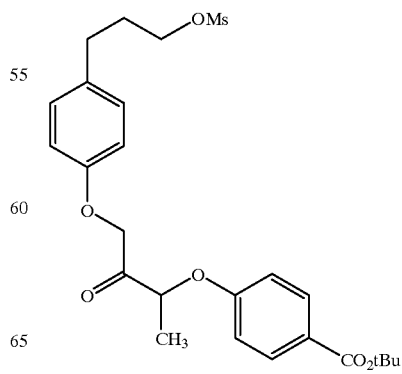

+

53
-continued

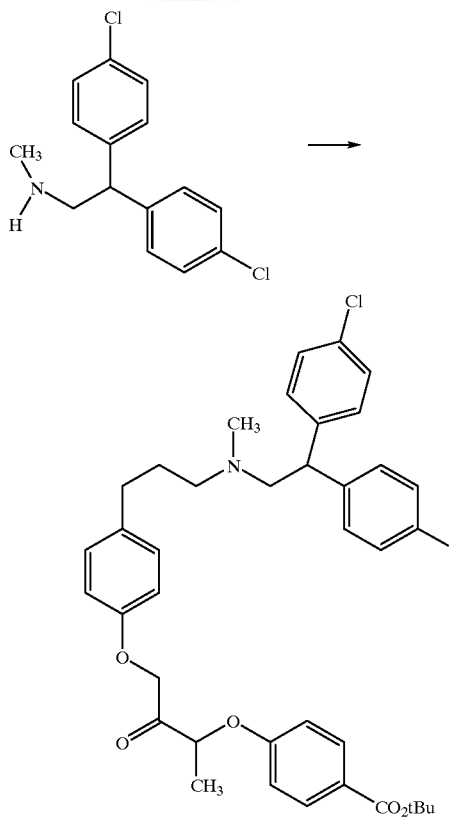

A solution of (3R and 3S)-1-[4-(3-methanesulfonyloxypropyl)phenoxy]-3-[4-tert-butoxycarbonyl)phenoxy]-2-butanone (1.67 g, 3.39 mmol) and N-methyl-2-bis-(4-chlorophenyl)ethylamine (0.98 g, 3.49 mml) in acetonitrile was treated with N,N-diisopropylethylamine (0.74 ml, 4.26 mol) and sodium iodide (0.040 g) and the resulting mixture was heated at 80° C. for 20 hours. The cooled mixture was diluted with ethyl acetate, washed with saturated sodium bicarbonate, brine and dried (magnesium sulfate). Evaporation of the solvent and chromatography of the residue on silica gel (elution toluene and ethyl acetate, 85:15) gave 1.85 g (90%) of the title material as a clear syrup.

$^1$H NMR 400 MHz ($C_6D_6$) δ (ppm): 1.16 (3H, d, J=6.4 Hz, $CH_3$), 1.50 (9H s, t-Bu), 1.55 (2H, m, $CH_2$), 2.01 (3H, s, $NCH_3$), 2.18 (2H, t, J=6.9 Hz, $CH_2$), 2.34 (2H, t, J=7.5 Hz, $CH_2$), 2.58 (2H, d, J=7.5 Hz, $CH_2$), 3.80 (1H, t, J=7.5 Hz, CH), 4.45 and 4.59 (2×1H, 2d, J=17.6 Hz, $OCH_2$), 4.53 (1H, q, J=6.4 Hz, CH), 6.61 (2H, 2d, J=8.7 Hz, aromatic), 6.77 (2H, d, J=9.0 Hz, aromatics), 6.79 (4H, J=8.6 Hz, aromatic), 6.87 (2H, d, J=8.7 Hz, aromatic), 7.14 (4H, d, J=8.6 Hz, aromatic) and 8.09 (2H, d, J=9.0 Hz, aromatic).

Anal. Calcd. for $C_{39}H_{43}Cl_2NO_5 \cdot 1.4H_2O$: C, 66.74; H, 6.58; S, 2.00. Found: C, 66.60; H, 6.84; S, 2.11.

54
(3R and 3S)-1-[4-[3-[N-[2-Bis-(4-chlorophenyl) ethyl]-N-methylamino]propyl]phenoxy]-3-(4-carboxyphenoxy)-2-butanone

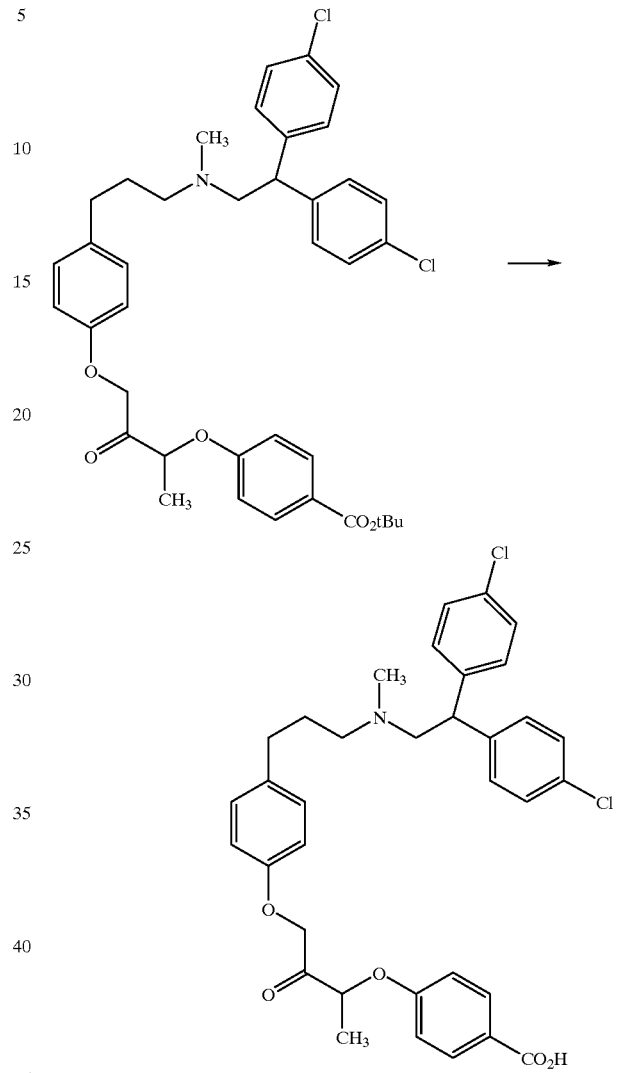

(3R and 4S)-1-[4-[3-[N-[2-Bis-(4-chlorophenyl)ethyl]-N-methylamino]propyl]phenoxy]-3-[4-(tert-butoxycarbonyl) phenoxy]-2-butanone (1.77 g, 2.62 mmol) was dissolved in 1M hydrochloric acid in acetic acid (15 ml) and the resulting mixture was stirred at 22° C. for 1.5 hours. The acetic acid was then evaporated and the residue was partitioned between dichloromethane and water. The pH of the aqueous phase was adjusted to 4.5 with 0.1N sodium hydroxide and the aqueous phase was extracted twice with dichloromethane. The combined organic extracts were dried (magnesium sulfate) and concentrated. Chromatography of the residue on silica gel (elution ethyl acetate-methanol 0–10%) gave 0.829 g (51%) of the title material as a foam. The hydrochloride salt was prepared and obtained as an amorphous solid.

Hydrochloride salt: $^1$H NMR 400 MHz (DMSO-$d_6$) δ (ppm): 1.53 (3H, d, J=6.55 Hz, $CH_3$), 1.9 (2H, m, $CH_2$), 2.73 (3H, broad, $NCH_3$), 3.05 (2H, m, $CH_2$), 3.78 and 3.98 (2×1H, 2m, $CH_2$), 4.64 (1H, t, J=7.3 Hz, CH), 5.03 and 5.23 (2×1H, 2d, J=18.4 Hz, $OCH_2$), 5.34 (1H, q, J=6.55 Hz, CH), 6.84 (2H, d, J=8.3 Hz, aromatic), 7.04 (2H, d, J=8.8 Hz, aromatic), 7.08 (2H, d, J=8.3 Hz, aromatic) 7.4 (8H, m, aromatic) and 7.86 (2H, d, J=8.8 Hz, aromatic).

Anal. Calcd. for $C_{35}H_{35}Cl_2NO_5 \cdot HCl \cdot H_2O$: C, 62.27; H, 5.67; S, 2.07. Found: C, 62.34; H, 5.57; S, 2.23.

Example 5

3-[4-[3-[N-[2-Bis-(4-chlorophenyl)ethyl]N-methylamino]propyl]phenoxy]-1-(4-carboxyphenoxy)-3-methyl-2-butanone

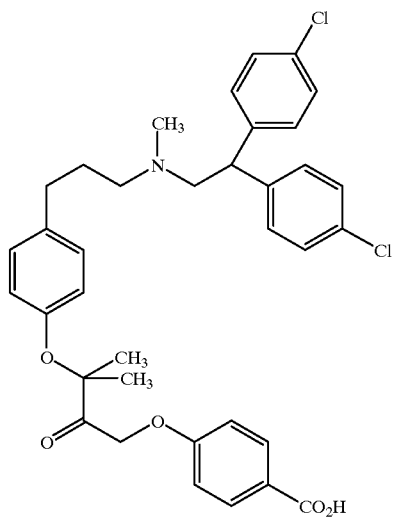

Methyl 2-[4-[3-(tert-butyldiphenylsilyloxy)propyl]phenoxy]-2-methyl propionate

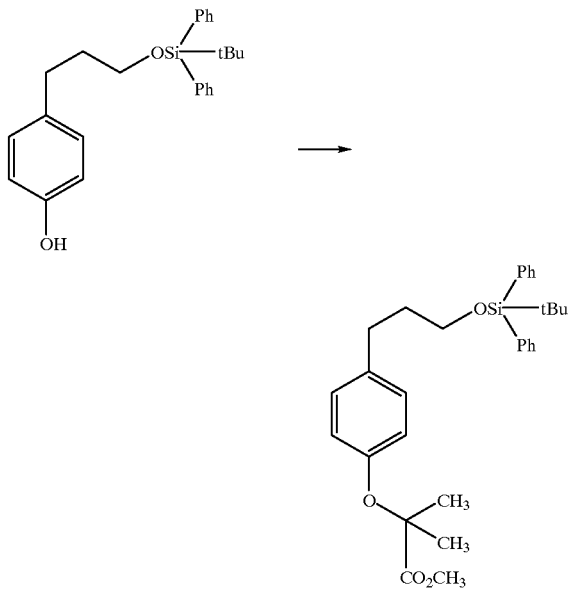

A solution of 3-(4-hydroxyphenyl)-1-(tert-butyldiphenylsilyloxy)propane (5.00 g, 12.8 mmol) and methyl 2-bromo-2-methylpropionate (4.53 g, 25.0 mmol) in dry acetonitrile (25 ml) was treated with cesium carbonate (8.3 g, 25.4 mmol) and the resulting mixture was heated at 60° C. for 3.5 hours. The cooled mixture was diluted with ethyl acetate, washed with water, brine and dried (magnesium sulfate). Evaporation of the solvent and chromatography of the residue on silica gel (elution toluene) gave 5.88 g (93%) of the title material as a clear oil.

$^1$H NMR 400 MHz (CDCl$_3$) δ (ppm): 1.08 (9H, s, t-Bu) 1.59 (6H, s, CH$_3$), 1.86 (2H, m, CH$_2$), 2.67 (2H, t, J=7.91 Hz, CH$_2$), 3.69 (2H, t, J=6.21 Hz, OCH$_2$), 3.80 (3H, s, OCH$_3$), 6.76 (2H, t, J=8.6 Hz, aromatic), 7.05 (2H, d, J=8.6 Hz, aromatic), 7.4 and 7.7 (6H and 4H, 2m, aromatic).

Anal. Calcd. for $C_{30}H_{38}O_4Si$: C, 73.43; H, 7.81. Found: C, 73.5; H, 7.96.

2-[4-[3-(tert-Butyldiphenylsilyloxy)propyl]phenoxy]-2-methylpropanol

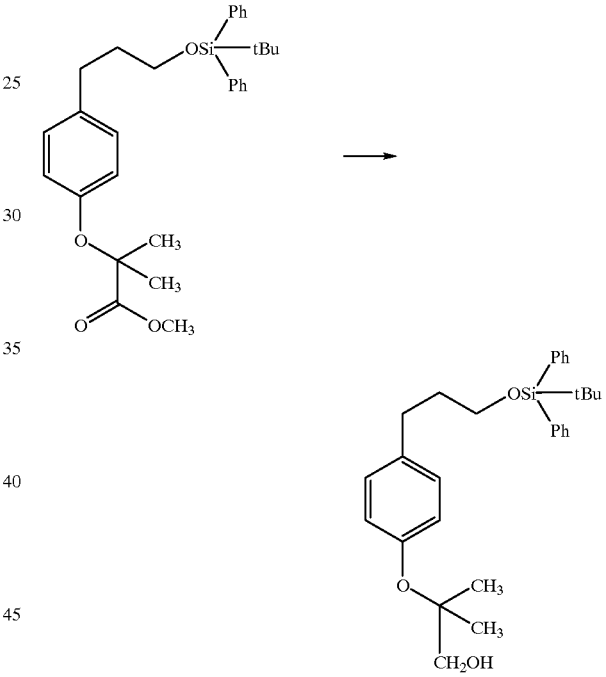

A solution of methyl 2-[4-[3-(tert-butyldiphenylsilyloxy)propyl]phenoxy]-2-methylpropionate (5.88 g, 11.98 mmol) in diethyl ether (100 ml) was treated at 22° C. with 23 ml (23 mmol) of a 1M solution of lithium aluminum hydride in ether. The resulting mixture was then heated under reflux for 1 hour. The cooled mixture was quenched by addition of ethyl acetate, water (5 ml) and 1N sodium hydroxide (5 ml). The solid formed was filtered and the filtrate was evaporated and purified on silica gel. Elution with a mixture of toluene and ethyl acetate (9:1) gave 5.14 g (93%) of the title material as an oil.

$^1$H NMR 400 MHz (CDCl$_3$) δ (ppm): 1.08 (9H, s, t-Bu) 1.27 (6H, s, CH$_3$), 1.87 (2H, m, CH$_2$), 2.22 (1H, t, J=6.67

Hz, OH), 2.70 (2H, t, J=7.5 Hz, CH$_2$), 3.59 (2H, d, J=6.67, CH$_2$OH), 3.69 (2H, d, J=6.3 Hz, OCH$_2$), 6.89 (2H, d, J=8.2 Hz, aromatic), 7.08 (2H, d, J=8.2 Hz, aromatic), 7.4 and 7.7 (6H and 4H, 2m, aromatic).

Anal. Calcd. for C$_{29}$H$_{38}$O$_3$Si: C, 75.28; H, 8.28. Found: C, 74.60; H, 8.28.

2-[4-[3-(tert-Butyldiphenyisilyloxy)propyl]phenoxy]-2-methyl propionaldehyde

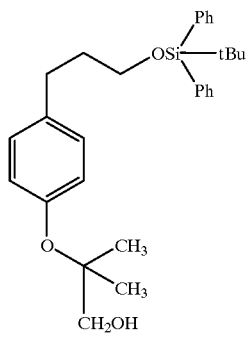

(2R and 2S)-3-[4-[3-tert-Butyldiphenylsilyloxy)propyl]phenoxy]-1,2epoxy-3-methylbutane

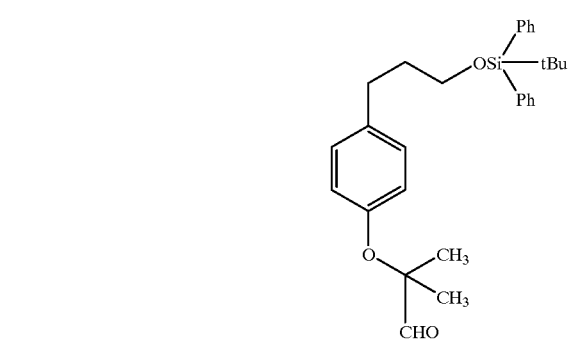

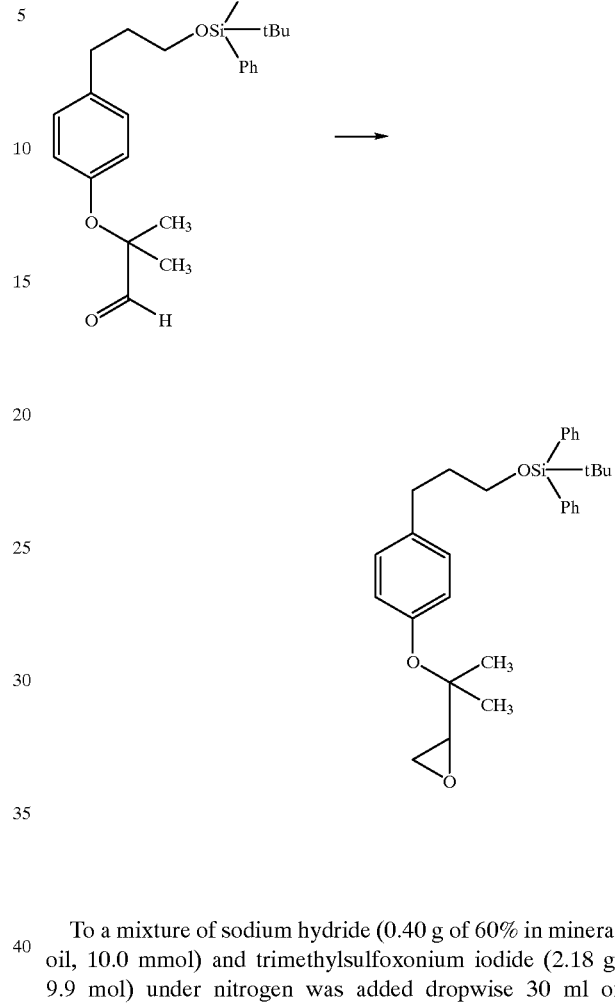

A solution of 2-[4-[3-(tert-butyldiphenylsilyloxy)propyl]phenoxy]-2-methyl propanol (5.14 g, 11.1 mmol) in dry dichloromethane (150 ml) was treated with 1,1,1-triacetoxy-1,1-dihydro-1,2-benziodoxol-3(1H)-one (Dess-Martin periodi-nane) (19.2 g, 45.3 mmol) and the resulting mixture was stirred at 22° C. for 3 hours. The reaction mixture was then diluted with ethyl acetate, washed with 5% sodium thiosulfate, saturated sodium bicarbonate, brine and dried (magnesium sulfate). Evaporation of the solvent and chromatography of the residue on silica gel (elution toluene ethyl acetate, 99:1) gave 3.25 g (63%) of the title material as a clear oil.

$^1$H NMR 400 MHz (CDCl$_3$) δ (ppm): 1.07 (9H, s, t-Bu) 1.42 (6H, s, CH$_3$), 1.85 (2H, m, CH$_2$), 2.67 (2H, broad t, J=7.8 Hz, CH$_2$), 3.68 (3H, t, J=6.4 Hz, OCH$_2$), 6.77 (2H, d, J=8.7 Hz, aromatic), 7.05 (2H, d, J=8.7 Hz, aromatic), 7.4 and 7.68 (6H and 4H, 2m, aromatic) and 9.87 (1H, s, CHO).

Anal. Calcd. for C$_{29}$H$_{36}$O$_3$Si: C, 75.61; H, 7.88. Found: C, 75.67; H, 7.85.

To a mixture of sodium hydride (0.40 g of 60% in mineral oil, 10.0 mmol) and trimethylsulfoxonium iodide (2.18 g, 9.9 mol) under nitrogen was added dropwise 30 ml of dimethylsulfoxide. After 30 minutes at 22° C., a solution of 2-[4-[3-(tert-butyldiphenylsilyloxy)propyl]phenoxy]-2-methylpropionaldehyde (3.05 g, 6.62 mmol) in dry dimethylsulfoxide (30 ml) was added over 5 minutes and the resulting mixture was stirred at 22° C. for 30 minutes. The reaction mixture was then quenched by addition of water and ethyl acetate. The organic phase was washed with water, brine and dried. Evaporation of the solvent and chromatography of the residue on silica gel (elution toluene-ethyl acetate, 98:2) gave 2.66 g (84%) of the title material as a clear oil.

$^1$H NMR 400 MHz (CDCl$_3$) δ (ppm): 1.08 (9H, s, t-Bu), 1.28 and 1.29 (2×3H, 2s, CH$_3$), 1.87 (2H, m, CH$_2$), 2.7 (3H, m, CH$_2$ and CH of oxirane), 2.81 (1H, broad t, CH of oxirane), 3.19 (1H, m, CH of oxirane), 3.70 (2H, t, J=6.8, OCH$_2$), 6.95 (2H, d, J=8.7 Hz, aromatic), 7.08 (2H, d, J=8.7 Hz, aromatic), 7.4 and 7.69 (6H and 4H, 2m, aromatic).

Anal. Calcd. for C$_{30}$H$_{48}$O$_3$Si: C, 75.90; H, 8.07. Found: C, 75.44; H, 8.06.

59

(2R and 3S)-3-[4-[3-(tert-Butyldiphenylsilyloxy)
propyl]phenoxy]-1-[4-(tert-butoxycarbonyl)
phenoxy]-3-methyl-2-butanol

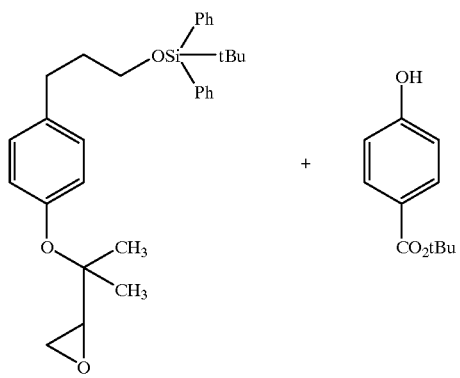

60

3-[4-[3-(tert-Butyldiphenyisilyloxy)propyl]
phenoxy]-1-[4-(tert-butoxycarbonyl)phenoxy]-3-
methyl-2-butanone

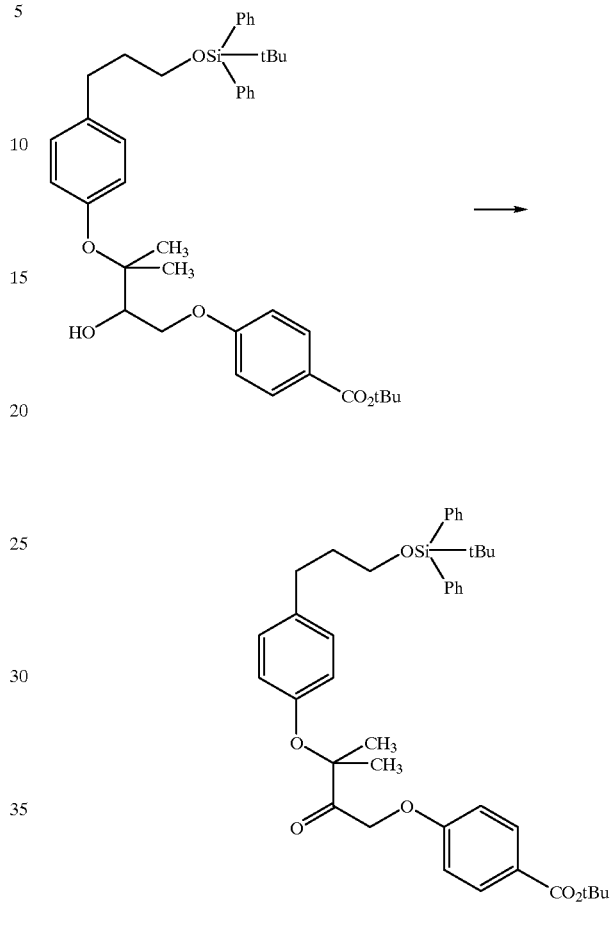

A mixture of (2R and 2S)-3-[4-[3-(tert-butyldiphenylsilyloxy)propyl]phenoxy]-1,2epoxy-3-methylbutane (2.58 g, 5.43 mmol) and 1,1-methylethyl 4-hydroxybenzoate (1.07 g, 5.51 mmol) in dry N,N-dimethylformamide (20 mL) was treated with 1,4-diazabicyclo[2,2,2] octane (0.20 g) and the resulting solution was stirred at 80° C. for 72 hours. Additional amounts of base (2×0.2 g) were added after 24 and 48 hours. The reaction mixture was then quenched by addition of water and ethyl acetate. The organic phase was washed with brine, dried (magnesium sulfate) and concentrated. The residue was chromatographed on silica gel (elution toluene-ethyl acetate, 95:5) to give 0.618 g (17%) of the title material as an oil.

$^1$H NMR 400 MHz (CDCl$_3$) δ (ppm): 1.09 (9H, s, t-Bu), 1.34 and 1.35 (2×3H, 2s, CH$_3$), 1.61 (9H, s, t-Bu), 1.9 (2H, m, CH$_2$), 2.71 (2H, broad t, CH$_2$), 3.70 (2H, t, J=6.1 Hz, OCH$_2$), 4.11 (1H, dd, J=3.3 and J=7.33 Hz, CH), 4.18 (1H, dd, J=7.33 and J=9.6 Hz, CH), 4.37 (1H, dd, J=3.17 and J=9.6 Hz, CH), 6.91 (2H, d, J=8.6 Hz, aromatic), 6.98 (2H, d, J=9.0 Hz, aromatic), 7.10 (2H, d, J=8.6 Hz, aromatic), 7.4 and 7.7 (6H and 4H, 2m, aromatic), 7.97 (2H, d, J=9.0 Hz, aromatic).

A solution of (2R and 2S)-3-[4-[3-(tert-butyldiphenysilyloxy)propyl]phenoxy]-1-[4-(tert-butoxycarbonyl)phenoxy]-3-methyl-2-butanol (0.60 g, 0.89 mmol) in dry dichloromethane (30 ml) was treated with 1,1,1-triacetoxy-1,1-dihydro-1,2-benziodoxol-3(1H)-one (Dess-Martin periodinane) (1.50 g, 3.57 mmol) and the resulting mixture was stirred at 22° C. for 3 hours. The reaction mixture was diluted with ethyl acetate, washed with 5% sodium thiosulfate, saturated sodium bicarbonate and brine. After drying (magnesium sulfate), the organic phase was concentrated and chromatographed on silica gel. Elution with a mixture of toluene and ethyl acetate (98:2) gave 0.587 g (98%) of the title material as a clear oil.

$^1$H NMR 400 MHz (CDCl$_3$) δ (ppm): 1.09 (9H, s, t-Bu), 1.54 (6H, s, 2×CH$_3$), 1.60 (9H, s, t-Bu), 1.87 (2H, m, CH$_2$), 2.71 (2H, broad t, CH$_2$), 3.70 (2H, t, J=6.3 Hz, OCH$_2$), 5.26 (2H, s, OCH$_2$), 6.82 (2H, d, J=8.5 Hz, aromatic), 6.92 (2H, d, J=8.5 Hz, aromatic), 7.11 (2H, d, J=8.5 Hz, aromatic), 7.4 and 7.7 (6H and 4H, 2m, aromatic), and 7.95 (2H, d, J=8.5 Hz, aromatic).

61

3-[4-[3-Hydroxypropyl)phenoxy]-1-[4-(tert-butoxycarbonyl)phenoxy]-3-methyl-2-butanone

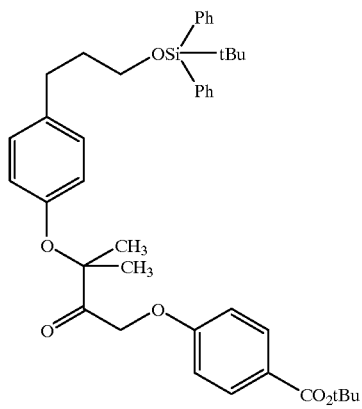

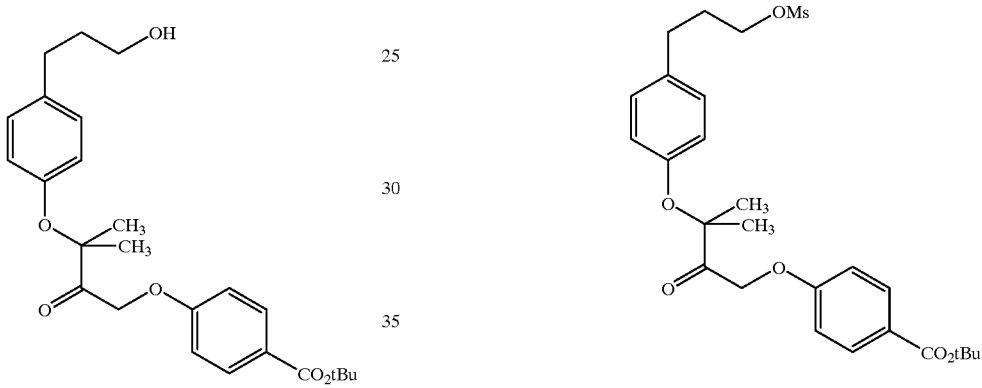

A solution of 3-[4-[3-(tert-butyldiphenylsilyloxy))propyl]phenoxy]-1-[4-tert-butoxycarbonyl)phenoxy]-3-methyl-2-butanone (0.562 g, 0.84 mmol) in tetrahydrofuran (20 ml) was treated with acetic acid (0.3 ml) followed with 2 ml (2.0 mmol) of 1 M tetrabutylammonium fluoride in tetrahydrofuran. The mixture was then heated at 70° C. for 3.5 hours. The cooled mixture was diluted with ethyl acetate, washed with saturated sodium bicarbonate, brine and dried (magnesium sulfate). Evaporation of the solvent and chromatography of the residue on silica gel (elution toluene-ethyl acetate, 8:2) gave 0.333 g (92%) of the title material as an oil.

$^1$H NMR 400 MHz (CDCl$_3$) δ (ppm): 1.55 (6H, s, 2×CH$_3$), 1.60 (9H, s, t-Bu), 1.9 (2H, m, CH$_2$), 2.70 (2H, broad t, CH$_2$), 3.70 (3H, t, J=6.2 Hz, OCH$_2$), 5.25 (2H, s, OCH$_2$), 6.85 (2H, d, J=8.5 Hz, aromatic), 6.91 (2H, d, J=8.9 Hz, aromatic), 7.15 (2H, d, J=8.5 Hz, aromatic) and 7.95 (2H, d, J=8.9 Hz, aromatic).

62

3-[4-(3-Methanesulfonyloxypropyl)phenoxy]-1-[4-(tert-butoxycarbonyl)phenoxy]-3-methyl-2-butanone

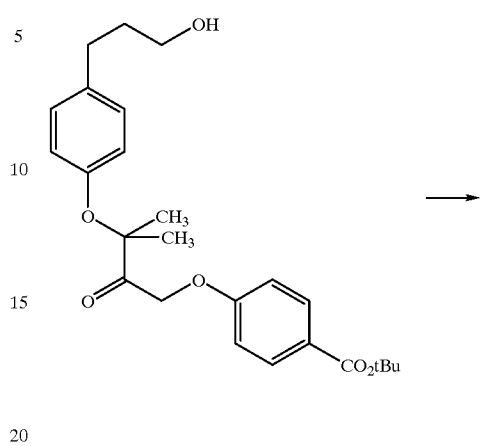

A solution of 3-[4-(3-hydroxypropyl)phenoxy]-1-[4-(tert-butoxycarbonyl)phenoxy]-3-methyl-2-butanone (0.312 g, 0.73 mmol) in dry dichloromethane (15 ml) was cooled to 0–5° C. and treated with triethylamine (0.23 ml, 1.65 mmol) followed with methanesulfonyl chloride (0.10 ml, 1.29 mmol) added dropwise over 2 minutes. The reaction mixture was stirred at 0° C. for 45 minutes and then quenched by the addition of ethyl acetate and water. The organic phase was washed with brine, dried (magnesium sulfate) and concentrated. The residue was chromatographed on silica gel (elution toluene-ethyl acetate, 85:15) to give 0.369 g (100%) of the title material as a clear oil.

$^1$H NMR 400 MHz (CDCl$_3$) δ (ppm): 1.55 (6H, s, 2×CH$_3$), 1.60 (9H, s, t-Bu), 2.08 (2H, m, CH$_2$), 2.74 (2H, broad t, J=7.5 Hz, CH$_2$), 3.03 (3H, s, Ms), 4.25 (2H, t, J=6.3 Hz, OCH$_2$), 5.24 (2H, s, OCH$_2$), 6.87 (2H, d, J=8.6 Hz, aromatic), 6.91 (2H, d, J=9.1 Hz, aromatic), 7.14 (2H, d, J=8.6 Hz, aromatic), and 7.95 (2H, d, J=9.1 Hz, aromatic).

MS (ESI$^+$) (m/z): 524 (M+NH$_4^+$).

3-[4-[3-[N-[2-Bis-(4-chlorophenyl)ethyl]-N-methylamino]propyl]phenoxy]-1-[4-(tert-butoxycarbonyl)phenoxy]-3-methyl-2-butanone

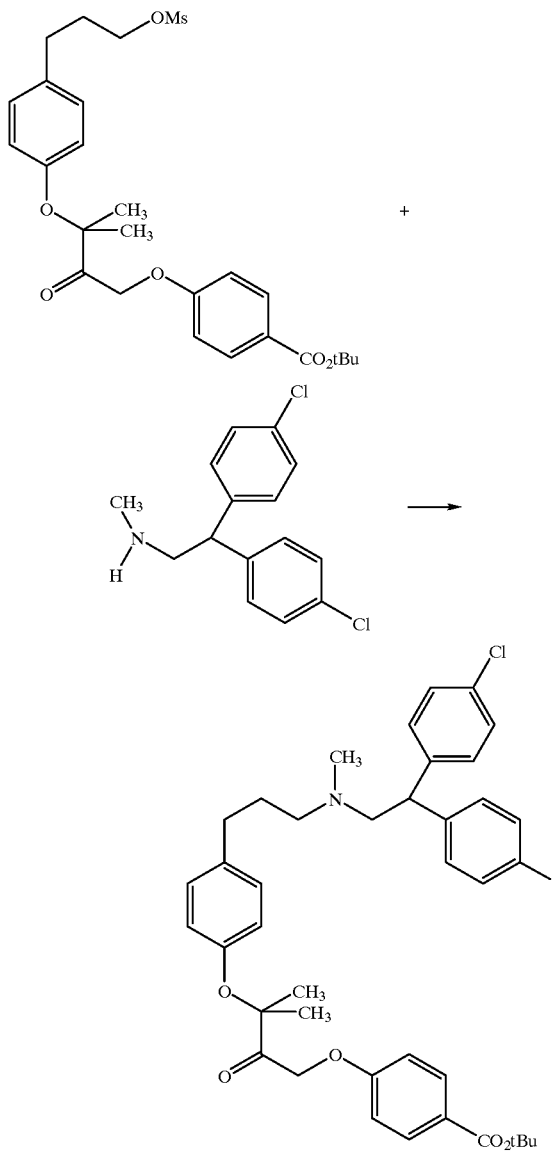

A solution of 3-[4-(3-methanesulfonyloxypropyl)phenoxy]-1-[4-(tert-butoxy carbonyl)phenoxy]-3-methyl-2-butanone (0.342 g, 0.67 mmol) and N-methyl-2-bis-(4-chlorophenyl)ethylamine (0.21 g, 0.74 mol) in acetonitrile (10 ml) was treated with N,N-diisopropylethylamine (0.15 ml) and sodium iodide (0.020 g) and the resulting mixture was heated at 80° C. for 20 hours. The cooled mixture was diluted with ethyl acetate, washed with saturated sodium bicarbonate, brine and dried (magnesium sulfate). Evaporation of the solvent and chromatography of the residue on silica gel (elution toluene-ethyl acetate, 85:15) gave 0.425 (91%) of the title material as an oil.

$^1$H NMR 400 MHz ($C_6D_6$) δ (ppm): 1.35 (6H, s, 2×$CH_3$), 1.60 (9H, s, t-Bu) 1.65 (2H, m, $CH_2$), 2.11 (3H, s, $NCH_3$), 2.28 (2H, t, J=6.8 Hz, $CH_2$), 2.43 (2H, t, J=7.6 Hz, $CH_2$), 2.67 (2H, d, J=8.2 Hz, $CH_2$), 3.90 (1H, t, J=8.2 Hz, CH), 5.04 (2H, s, $OCH_2$), 6.9 (10H, m, aromatic), 7.25 (2H, d, J=8 Hz, aromatic) and 8.22 (2H, d, J=9.1 Hz, aromatic).

MS (ESI$^+$) (m/z): 690 (M+H$^+$).

3-[4-[3-[N-[2-Bis-(4-chlorophenyl)ethyl]-N-methylamino]propyl]phenoxy]-1-[4-carboxyphenoxy]-3-methyl-2-butanone

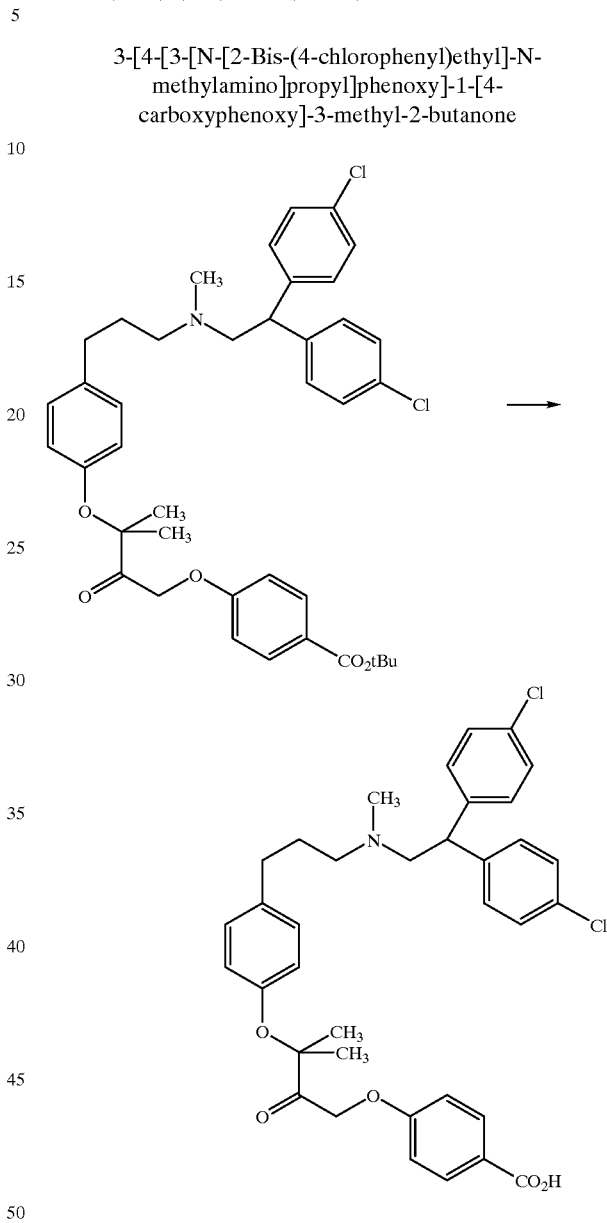

A solution of 3-[4-[3-[N-[2-bis-(4-chlorophenyl)ethyl]-N-methylamino]propyl]phenoxy]-1-[4-(tert-butoxycarbonyl)phenoxy]-3-methyl-2-butanone (0.400 g, 0.58 mmol) in 10 ml of a 1M solution of hydrochloric acid in acetic acid was stirred at 22° C. for 1.5 hours. The solvent was evaporated in vacuo and the residue was partitioned between dichloromethane and water while the pH of the aqueous phase was adjusted to 4.5 with 0.1N sodium hydroxide. The organic phase was dried (magnesium sulfate) concentrated and the residue was chromatographed on silica gel. Elution with a gradient of methanol (0–20%) in ethyl acetate gave 0.167 g (45%) of the title material as a syrup. The hydrochloride salt was prepared and obtained as a foam.

$^1$H NMR (hydrochloride salt) 400 MHz (DMSO-d$_6$) δ (ppm): 1.48 (6H, s, 2×CH$_3$), 1.95 (2H, m, CH$_2$), 2.95 (3H, broad s, NCH$_3$), 2.98 and 3.1 (2×1H, 2m, CH$_2$), 3.80 and 4.0 (2×1H, 2m, NCH$_2$), 4.67 (1H, t, J=7.6 Hz, CH), 5.44 (2H, s, OCH$_2$), 6.92 (2H, d, J=8.6 Hz, aromatic), 6.99 (2H, d, J=8.8 Hz, aromatic), 7.15 (2H, d, J=8.6 Hz, aromatic), 7.5 (8H, m, aromatic) and 7.88 (2H, d, J=8.8 Hz, aromatic).

HRMS (FAB) calculated for C$_{36}$H$_{38}$Cl$_2$NO$_5$ [MH]$^+$: 634.21271, Found: 634.2110, δ 2.7 ppm.

Example 6

(2R and 2S)-3-[4-[3-[N-[2-(Bis-[4-chlorophenyl)ethyl]N-methylamino]propyl]phenoxy]-1-(4-carboxyphenoxy)-2-acetoxypropane

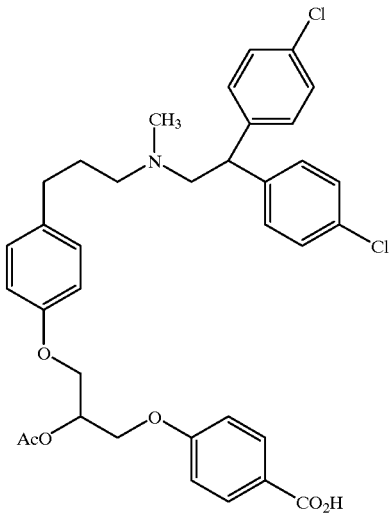

(2R and 2S)-3-[4-[3-(tert-Butyldiphenylsilyloxy)propyl]phenoxy]-1-[4-(tert-butoxycarbonyl)phenoxy]-2-acetoxypropane

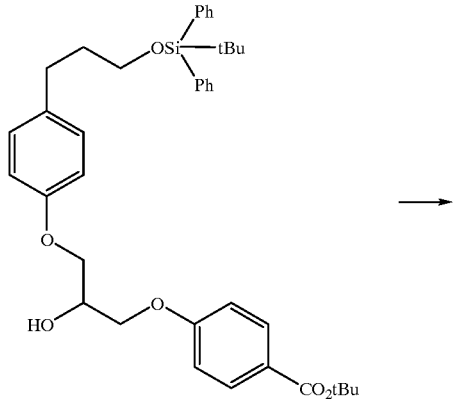

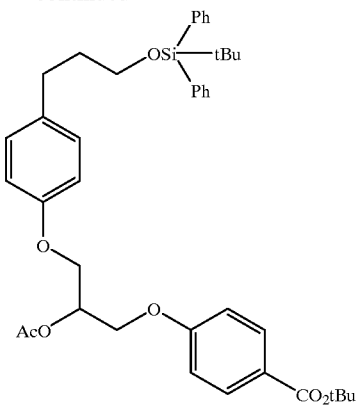

A solution of (2R and 2S)-3-[4-[3-(tert-butyldiphenylsilyloxy)propyl]phenoxy]-1-[4-(tert-butoxycarbonyl)phenoxy]-2-propanol (6.08 g, 9.5 mmol) in a mixture of pyridine (15 ml) and acetic anhydride (15 ml) was stirred at 22° C. for 1 hour. The excess reagents were then evaporated in vacuo and the residue was filtered through a silica gel pad (elution toluene-ethyl acetate, 95:5) to give 6.48 g (100%) of the title material as a clear oil.

$^1$H NMR 400 MHz (CDCl$_3$) δ (ppm): 1.08 (9H, s, t-Bu) 1.60 (9H, s, tBu), 1.85 (2H, m, CH$_2$), 2.14 (3H, s, CH$_3$CO), 2.68 (2H, t, J=7.6 Hz, CH$_2$), 3.69 (2H, t, J=6.3 Hz, OCH$_2$), 4.24 (2H, d, J=5.1 Hz, OCH$_2$), 4.33 (2H, d, J=4.5 Hz, OCH$_2$), 5.52 (1H, m, CH), 6.84 (2H, d, J=8.7 Hz, aromatic), 6.94 (2H, d, J=9.0 Hz, aromatic), 7.10 (2H, d, J=8.7 Hz, aromatic), 7.4 and 7.68 (6H and 4H, 2m, aromatic) and 7.96 (2H, d, J=9.0 Hz, aromatic).

Anal. Calcd. for C$_{41}$H$_{50}$O$_7$Si: C, 72.11; H, 7.38. Found: C, 72.06; H, 7.55.

(2R and 2S)-3-[4-(3-Hydroxypropyl)phenoxy]-1-[4-(tert-butoxycarbonyl)phenoxy]-2-acetoxypropane

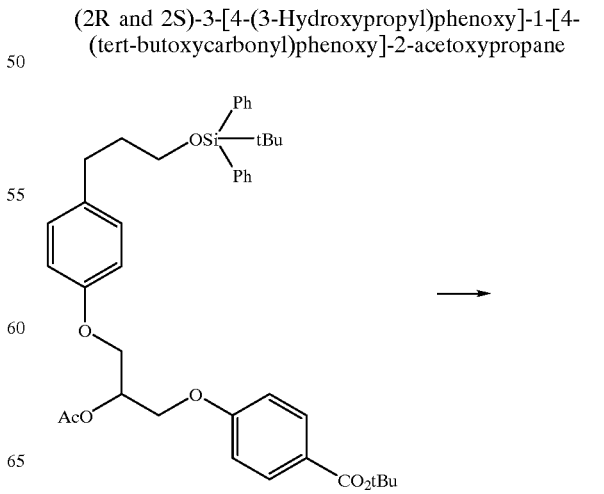

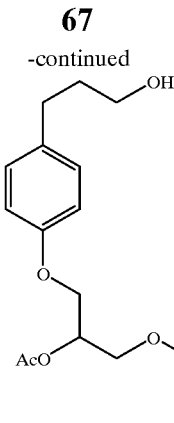

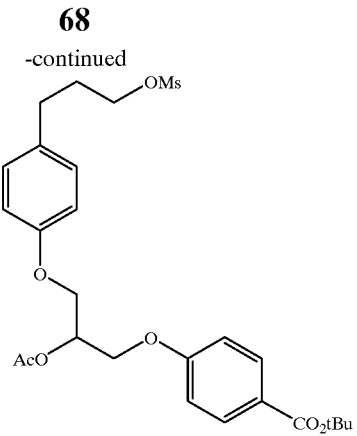

A solution of (2R and 2S)-3-[4-[3-(tert-butyldiphenylsilyloxy)propyl]phenoxy]-1-[4-(tert-butoxycarbonyl)phenoxy]-2-acetoxypropane (7.38 g, 10.8 mmol) in tetrahydrofuran (100 ml) was treated with acetic acid (3.7 ml) and 24 ml (24 mmol) of a 1M solution of tetrabutylammonium fluoride in tetrahydrofuran and the resulting mixture was heated at 70° C. for 4 hours. The cooled mixture was diluted with ethyl acetate, washed with water, saturated sodium bicarbonate, brine and dried (magnesium sulfate). Evaporation of the solvent and chromatography of the residue on silica gel (elution toluene-ethyl acetate, 75:25) gave 4.76 g (97%) of the title alcohol as an oil.

$^1$H NMR 400 MHz (CDCl$_3$) δ (ppm): 1.60 (9H, s, t-Bu) 1.88 (2H, m, CH$_2$), 2.14 (3H, s, CH$_3$CO), 2.68 (2H, t, J=7.5 Hz, CH$_2$), 3.68 (2H, t, J=6.5 Hz, OCH$_2$), 4.24 (2H, d, J=5.07 Hz, OCH$_2$), 4.31 (2H, d, J=3.44 Hz, OCH$_2$), 5.51 (1H, M, CH), 6.86 (2H, d, J=8.5 Hz, aromatic), 6.93 (2H, d, J=8.8 Hz, aromatic), 7.14 (2H, d, J=8.5 Hz, aromatic) and 7.95 (2H, d, J=8.8 Hz, aromatic).

Anal. Calcd. for C$_{25}$H$_{32}$O$_7$: C, 67.01; H, 7.29. Found: C, 66.98; H, 7.34.

A solution of (2R and 2S)-3-[4-[3-(hydroxypropyl)phenoxy]-1-[4-(tert-butoxycarbonyl)phenoxy]-2-acetoxypropane (4.71 g, 10.6 mmol) in dichloromethane (70 ml) was cooled to 0° C. and treated with triethylamine (3.1 ml, 22.2 mmol) followed by methanesulfonyl chloride (1.4 ml, 18.1 mmol) added dropwise over 5 minutes. After 1 hour at 0–5° C., the reaction mixture was quenched by addition of water and ethyl acetate. The organic phase was washed with water, saturated sodium bicarbonate and brine and dried (magnesium sulfate). Evaporation of the solvent and chromatography of the residue on silica gel (elution toluene-ethyl acetate, 9:1) gave 5.44 g (98%) of the title material as an oil.

$^1$H NMR 400 MHz (CDCl$_3$) δ (ppm): 1.60 (9H, s, t-Bu) 2.06 (2H, m, CH$_2$), 2.15 (3H, s, CH$_3$CO), 2.72 (2H, t, J=7.5 Hz, CH$_2$), 3.02 (3H, s, OMs), 4.23 (2H, t, J=6.0 Hz, OCH$_2$), 4.25 (2H, d, J=3.6 Hz, OCH$_2$), 4.31 (2H, d, J=4.36 Hz, OCH$_2$), 5.51 (1H, m, CH) 6.88 (2H, d, J=8.7 Hz, aromatic), 6.94 (2H, d, J=9.0 Hz, aromatic), 7.13 (2H, d, J=8.7 Hz, aromatic) and 7.95 (2H, d, J=8.7 Hz, aromatic).

Anal. Calcd. for C$_{26}$H$_{34}$O$_9$S.0.7 H$_2$O: C, 58.35; H, 6.67. Found: C, 58.35; H, 6.65.

(2R and 2S)-3-[4-(3-Methanesulfonyloxypropyl)phenoxy]-1-[4-(tert-butoxy carbonyl)phenoxy]-2-acetoxypropane

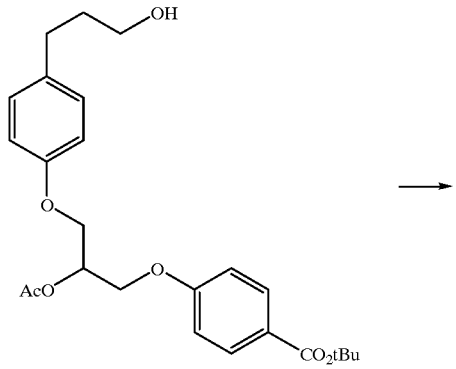

→

(2R and 2S)-3-[4-[3-[N-[2-Bis-(4-chlorophenyl)ethyl]N-methylamino]propyl]phenoxy]-1-[4-(tert-butoxycarbonyl)phenoxy]-2-acetoxypropane

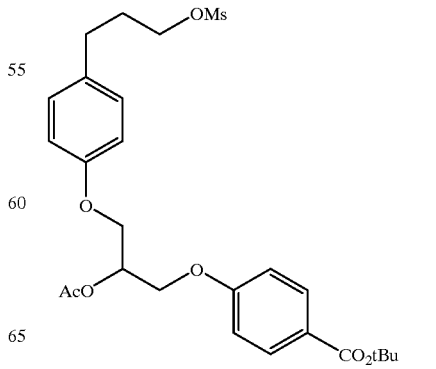

+

-continued

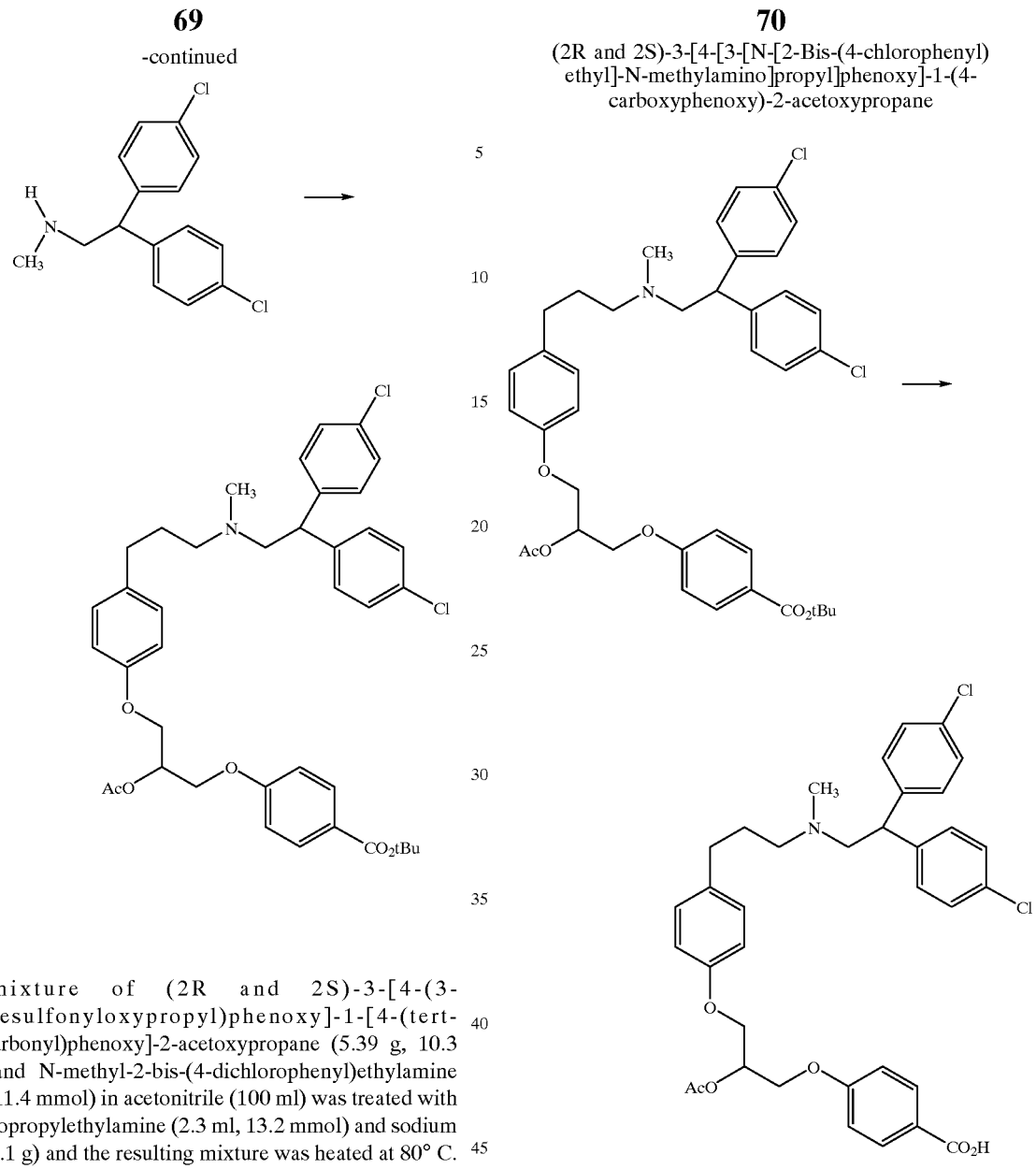

(2R and 2S)-3-[4-[3-[N-[2-Bis-(4-chlorophenyl) ethyl]-N-methylamino]propyl]phenoxy]-1-(4-carboxyphenoxy)-2-acetoxypropane A mixture of (2R and 2S)-3-[4-(3-methanesulfonyloxypropyl)phenoxy]-1-[4-(tert-butoxycarbonyl)phenoxy]-2-acetoxypropane (5.39 g, 10.3 mmol) and N-methyl-2-bis-(4-dichlorophenyl)ethylamine (3.21 g, 11.4 mmol) in acetonitrile (100 ml) was treated with N,N-diisopropylethylamine (2.3 ml, 13.2 mmol) and sodium iodide (0.1 g) and the resulting mixture was heated at 80° C. for 18 hours. The cooled mixture was diluted with ethyl acetate, washed with water, saturated sodium bicarbonate and dried (magnesium sulfate). Evaporation of the solvent and chromatography of the residue on silica gel (elution toluene-ethyl acetate, 8:2) gave 5.74 g (79%) of the title material as a clear syrup.

$^1$H NMR 400 MHz (DMSO-$d_6$) δ (ppm): 1.53 (9H, s, t-Bu) 1.57 (2H, m, CH$_2$), 2.06 (3H, s, CH$_3$CO), 2.16 (3H, s, NCH$_3$), 2.31 (4H, m, 2×CH$_2$), 2.85 (2H, d, J=8.0 Hz, NCH$_2$), 4.23 (3H, m, OCH$_2$ and CH), 4.33 (2H, m, OCH$_2$), 5.42 (1H, m, CH), 6.85 (2H, d, J=8.6 Hz, aromatic), 6.99 (2H, d, J=8.6 Hz, aromatic), 7.06 (2H, d, J=9.1 Hz, aromatic) and 7.85 (2H, d, J=9.1 Hz, aromatic).

Anal. Calcd. for C$_{40}$H$_{45}$Cl$_2$NO$_6$: C, 67.98; H, 6.42; N, 1.98. Found: C, 67.97; H, 6.46; N, 2.05.

A solution of (2R and 2S)-3-[4-[3-[N-[2-bis-(4-chlorophenyl)ethyl]-N-methylamino]propyl]phenoxy]-1-[4-(tert-butoxycarbonyl)phenoxy]-2-acetoxypropane (0.390 g, 0.55 mmol) in 10 ml of 1M hydrochloric acid in acetic acid was stirred at 22° C. for 1.5 hours. The solvent was then evaporated in vacuo and the residue was partitioned between dichloromethane and water while the pH of the aqueous phase was adjusted to 4.5 with 0.1N sodium hydroxide. The aqueous phase was extracted twice with dichloromethane and the combined organic phases were dried (magnesium sulfate) and concentrated. Chromatography of the residue on silica gel (elution ethyl acetate-methanol, 0–20%) gave 0.27 g (76%) of the title material as a white foam. The hydrochloride salt was prepared and obtained as an amorphous solid.

$^1$H NMR (hydrochloride salt) 400 MHz (DMSO-$d_6$) δ (ppm): 0.87 (2H, m, CH$_2$), 2.06 (3H, s, CH$_3$CO), 2.47 (2H, m, CH$_2$), 2.72 (3H, broad s, NCH$_3$), 2.92 and 3.03 (2×1H, 2 m, NCH$_2$), 3.8 and 3.98 (2×1H, 2m, NCH$_2$), 4.24 (2H, m, OCH$_2$), 4.37 (2H, m, OCH$_2$), 4.71 (1H, broad t, J=6.7 Hz, CH), 5.43 (1H, m, CH), 6.91 (2H, d, J=8.4 Hz, aromatic), 7.06 (2H, d, J=8.5 Hz, aromatic), 7.10 (2H, d, J=8.4 Hz, aromatic), 7.43 (8H, m, aromatic) and 7.89 (2H, d, J=8.5 Hz, aromatic).

Anal. Calcd. for $C_{36}H_{37}Cl_2NO_6 \cdot HCl \cdot 2HO$: C, 59.80; H, 5.85; N, 1.94. Found: C, 59.68; H, 5.50; N, 1.95.

Example 7

(2R and 2S)-3-[4-[3-[N-[2-Bis-(4-chlorophenyl)ethyl]-N-methylamino]propyl]phenoxy]-1-(4-carboxyphenoxy)-2-trimethylacetoxypropane

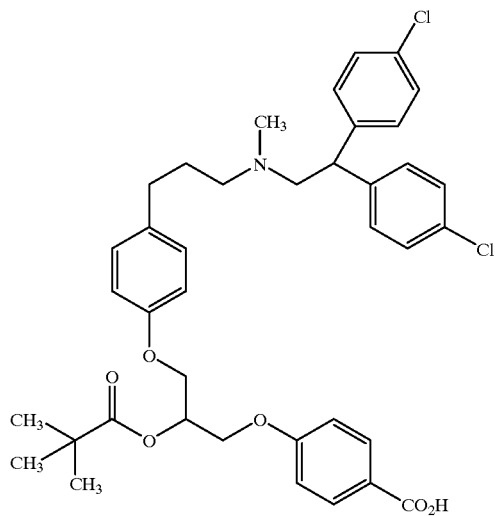

(2R and 2S)-3-[4-[3-[N-[2-Bis-(4-chlorophenyl)ethyl]-N-methylamino]propyl]phenoxy]-1-[4-(tert-butoxycarbonyl)phenoxy]-2-propanol

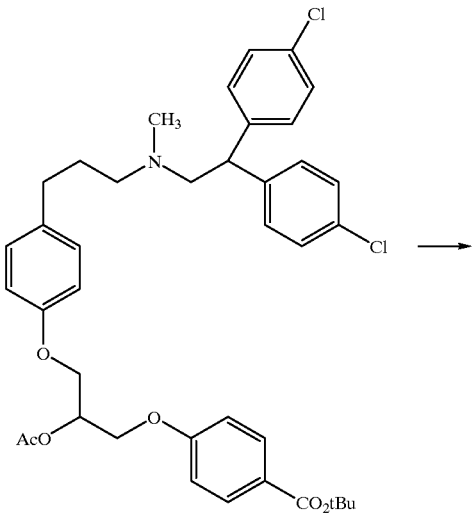

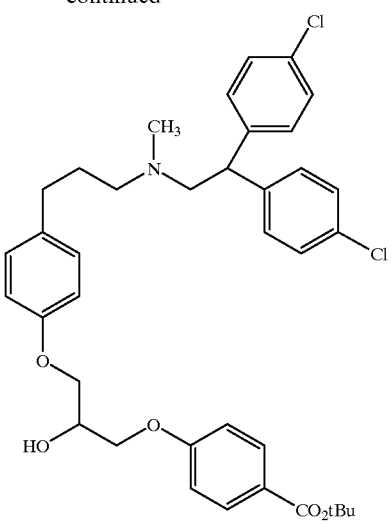

A solution of (2R and 2S)-3-[4-[3-[N-[2-bis-(4-chlorophenyl)ethyl]-N-methylamino]propyl]phenoxy]1-[4-(tert-butoxycarbonyl)phenoxy]-2-acetoxypropane (4.19 g, 5.93 mol) in 80% ethanol (100 ml) was treated with a solution of potassium hydroxide (2 g) in water (5 ml) and the resulting mixture was heated at 80° C. for 1 hour. The cooled mixture was concentrated in vacuo, diluted with ethyl acetate, washed with water and brine and dried (magnesium sulfate). Evaporation of the solvent and chromatography of the residue on silica gel (elution toluene-ethyl acetate, 7:3) gave 3.52 g (89%) of the title material as a foam.

$^1$H NMR 400 MHz (DMSO-$d_6$) δ (ppm): 1.53 (9H, s, t-Bu), 1.58 (2H, m, $CH_2$), 2.16 (3H, s, $NCH_3$), 2.3 (4H, m, 2×$CH_2$), 2.85 (2H, d, J=8.1 Hz, $NCH_2$), 3.9–4.2 (5H, m, 2×$OCH_2$ and CH), 4.23 (1H, t, J=8.1 Hz, CH), 5.4 (d, J=5.5 Hz, OH), 6.84 (2H, d, J=8.6 Hz, aromatic), 6.97 (2H, d, J=8.6 Hz, aromatic), 7.04 (2H, d, J=8.7 Hz, aromatic), 7.32 (8H, s, aromatic) and 7.84 (2H, d, J=8.7 Hz, aromatic).

Anal. Calcd. for $C_{38}H_{43}Cl_2NO_5 \cdot 0.5\ H_2O$: C, 67.75; H, 6.58; N, 2.08. Found: C, 67.87; H, 6.40; N, 2.13.

(2R and 2S)-3-[4-[3-[N-[2-Bis-(4-chlorophenyl)ethyl]-N-methylamino]propyl]phenoxy]-1-(4-tert-butoxycarbonyl)phenoxy]-2-trimethylacetoxypropane

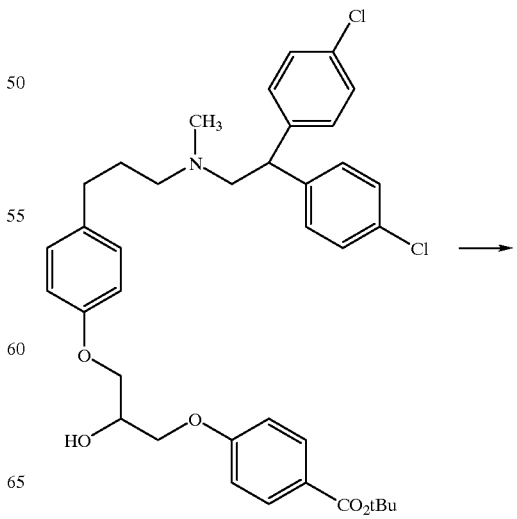

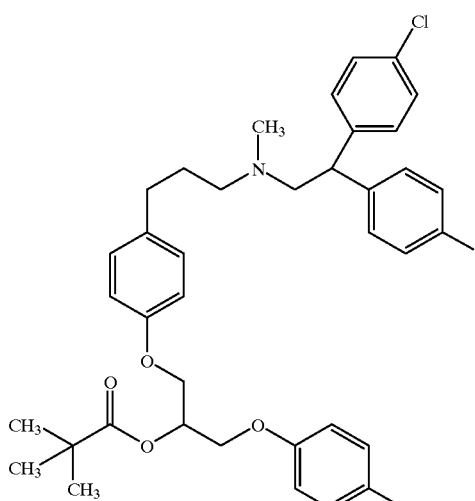

A solution of (2R and 2S)-3-[4-[3-[N-[2-bis-(4-chlorophenyl)ethyl]-N-methylamino]propyl]phenoxy]-1-[4-(tert-butoxycarbonyl)phenoxy]-2-propanol (0.593 g, 0.89 mmol) in tetrahydrofuran (10 ml) was treated at 22° C. with pyridine (0.6 ml) and 4-(dimethylamino)pyridine (0.055 g) followed by trimethylacetyl chloride (0.5 ml, 4.1 mmol) added dropwise over 5 minutes. After 18 hours at 22° C., the reaction mixture was diluted with ethyl acetate, washed with water, saturated sodium bicarbonate, brine and dried (magnesium sulfate). Evaporation of the solvent and chromatography of the residue on silica gel (elution toluene-ethyl acetate, 9:1) gave 0.485 g (73%) of the title material as an oil.

$^1$H NMR 400 MHz (DMSO-$d_6$) δ (ppm): 1.1 (9H, s, t-Bu), 1.53 (9H, s, t-Bu), 1.59 (2H, m, $CH_2$), 2.16 (3H, s, $NCH_3$), 2.3 (4H, m, 2×$CH_2$), 2.85 (2H, d, J=8.2 Hz, $NCH_2$), 4.2–4.4 (5H, m, 2×$OCH_2$ and CH), 5.41 (1H, m, CH), 6.85 (2H, d, J=8.6 Hz, aromatic), 6.98 (2H, d, J=8.6 Hz, aromatic), 7.05 (2H, d, J=9.1 Hz, aromatic), 7.32 (8H, s, aromatic) and 7.85 (2H, d, J=9.1 Hz, aromatic).

Anal. Calcd. for $C_{43}H_{51}Cl_2NO_6$: C, 68.97; H, 6.87; N, 1.87. Found: C, 68.70; H, 7.01; N, 1.89.

(2R and 2S)-3-[4-[3-[N-[2-Bis-(4-chlorophenyl)ethyl]-N-methylamino]propyl]phenoxy]-1-(4-carboxyphenoxy)-2-trimethylacetoxypropane

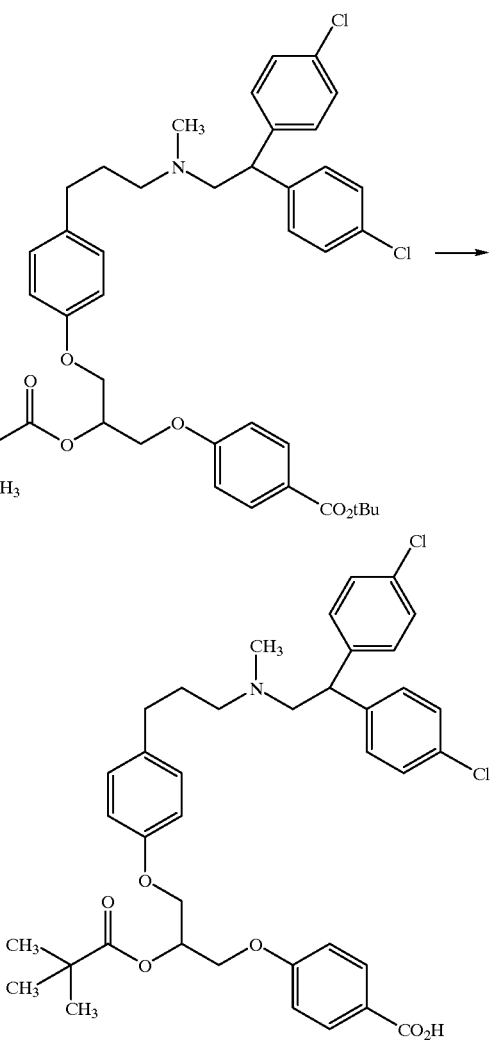

A solution of (2R and 2S)-3-[4-[3-[N-[2-bis-(4-chlorophenyl)ethyl]-N-methylamino]propyl]phenoxy]-1-[4-(tert-butoxycarbonyl)phenoxy]-2-trimethylacetoxypropane (0.450 g, 0.60 mmol) in 10 ml of 1M hydrochloric acid in acetic acid was stirred at 22° C. for 1 hour. The solvent was then evaporated in vacuo and the residue was partitioned between dichloromethane and water while the pH of the aqueous phase was adjusted to 4.5 with 0.1N sodium hydroxide. The organic phase was dried (magnesium sulfate), evaporated and the residue was chromatographed on silica gel (elution ethyl acetate-methanol; 8:2) to give 0.326 g (78%) of the title material as a white foam. The hydrochloride salt was prepared as usual and obtained as a foam.

$^1$H NMR (hydrochloride salt) 400 MHz (DMSO-$d_6$) δ (ppm): 1.1 (9H, s, t-Bu), 1.9 (2H, m, $CH_2$), 2.48 (2H, m, $CH_2$), 2.74 (3H, broad s, $NCH_3$), 3.0 (2H, m, $NCH_2$), 3.79 and 3.98 (2×1H, 2m, $NCH_2$), 4.25 (2H, AB part of ABX system, $J_{AB}$=11.0 Hz, $J_{AX}$=6.2 Hz, $J_{BX}$=4.1 Hz, $OCH_2$), 4.35 (2H, AB part of ABX system, $J_{AB}$=11.0 Hz, $J_{AX}$=6.1 Hz, $J_{BX}$=4.1 Hz, $OCH_2$), 4.67 (1H, broad t, J=7.3 Hz, CH), 5.42

(1H, m, CH), 6.91 (2H, d, J=8.1 Hz, aromatic), 7.06 (2H, d, J=9.1 Hz, aromatic), 7.1 (2H, d, J=8.1 Hz, aromatic) and 7.9 Hz (2H, d, J=9.1 Hz, aromatic).

Anal. Calcd. for $C_{39}H_{43}Cl_2NO_6 \cdot HCl \cdot 2.5\ H_2O$: C, 60.51; H, 6.38; N, 1.81. Found: C, 60.53; H, 5.82; N, 1.84.

Example 8

(2R and 2S)-3-[4-[3-[N-[2-Bis-(4-chlorophenyl)ethyl]-N-methylamino]propyl]phenoxy]-1-(4-carboxyphenoxy)-2-propylamine

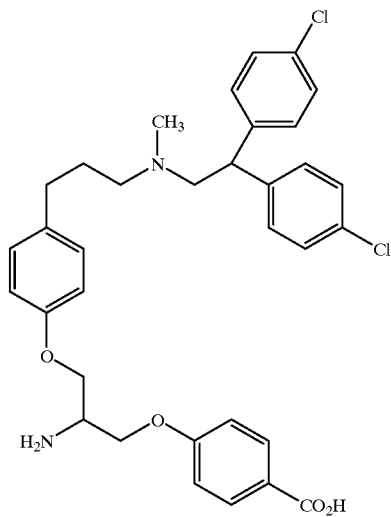

(2R and 2S)-3-[4-[3-[N-[2-Bis-(4-chlorophenyl)ethyl]-N-methylamino]propyl]phenoxy]-1-(4-(tert-butoxycarbonyl)phenoxy]-2-azidopropane

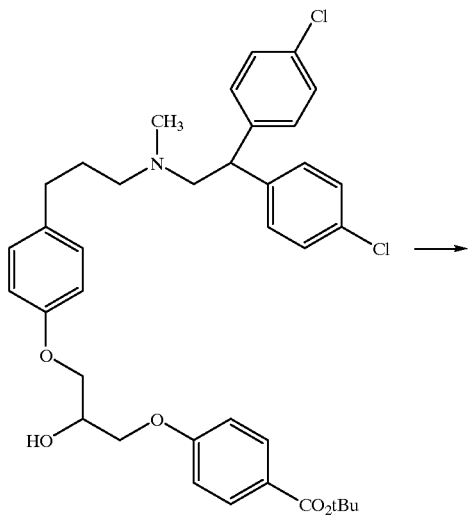

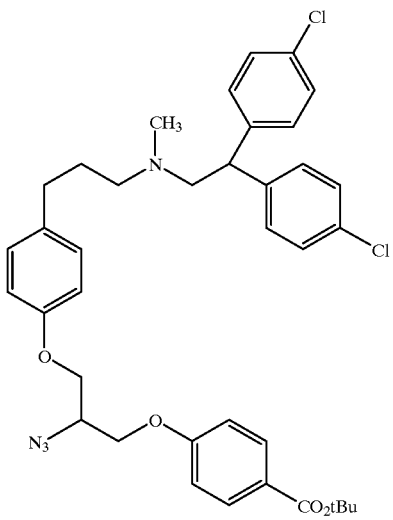

A solution of 3-[4-[3-[N-[2-bis-(chlorophenyl)ethyl]-N-methylamino]propyl]phenoxy]-[4-(tert-butoxycarbonyl)phenoxy]-2-propanol (2.61 g, 3.93 mmol) and triphenylphosphine (1.65 g, 6.3 mol) in tetrahydrofuran (60 ml) at 0–5° C. was treated with 17 ml (11.9 mmol) of a 0.7 solution of hydrazoic acid in toluene. Then a solution of diethyl azodicarboxylate (1.06 ml, 6.7 mmol) in tetrahydrofuran (5 ml) was added dropwise over 10 minutes. After 3 hours at 0–5° C., the reaction mixture was diluted with ethyl acetate, washed with saturated sodium bicarbonate, brine and dried (magnesium sulfate). Evaporation of the solvent and chromatography of the residue on silica gel (elution toluene-ethyl acetate, 9:1) gave 2.08 g (77%) of the title material as an oil.

$^1$H NMR 400 MHz (DMSO-$d_6$) δ (ppm): 1.53 (9H, s, t-Bu) 1.58 (2H, m, $CH_2$), 2.16 (3H, s, $NCH_3$), 2.32 (4H, m, 2×$CH_2$), 2.85 (2H, d, J=7.7 Hz $NCH_2$), 4.1–4.4 (6H, m, 2×$OCH_2$ and 2×CH), 6.87 (2H, d, J=8.6 Hz, aromatic), 7.01 (2H, d, J=8.6 Hz, aromatic), 7.07 (2H, d, J=8.8 Hz, aromatic), 7.33 (8H, s, aromatic) and 7.87 (2H, d, J=8.6 Hz, aromatic).

Anal. Calcd. for $C_{38}H_{42}Cl_2N_4O_4 \cdot 0.3\ H_2O$: C, 65.66; H, 6.18; N, 8.06. Found: C, 65.69; H, 6.28; N, 8.12.

(2R and 3S)-3-[4-[3-[N-[2-Bis-(4-chlorophenyl)ethyl]-N-methylamino]propyl]phenoxy]-1-(4-(carboxyphenoxy)-2-propylamine

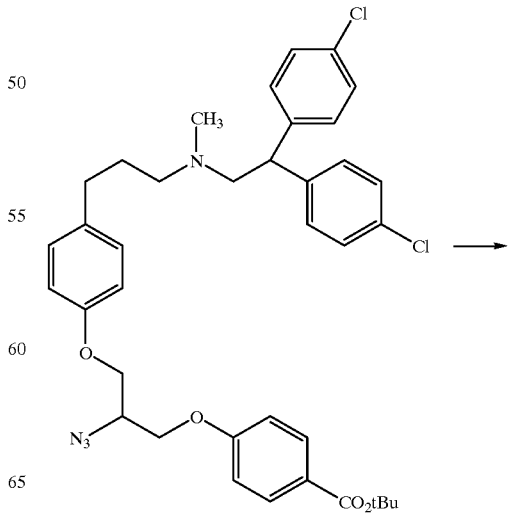

77
-continued

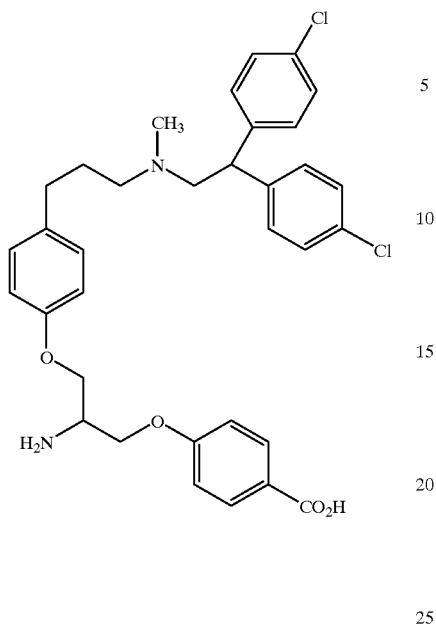

A solution of (2R and 2S)-3-[4-[3-[N-[2-bis-(4-chlorophenyl)ethyl]-N-methylamino]propyl]phenoxy]-1-[4-(tert-butoxycarbonyl)phenoxy]-2-azidopropane (0.530 g, 0.77 mmol) in a mixture of tetrahydrofuran (25 ml) and water (5 ml) was treated with triphenylphosphine (0.60 g) and the resulting mixture was stirred at 22° C. for 18 hours. The reaction mixture was then diluted with ethyl acetate, washed with water, brine and dried (magnesium sulfate). Evaporation of the solvent gave the crude amine that was then diluted in dichloromethane (20 ml) and treated at 22° C. with trifluoroacetic acid (3 ml). After 3 hours, the solvent was evaporated in vacuo and the residue was partitioned between ethyl acetate and water while the pH of the aqueous phase was adjusted to pH 7 with 0.1N sodium hydroxide. The organic phase was dried (magnesium sulfate), concentrated and the residue was chromatographed on silica gel. Elution with a mixture of ethyl acetate, methanol and water (60:40:2) gave 0.087 g (19%) of the title material as a foam. The hydrochloride salt was prepared as usual and obtained as an amorphous solid.

$^{1}$H NMR (bis hydrochloride salt) 400 MHz (DMSO-$d_6$) δ (ppm): 1.9 (2H, m, CH$_2$), 2.74 (3H, broad s, NCH$_3$), 3.0 (2H, m, CH$_2$), 3.79 and 3.98 (1H and 2H, 2m, NCH$_2$ and CH), 4.27 (2H, AB part of ABX system, J$_{AB}$=10.3 Hz, J$_{AX}$=5.9 Hz, J$_{BX}$=3.9 Hz, OCH$_2$), 4.37 (2H, AB part of ABX system, J$_{AB}$=10.7 Hz, J$_{AX}$=6.1 Hz, J$_{BX}$=4.4 Hz, OCH$_2$), 4.68 (1H, broad t, J=7.0 Hz, CH), 6.95 (2H, d, J=8.6 Hz, aromatic), 7.10 (2H, d, J=8.8 Hz, aromatic), 7.14 (2H, d, J=8.6 Hz, aromatic), 7.45 (8H, m, aromatic) and 7.94 (2H, d, J=8.8 Hz, aromatic).

HRMS (FAB) Calcd. for C$_{34}$H$_{37}$O$_4$N$_2$$^{35}$Cl$_2$ [MH]$^{+}$: 607.21301, Found: 607.21430, δ 2.1 ppm.

78
Example 9

4-[4-[2-[N-[2-Bis-(4-chlorophenyl)ethyl]-N-methylamino]ethoxy]phenyl]-2,2-difluoro-1-methoxy-2-butanone

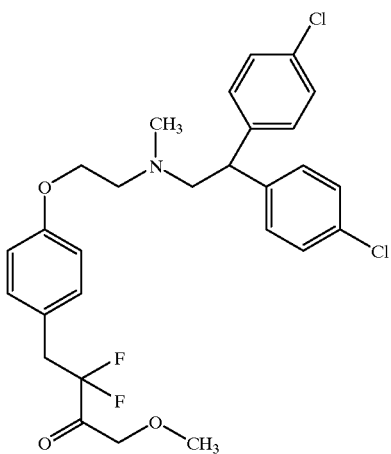

Ethyl 2,2-difluoro-3-iodo-3-(4-methoxyphenyl) propionate

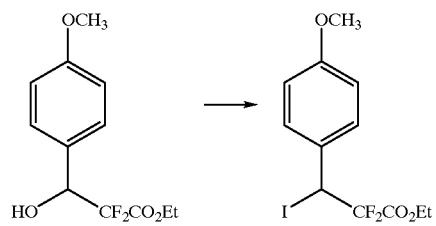

A solution of ethyl 2,2-difluoro-3-hydroxy-3-(4-methoxyphenyl) propionate (5.03 g, 22.4 mmol) [J. M. Andres, et al., *Synthesis*, (1996) 1070–1071] and triethylamine (6.56 ml, 47.0 mmol) in dichloromethane (45 ml) was treated at 0° C. with methanesulfonyl chloride (4.36 g, 38.0 mmol) added dropwise over 5 minutes. After 30 minutes at 22° C., the reaction mixture was diluted with dichloromethane, washed with 0.1N HCl, brine and dried (magnesium sulfate). Evaporation of the solvent gave an oil (7.92 g) that was diluted with acetone and treated with sodium iodide (7.22 g). The resulting mixture was then heated at 50° C. for 18 hours. The solvent was then concentrated in vacuo and the residue was partitioned between toluene and water. The organic phase was washed with 10% sodium thiosulfate, brine and dried (magnesium sulfate). Evaporation of the solvent and chromatography of the residue on silica gel (elution toluene-hexane, 7:3) gave 6.37 g (77%) of the title material as a light yellow solid: mp 44–45° C.

Anal. Calcd. for C$_{12}$H$_{13}$F$_2$IO$_3$: C, 38.94; H, 3.54. Found: C, 39.12; H, 3.42.

Ethyl 2,2-difluoro-3-(4-methoxyphenyl)-propionate

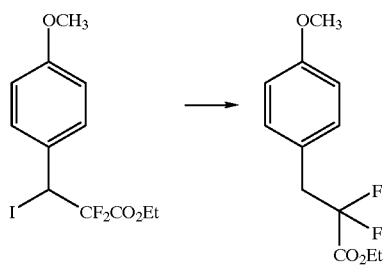

A solution of ethyl 2,2-difluoro-3-iodo-3-(4-methoxyphenyl)-propionate (5.24 g, 14.2 mmol) in toluene (125 ml) was treated with tributyltin hydride (28.9 g, 0.10 mol) and a few crystals of 2,2'-azobisisobutyronitrile. The resulting solution was then irradiated for 15 minutes at 25° C. with a sun lamp. The solvent was then evaporated in vacuo and the residue was partitioned between acetonitrile and pentane. The acetonitrile fraction was concentrated and chromatographed on silica gel (elution hexane-ethyl acetate, 85:15) to give 2.65 g (76%) of the title material as an oil: bp 90–95° C./0.1 torr (air bath temperature).

Anal. Calcd. for $C_{12}H_{14}F_2O_3$: C, 59.01; H, 5.78. Found: C, 58.89; H, 5.51.

Ethyl 2,2-difluoro-3-phenoxythiocarboxyloxy-3-(4-methoxyphenyl) propionate

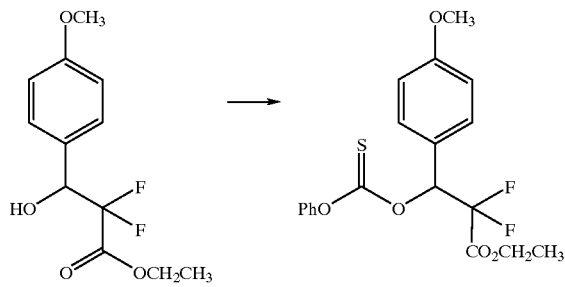

A solution of ethyl 2,2-difluoro-3-hydroxy-3-(4-methoxyphenyl)propionate (3.01 g, 11.6 mmol) in dichloromethane (30 ml) was cooled to 0° C., and reacted with pyridine (4.5 g, 56.0 mmol) followed by phenylchlorothionoformate (2.49 g, 14.4 mmol) added dropwise over 5 minutes. The resulting mixture was then stirred at 22° C. for 18 hours. The reaction mixture was then quenched by addition of water and dichloromethane. The organic phase was washed with water, 1N hydrochloric acid, saturated sodium bicarbonate and brine. After drying, the solvent was evaporated in vacuo and the residue was chromatographed on silica gel. Elution with a mixture of hexane and toluene (1:1) gave 4.58 g (100%) of the title material as a clear oil.

Anal. Calcd. for $C_{19}H_{18}F_2O_5S$: C, 57.57; H, 4.58. Found: C, 57.59; H, 4.70.

Ethyl 2,2-difluoro-3-(4-methoxyphenyl)-propionate

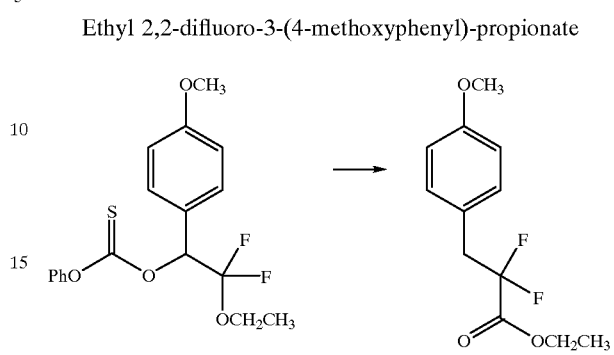

A solution of ethyl 2,2-difluoro-3-phenoxythiocarbonyloxy-3-(4-methoxyphenyl) propionate (5.10 g, 12.9 mmol) in benzene (80 ml) was treated with tributyltin hydride (4.5 g, 15.5 mmol) and 2,2'-azobiisobutyronitrile (AIBN, 0.070 g) and the resulting mixture was heated under reflux for 3 hours. The solvent was evaporated under reduced pressure and the residue was chromatographed on silica gel (elution toluene-hexane 1:1) to give 2.52 g (80%) of the title material as an oil: bp 90–95° C./0.1 torr (air bath temperature).

Ethyl 2,2-difluoro-3-(4-hydroxyphenyl)-propionate

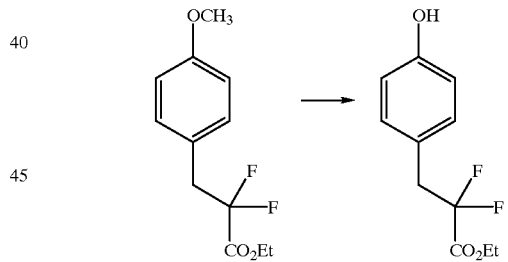

A solution of ethyl 2,2-difluoro-3-(4-hydroxyphenyl)-propionate (2.0 g, 8.18 mmol) in dichloromethane (80 ml) was reacted dropwise at 0° C. with 37 ml (37 mmol) of a 1M solution of boron tribromide in dichloromethane. After 2.5 hours at 0° C., the mixture was quenched by the addition of ice water and dichloromethane. The organic phase was washed with water, dried over anhydrous sodium sulfate and evaporated in vacuo. Chromatography of the residue on silica gel (elution hexane-ethyl acetate, 7:3) gave 1.50 g (80%) of the title material as an oil.

Anal. Calcd. for $C_{11}H_{12}F_2O_3$: C, 57.39; H, 5.25. Found: C, 57.06; H, 5.44.

81

3-[4-[2-[N-[2-Bis-(4-chlorophenyl)ethyl]-N-methylamino]ethoxy]phenyl]-2,2-difluoropropanoic acid methyl ester

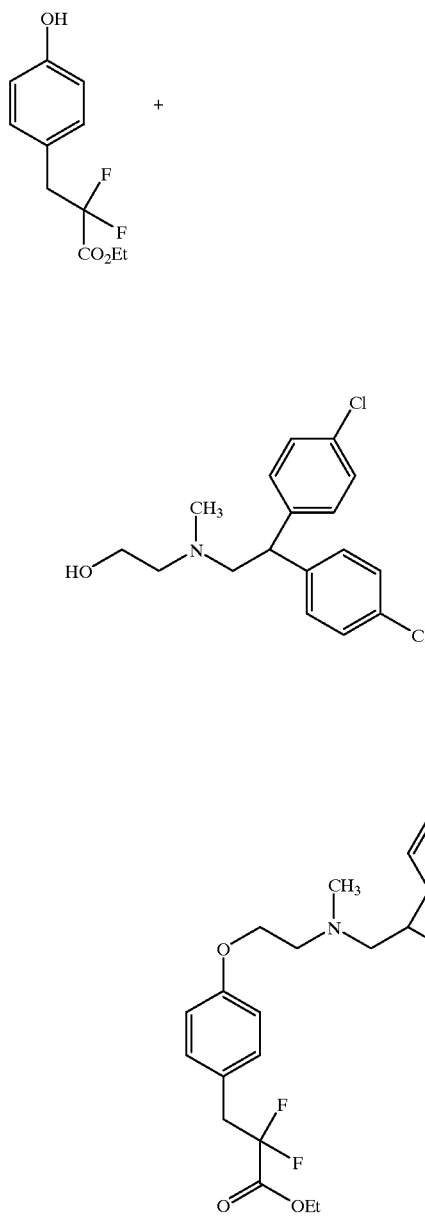

In A solution of ethyl 2,2difluoro-3-(4-hydroxyphenyl)-propionate (1.0 g, 4.34 mmol), 2-[N-[2-bis-(chlorophenyl)ethyl]-N-methylamino]ethanol (1.52 g, 4.68 mmol) and triphenylphosphine (1.25 g, 4.76 mmol) in benzene (20 ml) was treated at 22° C. with diethyl azodicarboxylate (0.831 g, 4.77 mmol) added dropwise over 2 minutes. After 2.5 hours at 22° C., the resulting mixture was diluted with ethyl acetate, washed with saturated sodium bicarbonate, brine and dried over anhydrous magnesium sulfate. Evaporation of the solvent and chromatography of the residue on silica gel (elution toluene-ethyl acetate, 92:8) gave 1.32 g (57%) of the title material as an oil.

Anal. Calcd. for $C_{28}H_{29}Cl_2F_2NO_3$: C, 62.69; H, 5.45; N, 2.61. Found: C, 62.83; H, 5.58; N, 2.62.

82

3-[4-[2-[N-[2-Bis-(4-chlorophenyl)ethyl]-N-methylamino]ethoxy]phenyl]-2,2-difluoropropanoic acid

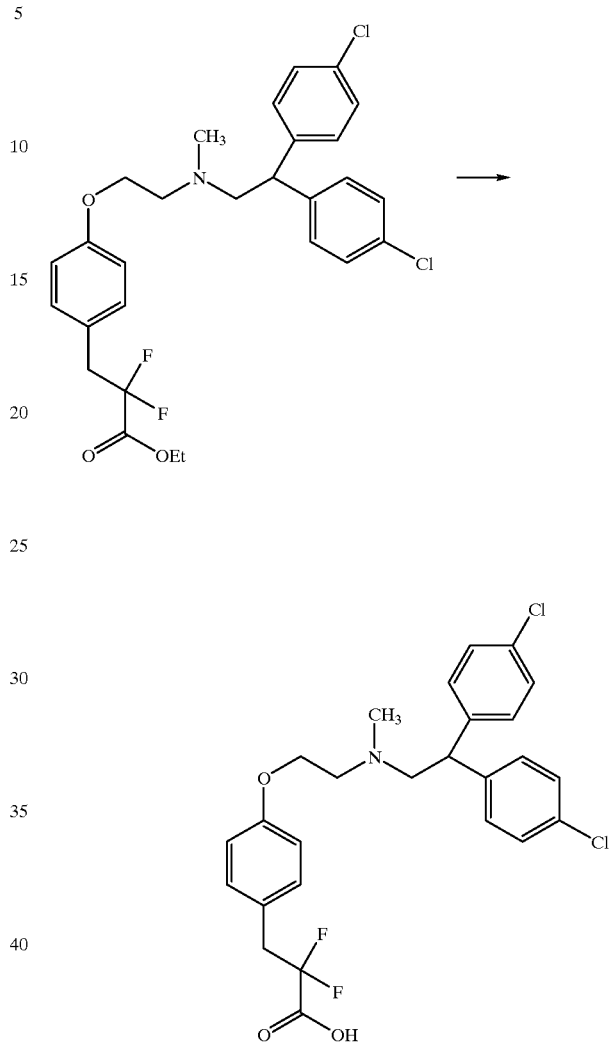

A solution of 3-[4-[2-[N-[2-bis-(chlorophenyl)ethyl]-N-methylamino]ethoxy]phenyl]-2,2-difluoropropanoic acid methyl ester (1.15 g, 2.14 mmol) in a mixture of ethanol (9 ml) and water (3 ml) was treated with potassium hydroxide (0.28 g, 5.0 mmol) and the resulting mixture was stirred at 22° C. for 4 hours. The mixture was then cooled to 0° C. and adjusted to pH 3.0 with 1N hydrochloric acid and concentrated in vacuo. The residue was extracted twice with dichloromethane and the combined organic phases were washed with brine and dried (magnesium sulfate). Evaporation of the solvent and recrystallization of the solid residue from ethyl acetate-hexane gave 1.09 g (quantitative) of the title material as a white solid: mp 74–78° C.

Anal. Calcd. for $C_{26}H_{25}Cl_2F_2NO_3$: C, 61.43; H, 4.96; N, 2.76. Found: C, 61.02; H, 5.63; N, 2.49.

83
N-Methoxy-N-methyl 3-[4-[2-[N-[2-Bis-(4-chlorophenyl)ethyl]-N-methylamino]ethoxy]phenyl]-2,2-difluoropropionamide

84
4-[4-[2-[N-[2-Bis-(4-chlorophenyl)ethyl]-N-methylamino]ethoxy]phenyl]-2,2-difluoro-1-methoxy-2-butanone

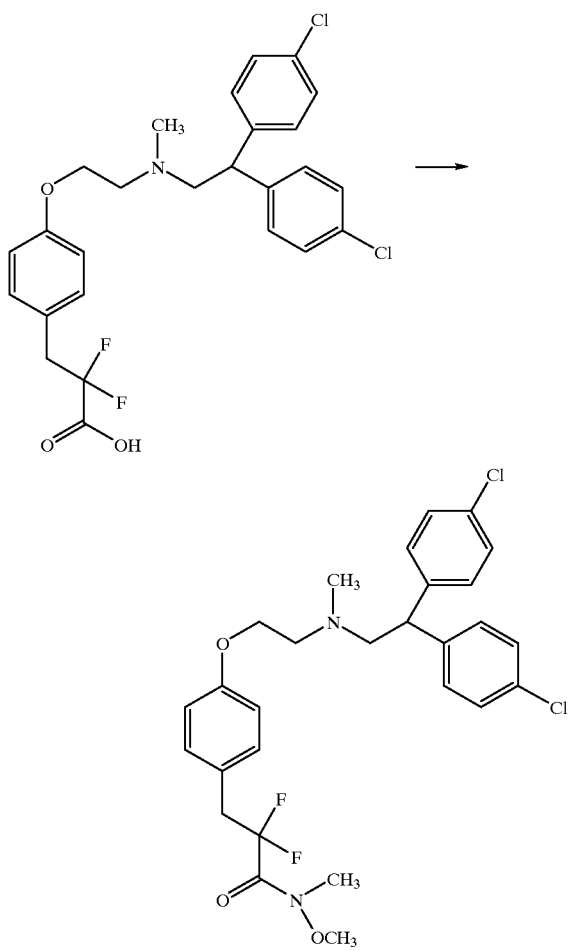

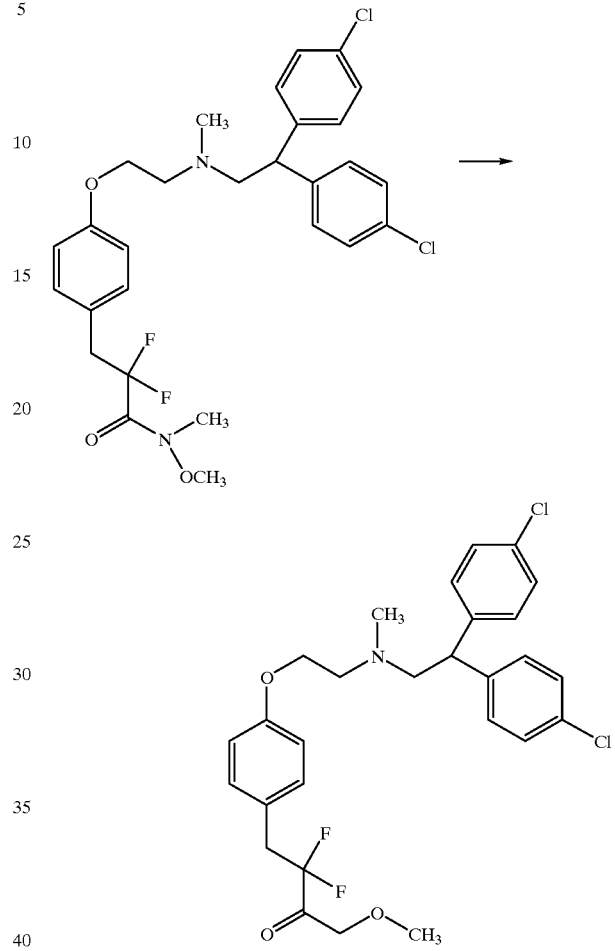

A solution of 3-[4-[2-[N-2-bis(4-chlorophenyl)ethyl]-N-methylamino]ethoxy]phenyl]-2,2difluoropropanoic acid (1.09 g, 2.0 mmol) in dichloromethane (10 ml) was cooled to −25° C. and treated with N-methylmorpholine (0.25 g, 2.46 mmol) followed by isobutyl chloroformate (0.33 g, 2.4 mmol). After 5 min, the mixture was treated with a suspension of N,O-dimethylhydroxylamine hydrochloride (0.26 g, 2.7 mmol) and N-methylmorpholine (0.28 g, 2.7 mmol) in dichloromethane (9 ml). The resulting mixture was allowed to warm up to 22° C. and stirred for 2.5 hours. The reaction was then quenched by addition of saturated aqueous sodium bicarbonate and dichloromethane. The organic phase was washed with brine, dried (magnesium sulfate) and evaporated. Chromatography of the residue on silica gel (elution hexane-ethyl acetate, 6:4) gave 0.95 g (86%) of the title material as an oil.

Anal. Calcd. for $C_{28}H_{30}Cl_2F_2N_2O_3$: C, 60.99; H, 5.48; N, 5.08. Found: C, 61.0; H, 5.59; N, 5.13.

A solution of methoxymethyltributyltin (0.296 g, 0.88 mmol) in tetrahydrofuran (2 ml) at −78° C. was treated with n-butyllithium (0.40 ml of a 2.08 M solution in hexane, 0.83 mmol). After 10 min, a solution of N-methoxy-N-methyl 3-[4-[2-[N-[2-bis-(4-chlorophenyl)ethyl]-N-methylamino]ethoxy]phenyl]-2,2-difluoropropiona-mide (0.199 g, 0.36 mmol) in tetrahydrofuran (1 ml) was added and the resulting mixture was stirred at −78° C. for 15 minutes. The temperature of the reaction mixture was then allowed to reach 22° C. over 20 minutes and the reaction was quenched by the addition of saturated aqueous sodium bicarbonate and dichloromethane. The organic phase was washed with brine, dried (magnesium sulfate) and evaporated. Chromatography of the residue on silica gel (elution toluene-tetrahydrofuran, 85:15) gave 0.150 g (80%) of the title material as oil. The hydrochloride salt was obtained as a white solid: mp 53–62° C.

Anal. Calcd. for $C_{28}H_{29}Cl_2F_2NO_3 \cdot HCl \cdot 0.4 \, H_2O$: C, 57.97; H, 5.35, N 2.41. Found: C, 58.10; H, 5.67; N, 2.55.

Example 10

4-[4-[2-[N-[2-Bis-(4-chlorophenyl)ethyl]-N-methylamino]ethoxy]phenyl]-2,2-difluoro-1-[4-(4,5-dihydro-2-oxazolyl)phenoxy]-2-butanone

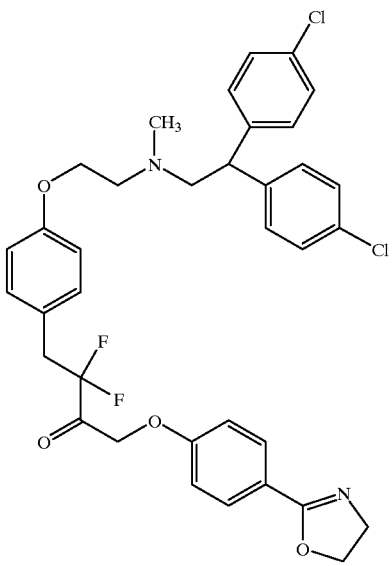

2-[4-(Tributylstannylmethoxy)phenyl]-4,6-dihydrooxazole

4-[4-[2-[N-[2-Bis-(4-chlorophenyl)ethyl]-N-methylamino]ethoxy]phenyl]-2,2-difluoro-1-[4-(4,5-dihydro-2-oxazolyl)phenoxy]-2-butanone

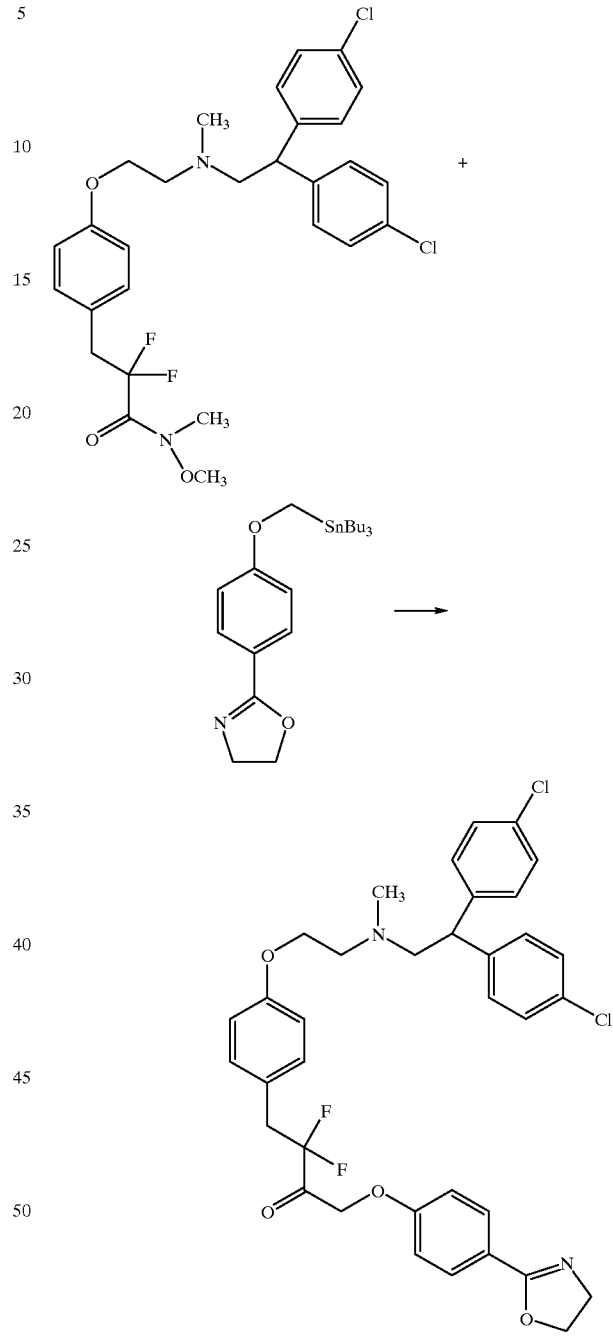

A solution of 4-(4,5-dihydro-2-oxazolyl)phenol (0.145 g, 0.89 mmol) (G. D. Diana, et al., *J. Med. Chem.*, 1985, 28, 1906–1910) and iodomethyltributyltin (0.52 g, 1.2 mmol) (D. E. Seitz, et al., *Synthetic Commun.*, 1983, 13, 129–134) in N,N-dimethylformamide (3 ml) was treated with powdered potassium carbonate (0.31 g, 2.2 mmol) and the resulting mixture was heated at 70° C. for 15 hours. The reaction mixture was then diluted with ethyl acetate-hexane (6:4) washed with water, brine and dried (magnesium sulfate). Evaporation of the solvent and chromatography of the residue on silica gel (elution toluene-ethyl acetate, 8:2) gave 0.360 g (86%) of the title material as an oil.

A solution of 2-[4-(tributylstannylmethoxy)phenyl]-4,5-dihydrooxazole (0.330 g, 0.71 mmol) in tetrahydrofuran (2 ml) at −78° C. was treated with 0.33 ml (0.68 ml) of a 2.08 M solution of butyllithium in hexane. After 10 min, a solution of N-methoxy-N-methyl 3-[4-[2-[N-[2-bis-(4-chlorophenyl)ethyl]-N-methylamino]ethoxy]phenyl]-2,2-difluoropropionamide (0.170 g, 0.31 mmol) in tetrahydrofuran (1 ml) was added and resulting mixture was stirred at −78° C. for 15 minutes. The temperature of the mixture was then warmed to 20° C. over 20 minutes and the reaction was quenched by addition of saturated aqueous sodium bicarbonate and ethyl acetate. The organic phase was washed with brine, dried (magnesium sulfate) and evaporated. Chromatography of the residue on silica gel (elution ethyl acetate-methanol 0–2%) gave 0.107 g (52%) of the title material as a white glassy solid.

HRMS (ESI⁺) (M+H)⁺ calcd: 667.19418 Found: 667.1948, δ=−0.9 ppm.

Example 11

4-[4-[2-[N-[2-Bis-(4-chlorophenyl)ethyl]-N-methylamino]ethoxy]phenyl]-2,2-difluoro-1-[4-(4,5-dihydro-4,4-dimethyl-2-oxazolyl)phenoxy]-2-butanone

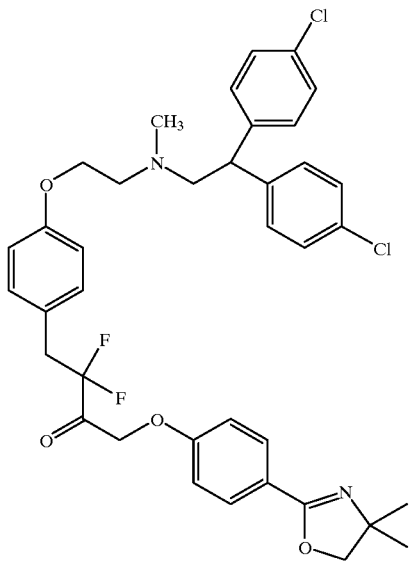

+

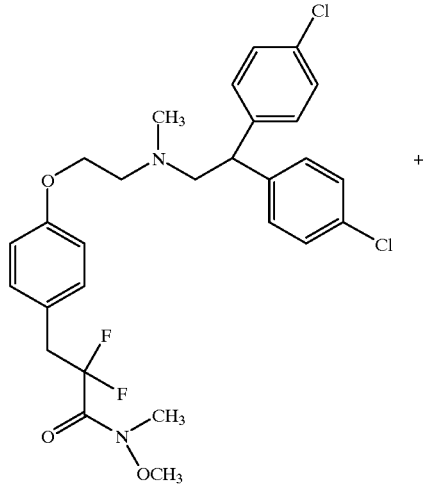

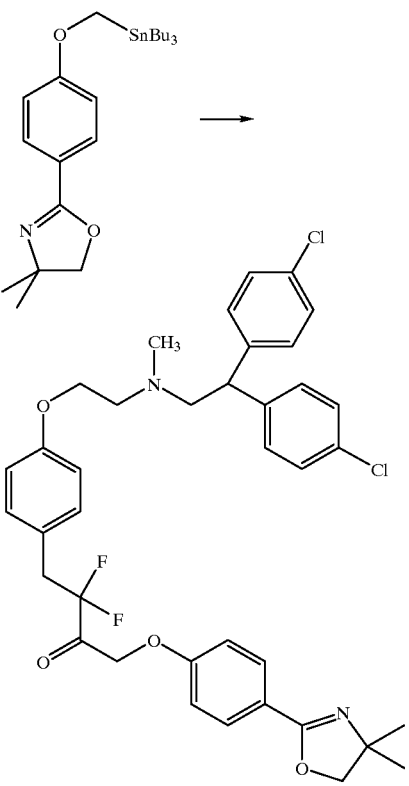

Reaction of N-methoxy-N-methyl 3-[4-[2-[N-[2-bis-(4-chlorophenyl)ethyl]-N-methylamino]ethoxy]phenyl]-2,2-difluoropropionamide (0.20 g, 0.36 mmol) with 2-[4-(tributylstannylmethoxy)phenyl]-4,4-dimethyl-4,5-dihydrooxazole (0.391 g, 0.79 mmol) using the conditions described in Example 9 gave 0.108 g (43%) of the title material as a syrup.

MS (ESI⁺) (m/z): 695 (M+H)⁺.

Example 12

[4-[4-[2-[N-[2-Bis-(4-chlorophenyl)ethyl]-N-methylamino]ethoxy]phenyl]-2,2-difluoro-1-[4-(2-aminocarboxyethyl)phenoxy]-2-butanone, dihydrochloride salt

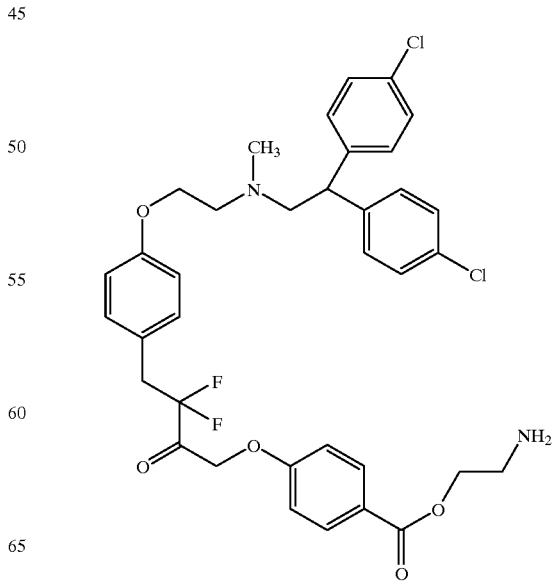

89
-continued

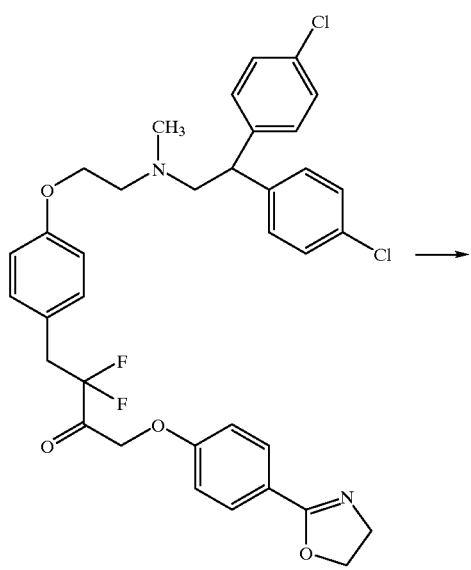

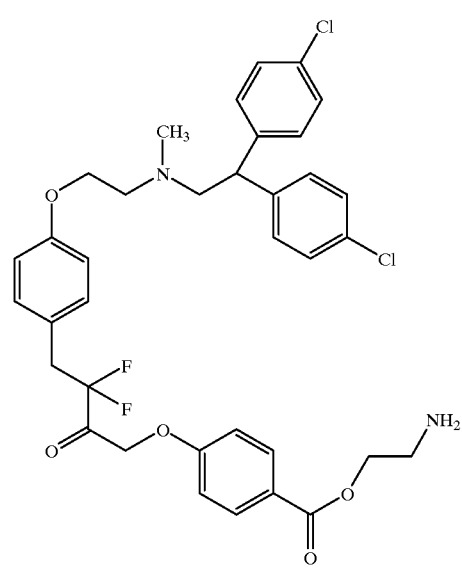

A solution of 4-[4-[2-[N-[2-bis-(4-chlorophenyl)ethyl]-N-methylamino]ethoxy]phenyl]-2,2-difluoro-1-[4-(4,5-dihydro-2-oxazolyl)phenoxy]-2-butanone (0.071 g, 0.4 mmol) in a mixture of tetrahydrofuran (3 ml) and 1N aqueous hydrochloric acid (0.7 ml) was heated in a sealed tube at 100° C. for 15 minutes. The solvent was then evaporated in vacuo and the residue was extracted with boiling acetonitrile. Evaporation of the acetonitrile extract gave 0.060 g (72%) of the title material as a glassy solid.

MS (ESI⁺) (m/z): 685, (M+H)⁺.

Example 13
4-[4-[2-[N-[2-Bis-(4-chlorophenyl)ethyl]-N-methylamino]ethoxy]phenyl]-2,2-difluoro-1-(4-carboxyphenoxy)-2-butanone

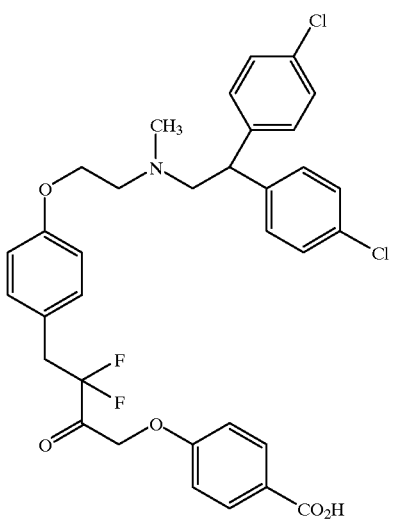

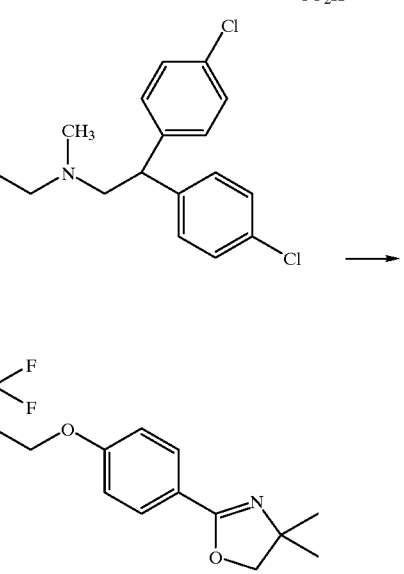

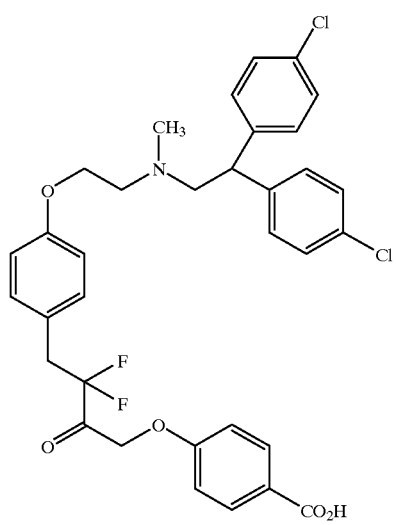

A solution of 4-[4-[2-[N-[2-bis-(4-chlorophenyl)ethyl]-N-methylamino]ethoxy]phenyl]-2,2-difluoro-1-[4-(4,5-dihydro-4,4-dimethyl-2-oxazolyl)phenoxy]-2-butanone (0.075 g, 0.11 mmol) in dioxane (1.5 ml) was treated with 2.0 ml of 4.8N aqueous hydrochloric acid and the resulting mixture was heated at 100° C. in a sealed tube for 6 hours. The cooled mixture was concentrated in vacuo and the residue was dissolved in a small amount of tetrahydrofuran and water. After adjusting to pH 4, the mixture was diluted with dichloromethane and washed with water. The organic phase was dried, concentrated in vacuo and chromatographed on silica gel plates (elution dichloromethane-methanol, 9:1) to give 0.015 g (20%) of the title material as an amorphous solid. The hydrochloride salt was prepared and obtained as a white solid.

MS (ESI$^+$) (m/z) 642 (M+H)$^+$.

Example 14

(2R and 2S)-3-[4-[3-[N-[2-Bis-(4-chlorophenyl)ethyl]-N-methylamino]propyl]phenoxy]-1-(4-carboxyphenoxy)-2-(2-oxopropionamido)propane

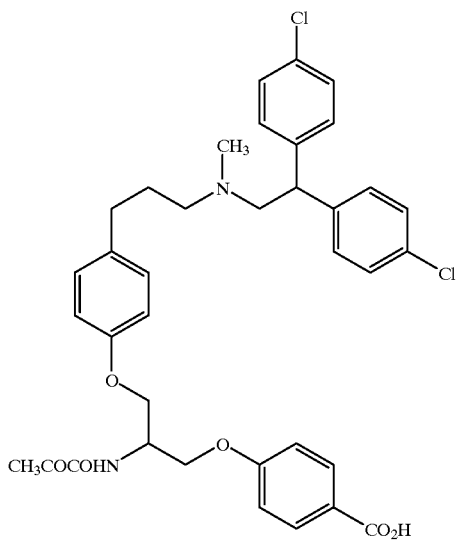

(2R and 2S)-3-[4-[3-[N-[2-Bis-(4-chlorophenyl)ethyl]-N-methylamino]propyl]phenoxy]-1-[4-(tert-butoxycarbonyl)phenoxy]-2-(2-oxopropionamido)propane

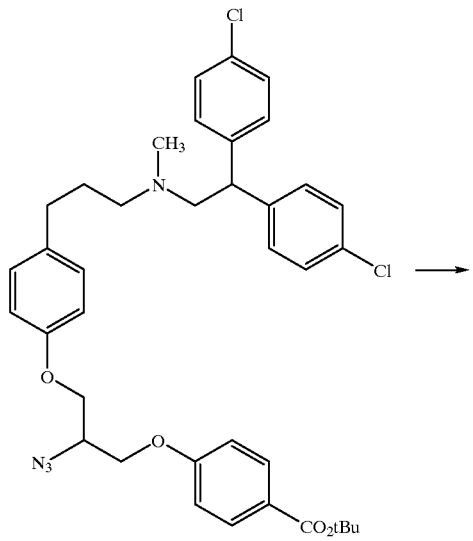

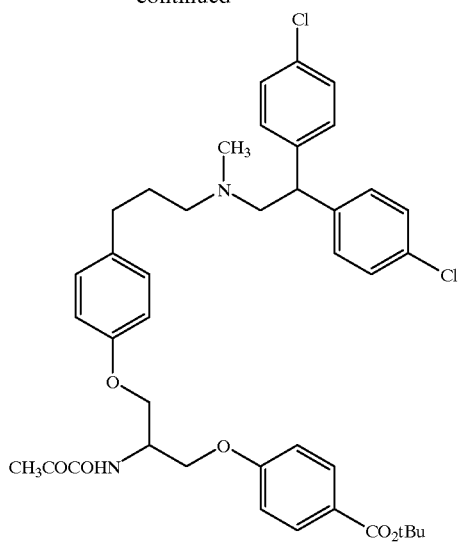

A solution of (2R and 2S)-3-[4-[3-[N-[2-bis-(4-chlorophenyl)ethyl]-N-methyl-amino]propyl]phenoxy]-1-[4-(tert-butoxycarbonyl)phenoxy]-2-azidopropane (3.04 g, 4.4 mmol) in a mixture of tetrahydrofuran and water was reduced as described in Example 8 with triphenylphosphine (3.4 g, 13.1 mmol). The crude product obtained after work-up was diluted with dichloromethane (30 ml) cooled to 0° C. and treated with pyridine (0.3 ml) followed by 2-oxopropionyl chloride (0.5 g, 4.6 mmol). After 30 minutes at 0–5° C., the reaction mixture was diluted with ethyl acetate, washed with saturated sodium bicarbonate, brine and dried (magnesium sulfate). Evaporation of the solvent and chromatography of the residue on silica gel (elution toluene-ethyl acetate, 75:25) gave 0.191 g (6%) of the title material as an oil.

$^1$H NMR 400 MHz (DMSO-d$_6$) δ (ppm): 1.53 (9H, s, tBu), 1.57 (2H, m, CH$_2$), 2.16 (3H, s, NCH$_3$), 2.31 (4H, m, 2×CH$_2$), 2.37 (3H, s, COCH$_3$), 2.85 (2H, d, J=8.1 Hz, NCH$_2$), 4.1–4.3 (5H, m, 2×OCH$_2$ and CH), 4.47 (1H, m, CH), 6.84 (2H, d, J=8.6 Hz, aromatic), 6.98 (2H, d, J=8.6 Hz, aromatic), 7.03 (2H, d, J=9.0 Hz, aromatic), 7.33 (8H, s, aromatic), 7.84 (2H, d, J=9.0 Hz, aromatic), 8.84 (1H, d, J=8.5 Hz, NH).

MS (ESI$^+$) (m/z): 733 (M+H)$^+$ (2R and 2S)-3-[4-[3-[N-[2-Bis-(4-chlorophenyl)ethyl]-N-methylamino]propyl]phenoxy]-1-(4-carboxyphenoxy)-2-(2-oxopropionamido)propane

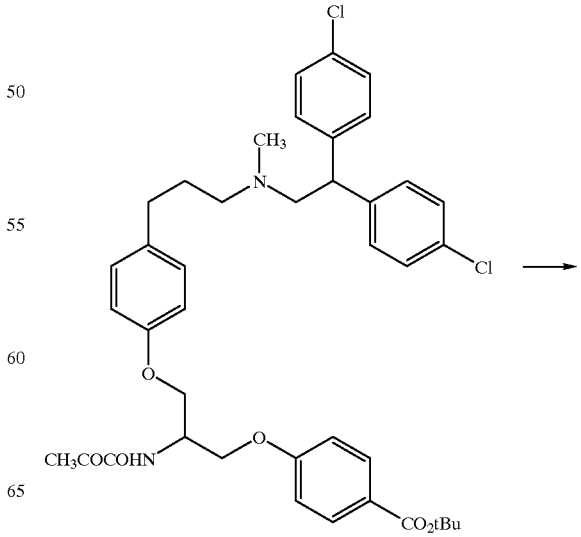

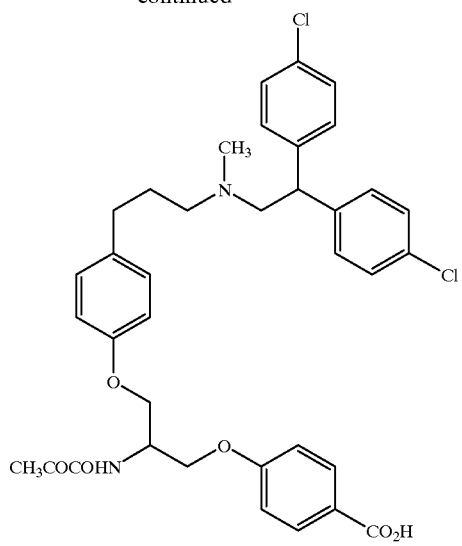

A solution of (2R and 2S)-3-[4-[3-[N-[2-bis-(4-chlorophenyl)ethyl]-N-methylamino]propyl]phenoxy]-1-(4-(tert-butoxycarbonyl)phenoxy])-2-(2-oxopropionamido) propane (0.158 g, 0.21 mmol) in dichloromethane (10 ml) was treated at 22° C. with trifluoroacetic acid (1.5 ml) and the resulting mixture was stirred for 2.5 hours. The solvent and the excess reagent were then evaporated in vacuo. The residue was diluted with dichloromethane, washed with pH 6 phosphate buffer, dried (magnesium sulfate) and concentrated. Chromatography of the residue on silica gel (elution toluene-ethyl acetate, 1:1) gave 0.099 g (68%) of the title material as a syrup. The hydrochloride salt was prepared as usual and obtained as an amorphous solid.

$^1$H NMR (free amine) 400 MHz (DMSO-$d_6$) δ (ppm): 1.57 (2H, m, CH$_2$), 2.16 (3H, s, NCH$_3$), 2.30 (4H, m, 2×CH$_2$), 2.37 (3H, s, COCH$_3$), 2.85 (2H, d, J=8.2 Hz, NCH$_2$), 4.1–4.3 (5H, m, 2×OCH$_2$ and CH), 4.47 (1H, m, CH), 6.84 (2H, d, J=8.5 Hz, aromatic), 6.99 (4H, m, aromatic), 7.33 (8H, s, aromatic), 7.87 (2H, d, J=9.1 Hz, aromatic), 8.91 (1H, d, J=8.7 Hz, NH).

HRMS (ESI$^+$) Calcd. for C$_{37}$H$_{39}$N$_2$O$_6$$^{35}$Cl$_2$ [MH]$^+$: 677.21851 Found: 677.21840, δ=0.2 ppm.

Example 15
(3R and 3S)-3-[4-[3-[N-[2-Bis-4-chlorophenyl) ethyl]-N-methylamino]propyl]phenoxy]-3-methoxy-1-(4-carboxyphenoxy)-2-propanone

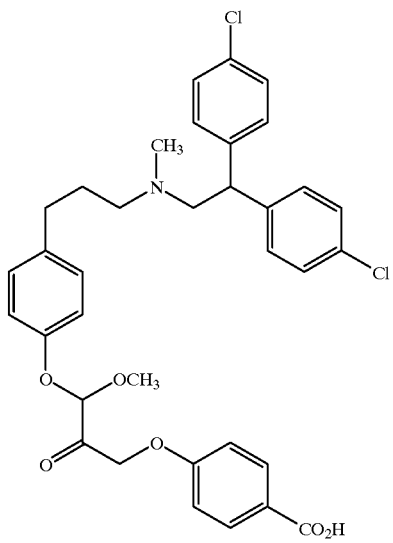

Methyl (2R and 2S)-2-[4-[3-[N-[2-Bis-(4-chlorophenyl)ethyl]-N-methylamino]propyl] phenoxy]-2-methoxyacetate

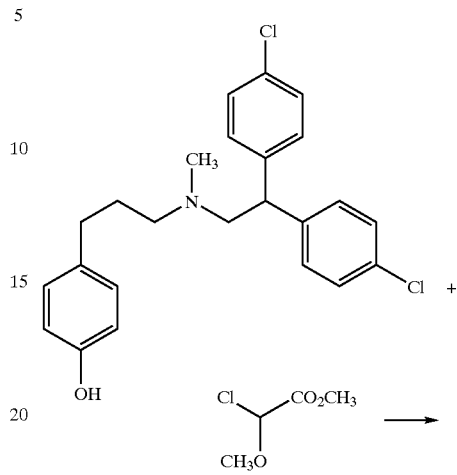

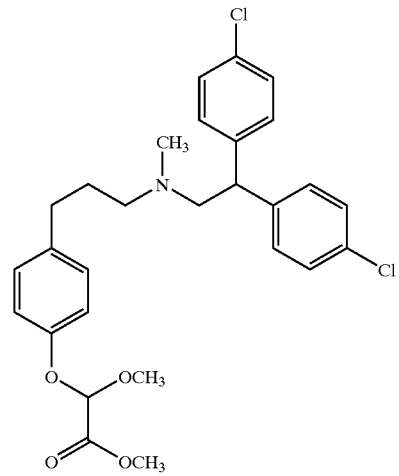

A solution of 4-[3[N-[2-bis-(4-chlorophenyl)ethyl]N-methylamino]propyl]phenol (2.41 g, 5.8 mmol) in ether (25 ml) was treated with triethylamine (1.1 ml, 7.9 mmol) followed by chloromethoxyacetic acid methyl ester (1.0 g, 7.3 mmol) [H. Grosz and J. Freiberg, Chem. Ber. (1996) 99, 3260] and the resulting mixture was heated under reflux for 16 hours. The solid formed was filtered and washed with ether. The filtrate was washed with saturated sodium bicarbonate, dried (magnesium sulfate) and evaporated. Chromatography of the residue on silica gel (elution hexane-ethyl acetate, 8:3) gave 3.0 g (100%) of the title material as a clear oil.

$^1$H NMR 400 MHz (C$_6$D$_6$) δ (ppm): 1.63 (2H, m, CH$_2$), 2.09 (3H, s, NCH$_3$), 2.26 (2H, t, J=6.8 Hz, CH$_2$), 2.42 (2H, t, J=7.6 Hz, CH$_2$), 2.66 (2H, d, J=8.0 Hz, NCH$_2$), 3.39 (6H, s, 2×OCH$_3$), 3.90 (1H, t, J=8.0 Hz, CH), 5.55 (1H, s, CH), 6.88 (4H, d, J=8.7 Hz, aromatic), 6.98 (2H, d, J=8.7 Hz, aromatic), 7.23 (6H, m, aromatic).

Anal. Calcd. for C$_{28}$H$_{31}$Cl$_2$NO$_4$: C, 65.12; H, 6.05; N, 2.71. Found: C, 65.14; H, 6.17; N, 2.79.

(2R and 2S)-2-[4-[3-[N-[2-Bis-(4-chlorophenyl)ethyl]-N-methylamino]propyl]phenoxy]-2-methoxyacetic acid, hydrochloride salt

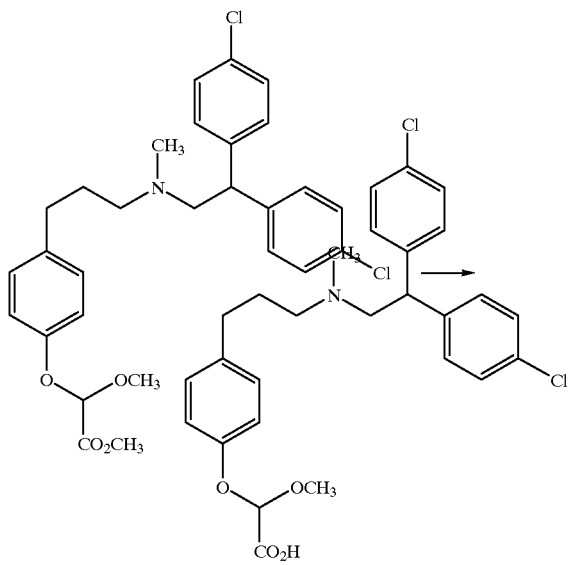

A solution of methyl (2R and 2S)-2-[4-[3-[N-[3-bis-(4-chlorophenyl)ethyl]-N-methylamino]propyl]phenoxy]-2-methoxyacetate (1.0 g, 1.94 mmol) in 80% aqueous ethanol (20 ml) was treated with potassium hydroxide (0.15 g) in water (1 ml) and the resulting mixture was stirred at 25° C. for 1.5 hour. The reaction mixture was then partitioned between water and ethyl acetate and the pH of the aqueous phase was adjusted to 3.0. The organic phase was then washed with brine, dried (magnesium sulfate) and concentrated to give 0.86 g (82%) of the title salt as a white amorphous solid.

$^1$H NMR 400 MHz (CD$_3$OD) δ (ppm): 2.0 (2H, m, CH$_2$), 2.64 (2H, t, J=7.4 Hz, CH$_2$), 2.90 (3H, s, NCH$_3$), 3.17 (2H, broad t, CH$_2$), 3.48 (3H, s, OCH$_3$), 3.9 (2H, broad d, CH$_2$), 4.49 (1H, t, J=8.1 Hz, CH), 5.48 (1H, s, CH), 7.07 (2H, d, J=8.6 Hz, aromatic), 7.17 (2H, d, J=8.6 Hz, aromatic), 7.4 (8H, m, aromatic).

Anal. Calcd. for C$_{27}$H$_{29}$Cl$_2$NO$_4$·HCl: C, 60.18, H5.61; N, 2.60. Found: C, 59.69; H, 5.49; N, 2.64.

(2R and 2S)-2-[4-[3-[N-[2-Bis-(4-chlorophenyl)ethyl]-N-methylamino]propyl]phenoxy]-2-methoxy-N-methoxy-N-methylacetamide

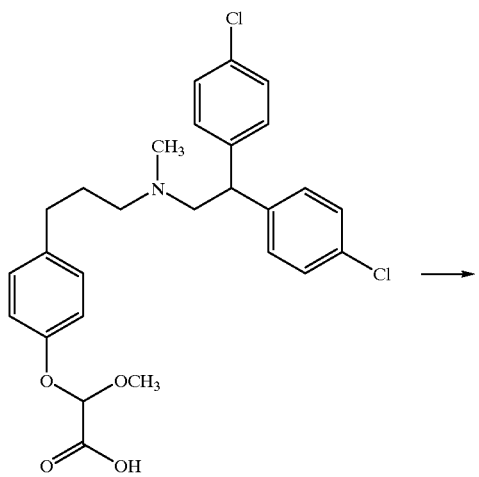

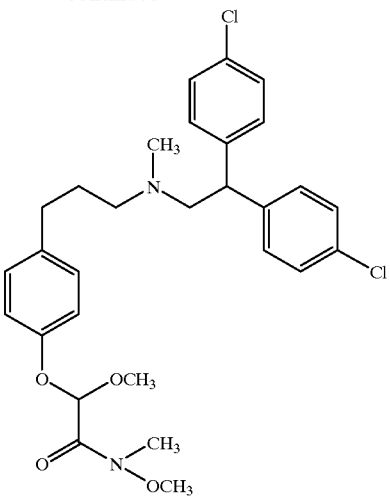

A solution of (2R and 2S)-2-[4-[3-[N-[2-bis-(4-chlorophenyl)ethyl]-N-methylamino]propyl]phenoxy]-2-methoxyacetic acid, hydrochloride salt (0.80 g, 1.48 mmol) in dichloromethane (15 ml) was treated with oxalyl chloride (0.25 ml, 2.9 mmol) and a trace of N,N-dimethylformamide and the resulting mixture was stirred at 22° C. for 2.5 hours. The solvent and excess reagents were evaporated in vacuo and the residue was diluted with dichloromethane (15 ml) and cooled to 0–50° C. Then N,O-dimethylhydroxylamine hydrochloride (0.18 g, 1.8 mmol) followed by pyridine (0.4 ml) were added and the resulting mixture was stirred at 22° C. for 30 minutes. The reaction mixture was then diluted with ethyl acetate, washed with sodium bicarbonate, brine and dried (magnesium sulfate). Evaporation of the solvent and chromatography of the residue on silica gel (elution hexane-ethyl acetate, 1:1) gave 0.30 g (37%) of the title amide as an oil.

$^1$H NMR 400 MHz (C$_6$D$_6$) δ (ppm): 1.64 (2H, m, CH$_2$), 2.10 (3H, s, NCH$_3$), 2.28 (2H, t, J=6.9 Hz, CH$_2$), 2.44 (2H, t, J=7.7 Hz, CH$_2$), 2.67 (2H, d, J=8.2 Hz, NCH$_2$), 2.9 (3H, broad s, NCH$_3$), 3.25 and 3.59 (2×3H, 2 broad s, 2×OCH$_3$), 3.25 and 3.59 (2×3H, 2 broad s, 2×OCH$_3$), 3.9 (1H, t, J=8.2 Hz, CH), 6.12 (1H, broad s, CH), 6.89 (4H, d, J=8.3 Hz, aromatic), 7.03 (2H, d, J=8.7 Hz, aromatic), 7.24 (4H, d, J=8.3 Hz, aromatic) 7.3 (2H, overlapping with C$_6$H$_6$, aromatic).

HRMS (ESI$^+$) calcd for C$_{29}$H$_{35}$N$_2$O$_4$$^{35}$Cl$_2$ [MH]$^+$: 545.19738 Found: 545.19792, δ−1.0 ppm

1,1-Dimethylethyl 4-(tributylstannylmethoxy)benzoate

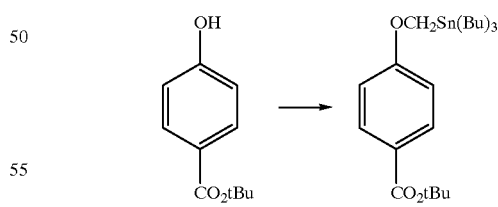

A solution of 1,1-dimethylethyl 4-hydroxybenzoate (0.20 g, 1.04 mmol) in N,N-dimethylformamide (4 ml) was treated with powdered anhydrous potassium carbonate (0.4 g) followed by iodomethyltributyltin (0.60 g, 1.4 mmol) [D. E. Seitz, et al, *Synth. Commun.* (1983) 13, 129–134] and the resulting mixture was stirred at 65° C. for 1 hour. The cooled reaction mixture was diluted with a mixture of hexane and ethyl acetate (9:1), washed with water, brine and dried (magnesium sulfate). Evaporation of the solvent and chromotography of the residue on silica gel (elution hexane-toluene, 1:1) gave 0.494 g (96%) of the title material as an oil.

¹H NMR 400 MHz (CDCl₃) δ (ppm): 0.9 (9H, t, J=7.3 Hz, 3×CH₃), 0.98 (6H, broad t, CH₂), 1.32 (6H, m, 3×CH₂), 1.53 (6H, m, 3×CH₂), 1.59 (9H, s, t-Bu), 4.21 (2H, s, OCH₂), 6.93 (2H, d, J=8.8 Hz, aromatic), 7.93 (2H, d, J=8.8 Hz, aromatic).

(3R and 3S)-3-[4-[3-[N-[2-Bis-(4-chlorophenyl) ethyl]-N-methylamino]propyl]phenoxy]-3-methoxy-1-[4-(tert-butoxycarbonyl)phenoxy]-2-propanone

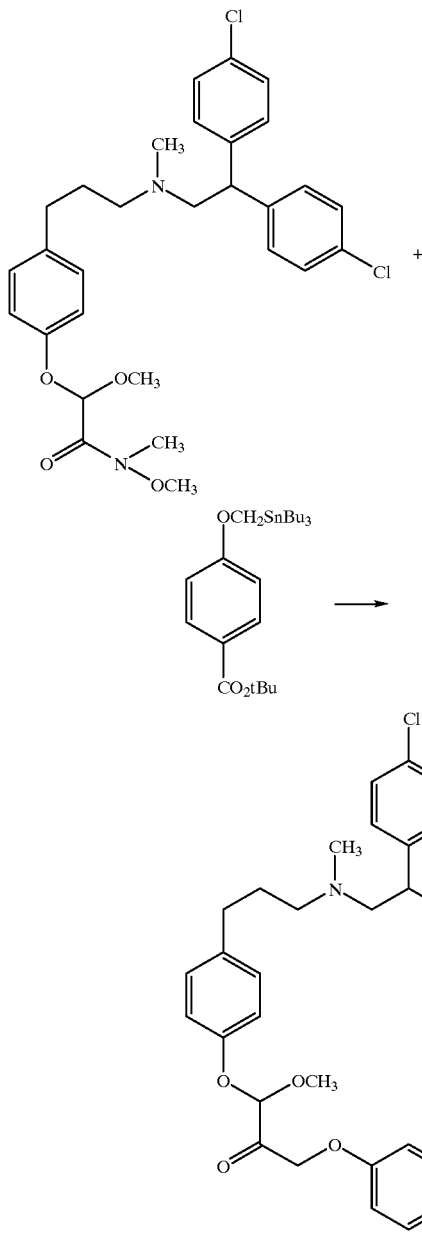

A solution of 1,1-dimethylethyl 4-(tributylstannylmethoxy)benzoate (0.29 g, 0.58 mmol) in dry tetrahydrofuran (5 ml) was cooled to −100° C. and treated with 0.36 ml of 1.6M butyllithium (0.58 mmol) in hexane. After 10 minutes at −100° C., a solution of (2R and 2S)-2-[4-[3-[N-[2-bis-(4-chlorophenyl)ethyl]-N-methylamino]propyl]phenoxy]-2-methoxy-N-methoxy-N-methylacetamide (0.30 g, 0.55 mmol) in tetrahydrofuran (5 ml) was added dropwise over 5 minutes. After 10 minutes at −100° C., the temperature of the reaction mixture was allowed to warm up to 22° C. over 1 hour. The reaction mixture was then quenched by addition of saturated sodium bicarbonate and ethyl acetate. The organic phase was washed with brine, dried (magnesium sulfate) and concentrated. Chromatography of the residue on silica gel (elution hexane-ethyl acetate, 7:3) gave 0.147 g (39%) of the title material as an oil.

¹H NMR 400 MHz (C₆D₆) δ (ppm): 1.58 (9H, s, t-Bu), 1.64 (2H, m. CH₂), 2.12 (3H, s, NCH₃), 2.29 (2H, t, J=6.8 Hz, CH₂), 2.44 (2H, t, J=7.6 Hz, CH₂), 2.69 (2H, d, J=8.0 Hz, NCH₂), 3.18 (3H, s, OCH₃), 3.92 (1H, t, J=8.0 Hz, CH), 4.83 (2H, AB system, J$_{AB}$=18.3 Hz, Δνν=21.6 Hz, OCH₂), 5.16 (1H, s, CH), 6.81 (2H, d, J=8.8 Hz, aromatic), 6.90 (4H, d, J=8.5 Hz, aromatic), 6.97 (2H, d, J=8.6 Hz, aromatic), 7.07 (2H, d, J=8.6 Hz, aromatic), 7.24 (4H, d, J=8.5 Hz, aromatic), 8.18 (2H, d, J=8.8 Hz, aromatic).

HRMS (ESI⁺) calcd for C₃₉H₄NO₆³⁵Cl₂ [MH]⁺: 692.25458 Found: 692.25310, δ 2.1 ppm (3R and 3S)-3-[4-[3-[N-[2-Bis-(4-chlorophenyl) ethyl]-N-methylamino]propyl]phenoxy]-3-methoxy-1-[4-carboxyphenoxy)-2-propanone, trifluoroacetic salt

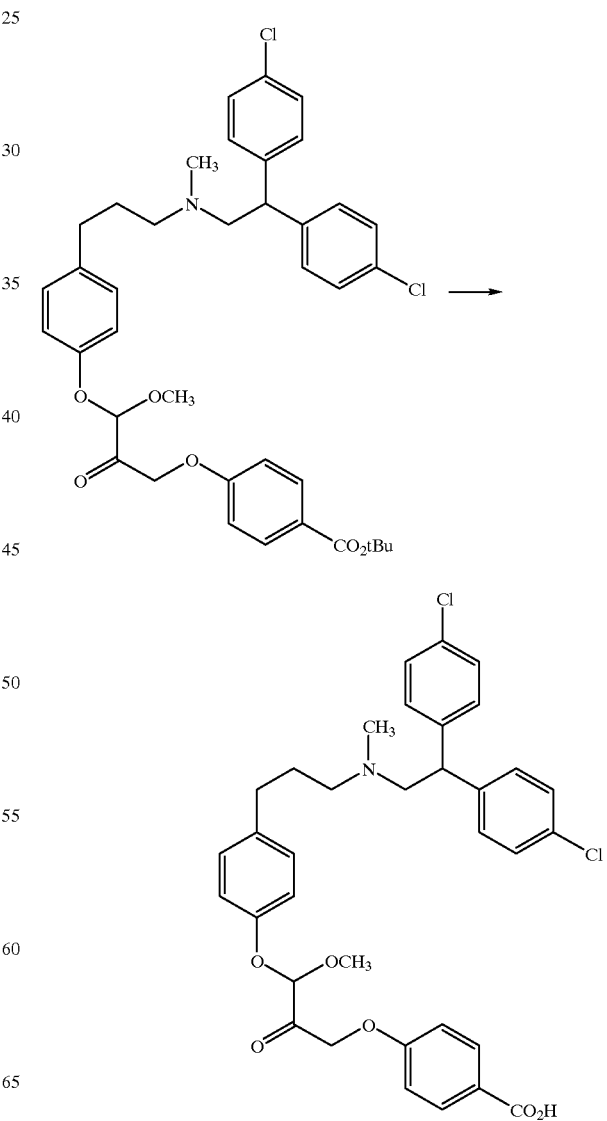

A solution of (3R and 3S)-3-[4-[3-[N-2-bis-(4-chlorophenyl)ethyl]-N-methylamino]propyl]phenoxy]-3-methoxy-1-[4-(tert-butoxycarbonyl)phenoxy]-2-propanone (0.105 g, 0.15 mmol) in dichloromethane (5 ml) was treated at 22° C. with trifluoroacetic acid (1 ml). After 1 hour, the solvent and excess reagent were evaporated in vacuo. The residue was dissolved in a mixture of water and acetonitrile and lyophilized to give 0.113 g (quantitative) of the title trifluoroacetate salt as a white amorphous solid.

$^1$H NMR 400 MHz (DMSO-$d_6$) δ (ppm): 1.8–2.05 (2H, m, $CH_2$), 2.79 and 2.80 (3H, 2s, $NCH_3$), 2.95–3.2 (2H, m $CH_2$), 3.46 (3H, s, $OCH_3$), 3.75 (2H, m, $NCH_2$), 4.03 (2H, m, $NCH_2$), 4.61 (1H, broad t, J=7.5 Hz, CH), 5.28 (2H, ABq, $J_{AB}$=18.7 Hz, Δν=9.32 Hz, $OCH_2$), 5.76 (1H, s, CH), 6.98 (2H, d, J=8.9 Hz, aromatic), 7.07 (2H, d, J=8.6 Hz, aromatic) 7.18 (2H, d, J=8.6 Hz, aromatic), 7.5 (8H, m, aromatic), 7.87 (2H, d, J=8.9 Hz, aromatic).

HRMS (ESI$^-$) calcd for $C_{35}H_{34}O_6N^{35}Cl_2$ [M−H]$^-$: 634.17633 Found: 634.17940, δ 4.8 ppm

TABLE A

| EXAMPLE | STRUCTURE | ANALYSIS |
|---|---|---|
| 16 | 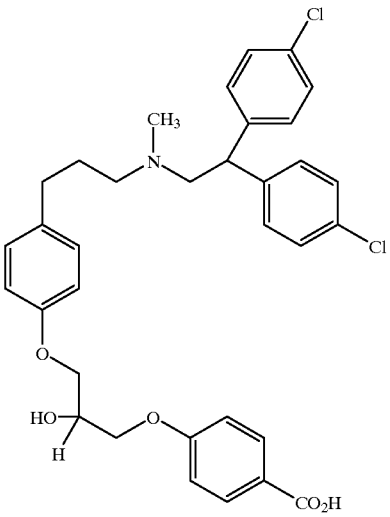 | $C_{34}H_{35}Cl_2NO_5$·HCl<br>MS (ESI$^+$) (m/z):<br>m/e 608 (M + H)$^+$ |
| 17 | 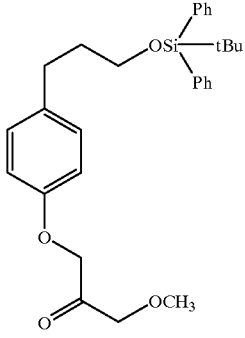 | $C_{29}H_{36}O_4Si$·0.2 $H_2O$<br>Calcd: C 72.52, H 7.64<br>Found: C 72.51, H 7.52 |

TABLE A-continued
| EXAMPLE | STRUCTURE | ANALYSIS |
|---|---|---|
| 18 | 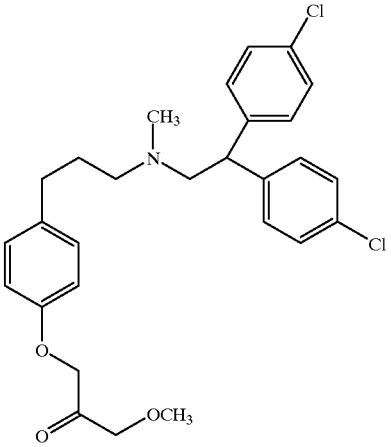 | $C_{28}H_{31}Cl_2NO_3 \cdot HCl \cdot 0.7 H_2O$<br>C 61.20 H 6.13, N 2.55<br>Found: C 61.22, H 6.05, N 2.58 |
| 19 | 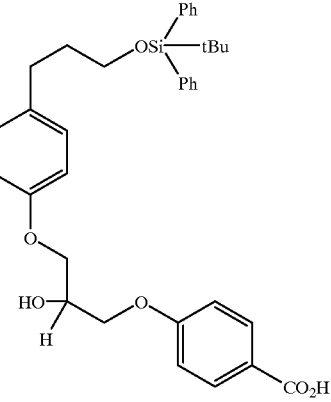 | $C_{35}H_{40}O_6Si$<br>Calcd: C 71.89, H 6.89<br>Found: C 71.85, H 6.90 |
| 20 | 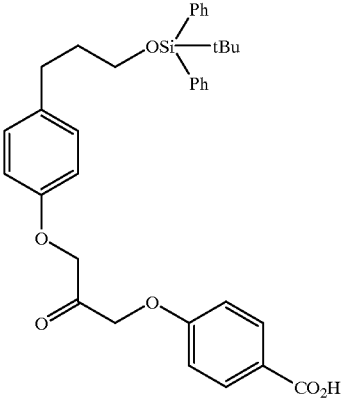 | $C_{35}H_{38}O_6Si$<br>Calcd: C 72.14, H 6.57<br>Found: C 72.07, H 6.65 |

TABLE A-continued
| EXAMPLE | STRUCTURE | ANALYSIS |
|---|---|---|
| 21 | 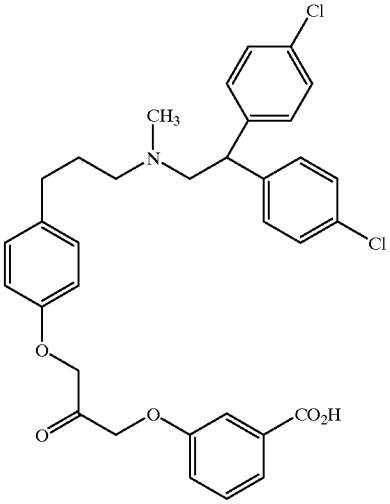 | $C_{34}H_{33}Cl_2NO_5 \cdot HCl \cdot 1.8$ $H_2O$<br>Calcd: C 60.46, H 5.61, N 2.07<br>Found: C 60.49, H 5.19, N 2.00 |
| 22 | 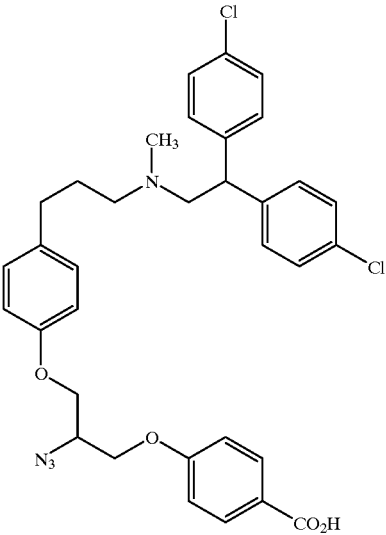 | $C_{34}H_{34}Cl_2N_4O_4$<br>MS (ESI$^+$) (m/z): 633 (MH$^+$) |
| 23 | 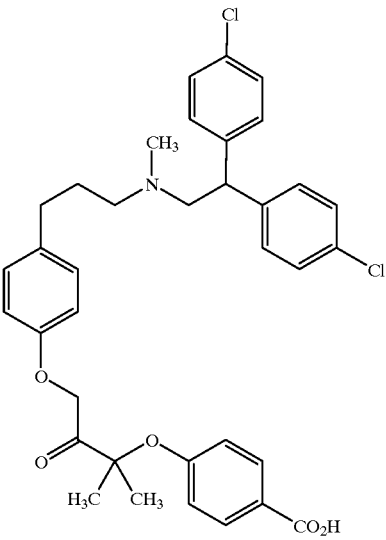 | $C_{36}H_{37}Cl_2NO_5$<br>HRMS (ESI$^-$) calculated for $C_{36}H_{36}O_5N^{35}Cl_2$ [M − H]$^-$: 632.1971,<br>found: 632.1994, δ -3.7 ppm |

TABLE A-continued

| EXAMPLE | STRUCTURE | ANALYSIS |
| --- | --- | --- |
| 24 | 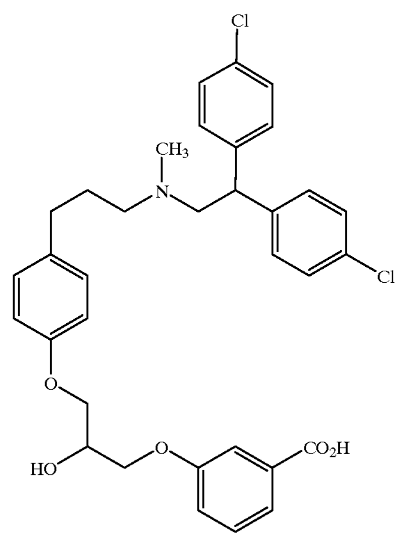 | $C_{34}H_{35}Cl_2NO_5$<br>HRMS (ESI$^+$) calculated for $C_{34}H_{36}NO_5{}^{35}Cl_2$ [M + H]$^+$: 608.19705,<br>found: 608.19705, δ 0.0 ppm |
| 25 | 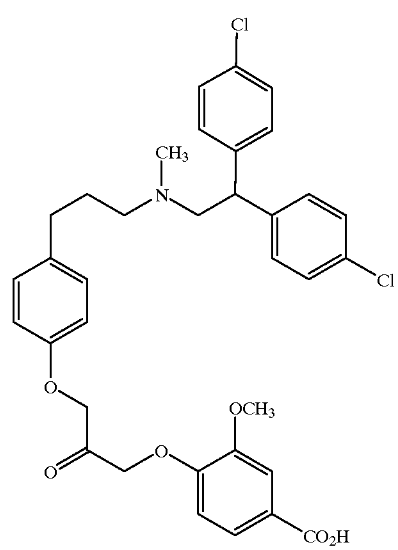 | $C_{35}H_{35}Cl_2NO_6$<br>MS (ESI$^+$) (m/z): 636 [M + H]$^+$ |

TABLE A-continued
| EXAMPLE | STRUCTURE | ANALYSIS |
| --- | --- | --- |
| 26 | 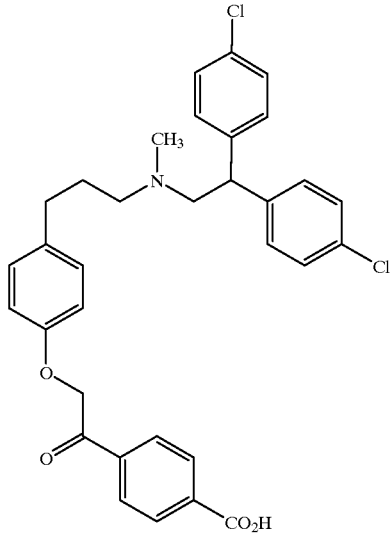 | $C_{33}H_{31}Cl_2NO_4$<br>HRMS (ESI$^-$) calculated for $C_{33}H_{30}O_4N^{35}Cl_2$ [M − H]$^-$: 574.1552,<br>found: 574.1574, δ-3.8 ppm |
| 27 | 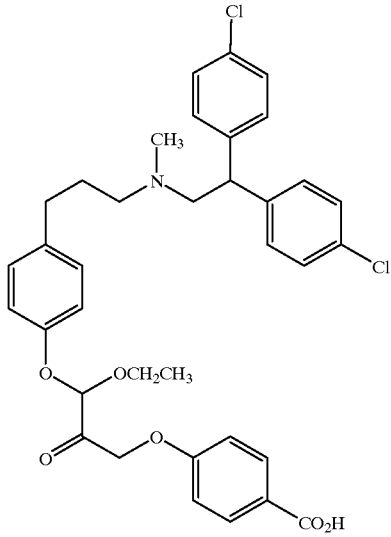 | $C_{36}H_{37}Cl_2NO_6$<br>HRMS (ESI$^+$) calculated for $C_{36}H_{38}{}^{35}Cl_2NO_6$ [M + H]$^+$: 650.207619,<br>found: 650.20832, δ-1.1 ppm |

TABLE A-continued

| EXAMPLE | STRUCTURE | ANALYSIS |
|---|---|---|
| 28 | 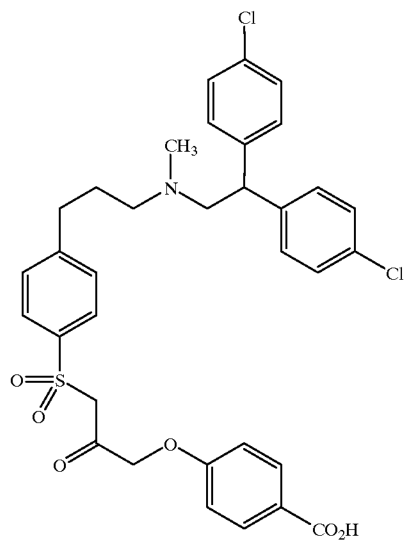 | $C_{34}H_{33}Cl_2NO_6S$<br>HRMS (ESI$^+$) calculated for $C_{34}H_{34}{}^{35}Cl_2NO_6S$ [M + H]$^+$: 654.14838,<br>found: 654.1499, δ-2.3 ppm |
| 29 | 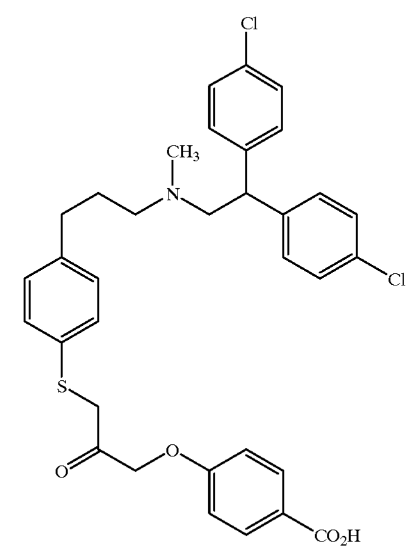 | $C_{34}H_{33}Cl_2NO_4S$<br>MS (ESI$^+$) (m/z): 622 [M + H]$^+$ |

TABLE A-continued
| EXAMPLE | STRUCTURE | ANALYSIS |
| --- | --- | --- |
| 30 | 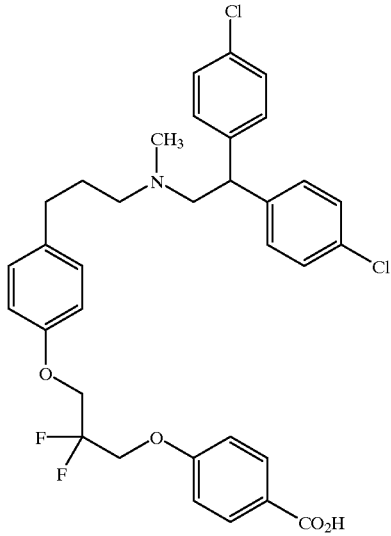 | $C_{34}H_{33}Cl_2F_2NO_4$<br>HRMS (ESI$^+$) calculated for $C_{34}H_{34}{}^{35}Cl_2F_2NO_4$ [M + H]$^+$: 628.18329,<br>found: 628.1839, δ -1.0 ppm |
| 31 | 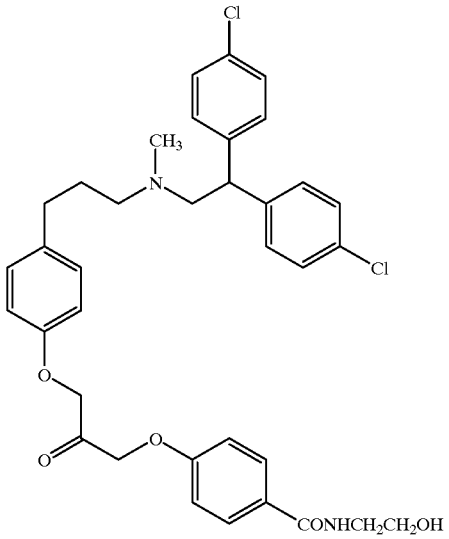 | $C_{36}H_{38}Cl_2N_2O_5$<br>HRMS (ESI$^+$) calculated for $C_{36}H_{39}{}^{35}Cl_2N_2O_5$ [M + H]$^+$: 649.22360,<br>found: 649.22376, δ -0.2 ppm |

TABLE A-continued
| EXAMPLE | STRUCTURE | ANALYSIS |
|---|---|---|
| 32 | 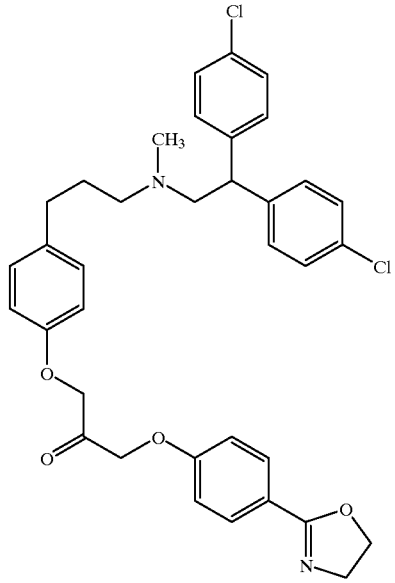 | $C_{36}H_{36}Cl_2N_2O_4$<br>MS (ESI$^+$) (m/z): 631<br>[M + H]$^+$ |
| 33 | 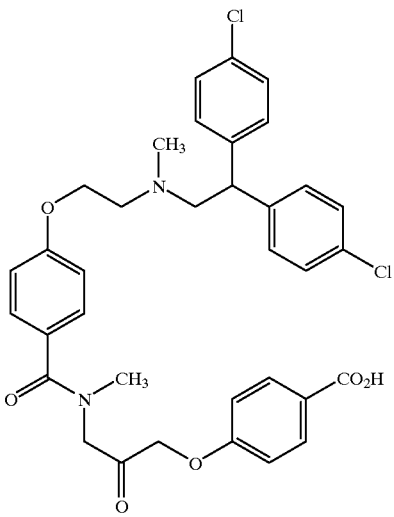 | $C_{35}H_{34}Cl_2N_2O_6$<br>MS (ESI$^+$) (m/z): 649<br>[M + H]$^+$ |

TABLE A-continued

| EXAMPLE | STRUCTURE | ANALYSIS |
| --- | --- | --- |
| 34 | 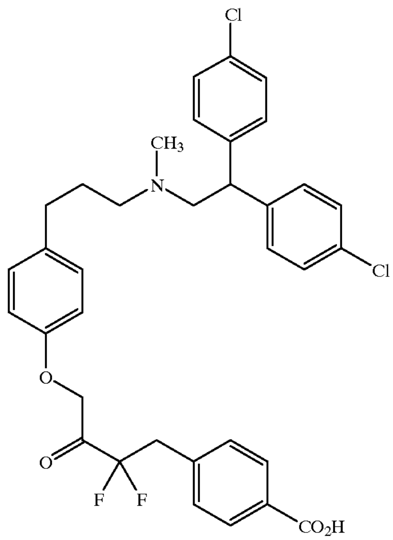 | $C_{35}H_{33}Cl_2F_2NO_4$<br>MS (ESI$^+$) (m/z): 640<br>[M + H]$^+$ |
| 35 | 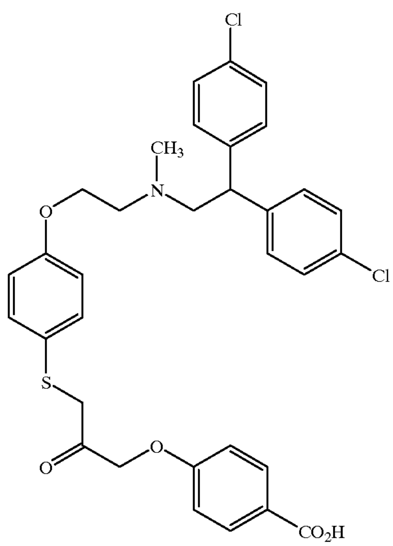 | $C_{33}H_{31}Cl_2NO_5S$<br>MS (ESI$^+$) (m/z): 624<br>[M + H]$^+$ |
| 36 | 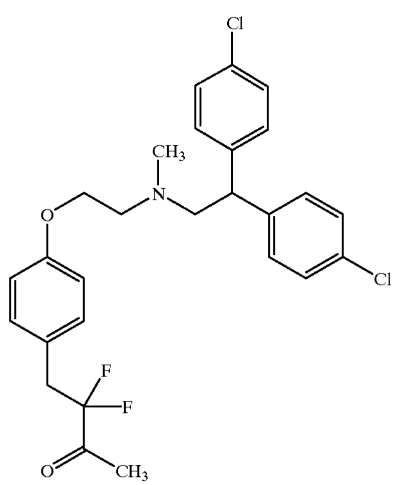 | $C_{26}H_{25}Cl_2F_2NO_2 \cdot HCl \cdot 0.1\ H_2O$<br>Calcd: C 58.85, H 4.98, N 2.64<br>Found: C 58.48, H 5.01, N 2.50 |

TABLE A-continued
| EXAMPLE | STRUCTURE | ANALYSIS |
|---|---|---|
| 37 | 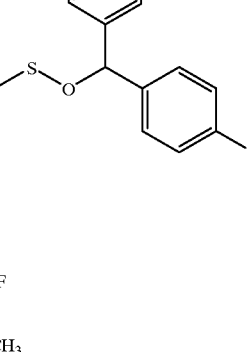 | $C_{27}H_{26}Cl_2F_2O_3S$<br>Calcd: C 60.11, H 4.86<br>Found: C 60.27, H 4.73 |
| 38 | 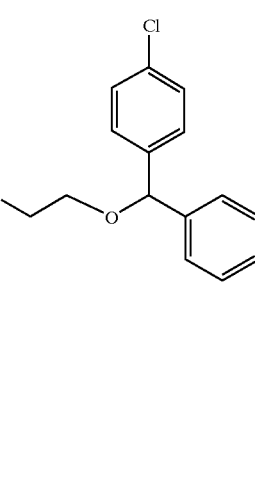 | $C_{27}H_{26}Cl_2F_2O_4S$<br>Calcd: C 58.38, H 4.72<br>Found: C 58.25, H 4.83 |
| 39 | 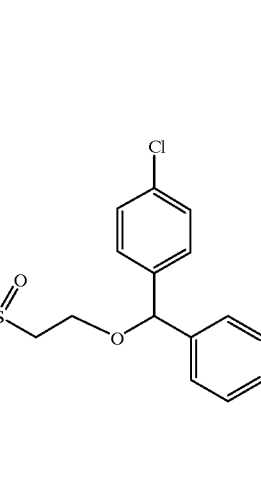 | $C_{27}H_{26}Cl_2F_2O_5S \cdot 0.4\ H_2O$<br>Calcd: C 56.04, H 4.67, N 5.54<br>Found: C 56.01, H 4.57, N 5.02 |

We claim:
1. A compound selected from
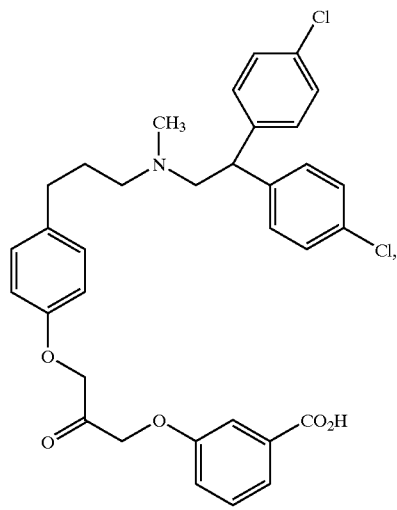
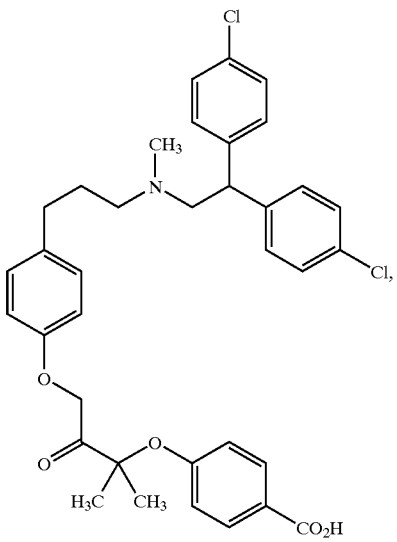
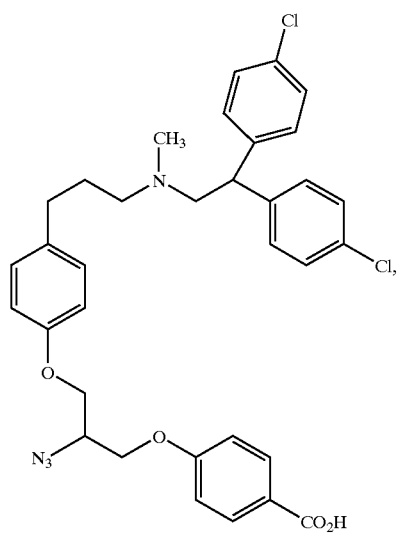
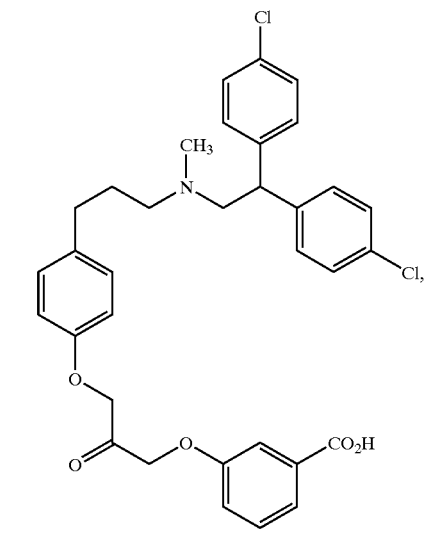
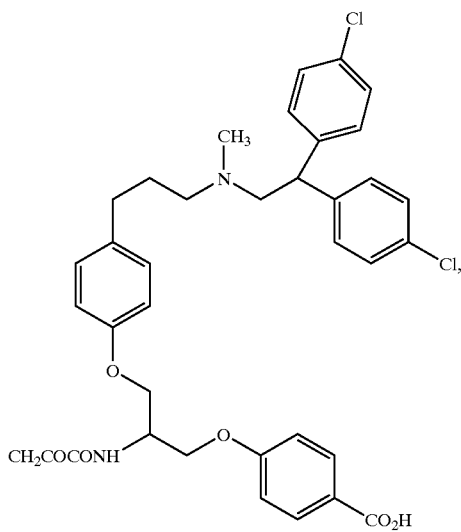
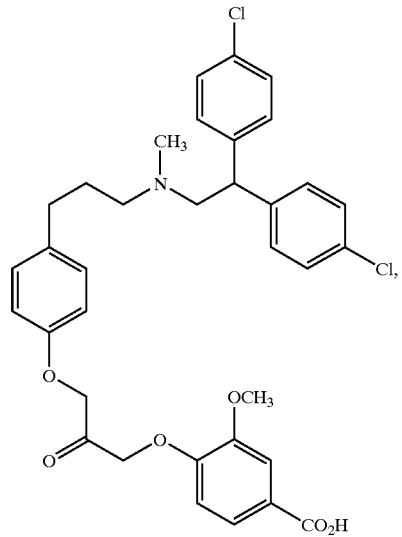

121
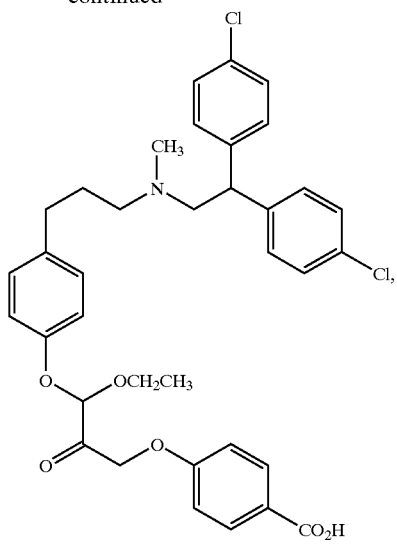
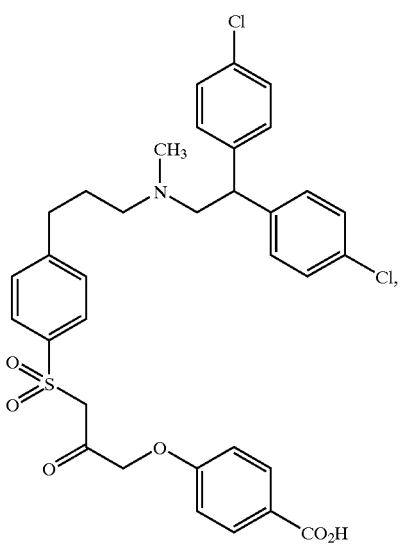
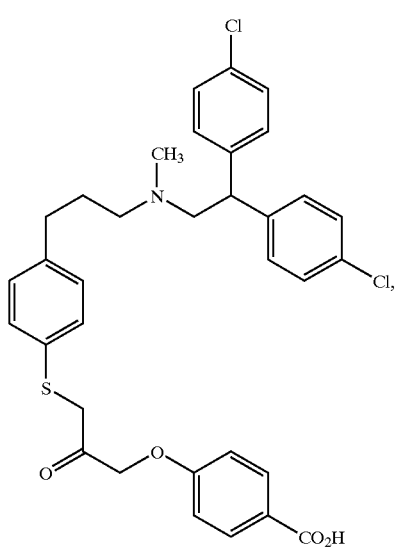
122
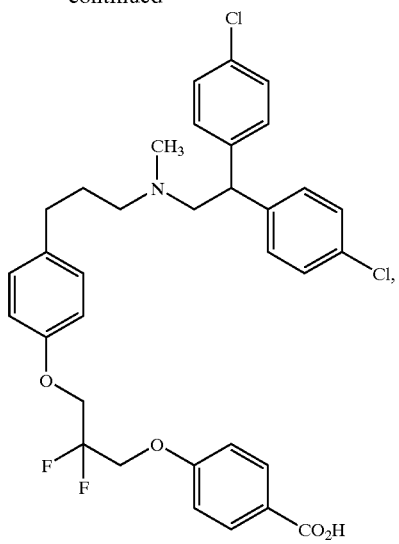
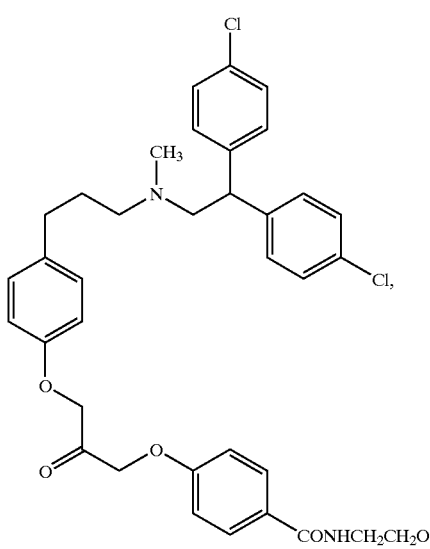
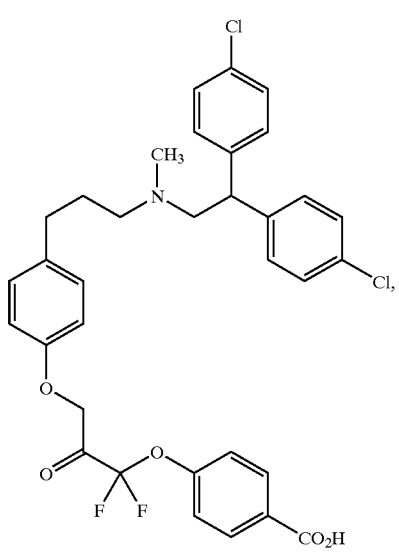

123
-continued
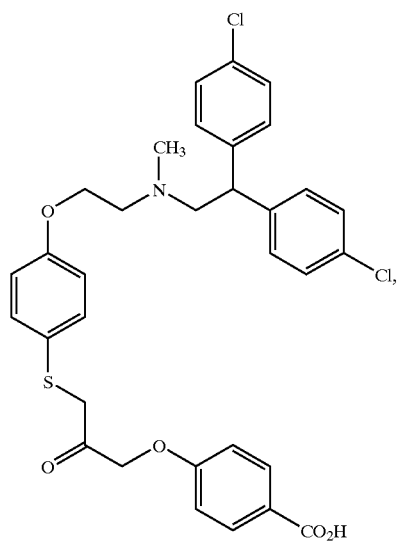
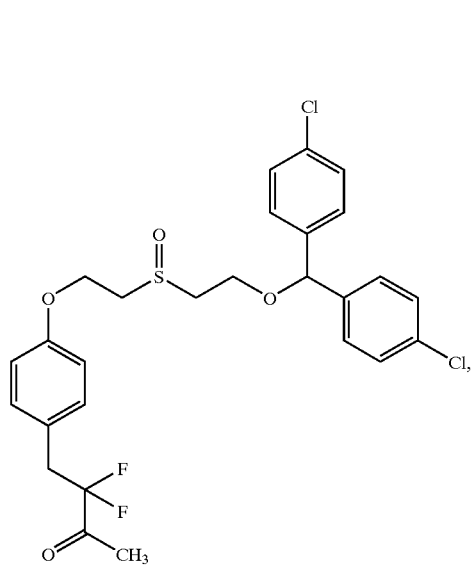
124
-continued
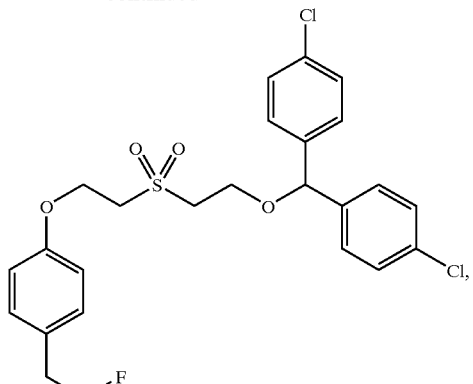
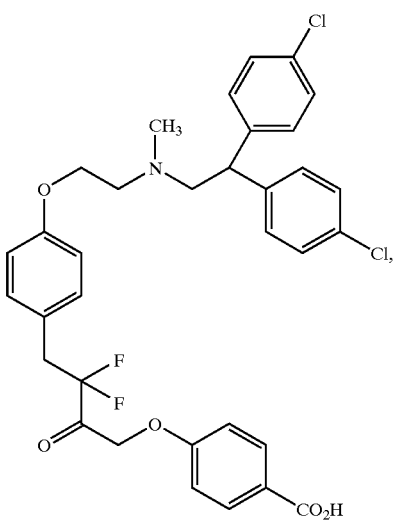
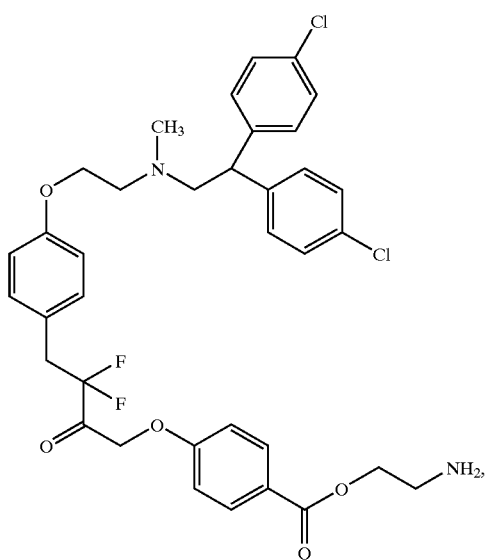

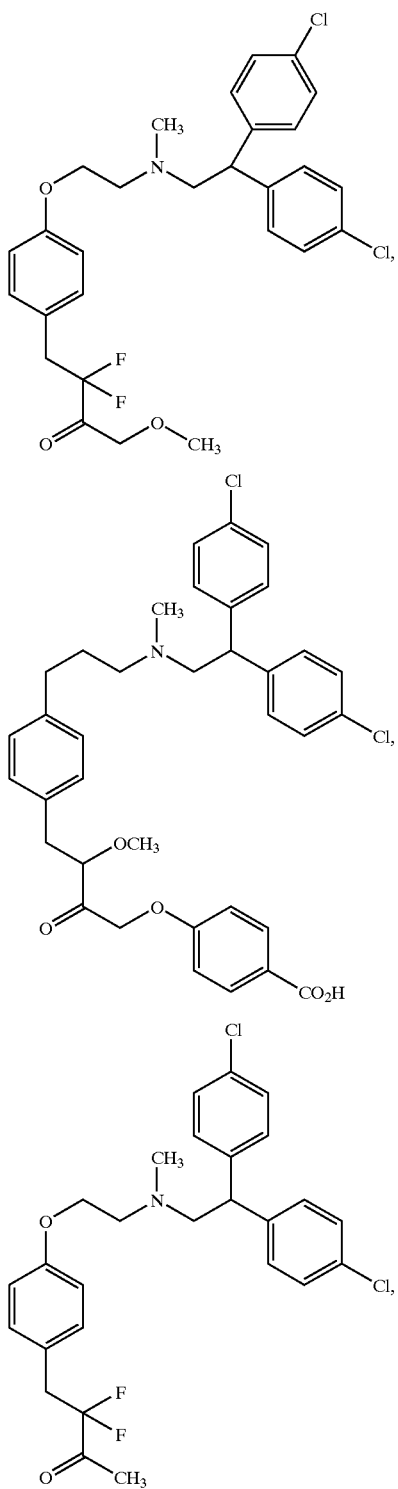
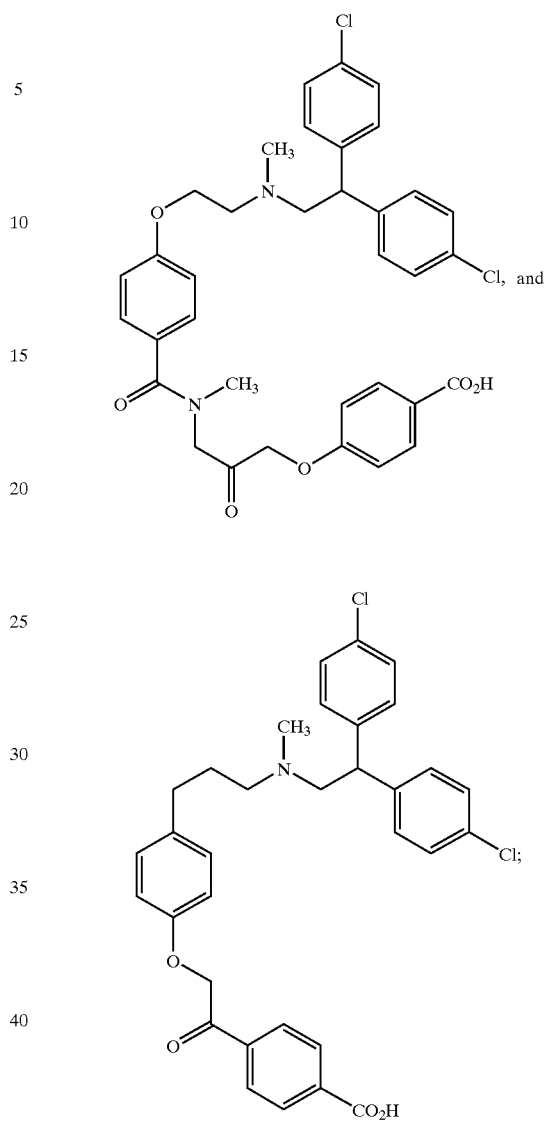
or a pharmaceutically acceptable salt thereof.
2. A pharmaceutical composition for the inhibition of cytosolic phospholipase $A_2$ comprising a therapeutically effective amount of a compound of claim 1 and a pharmaceutically acceptable carrier.
* * * * *

UNITED STATES PATENT AND TRADEMARK OFFICE
CERTIFICATE OF CORRECTION

PATENT NO. : 6,924,391 B2  Page 1 of 3
DATED : August 2, 2005
INVENTOR(S) : Jacques Banville et al.

It is certified that error appears in the above-identified patent and that said Letters Patent is hereby corrected as shown below:

Column 119,
Line 2, after "A compound selected from", add the following:
--
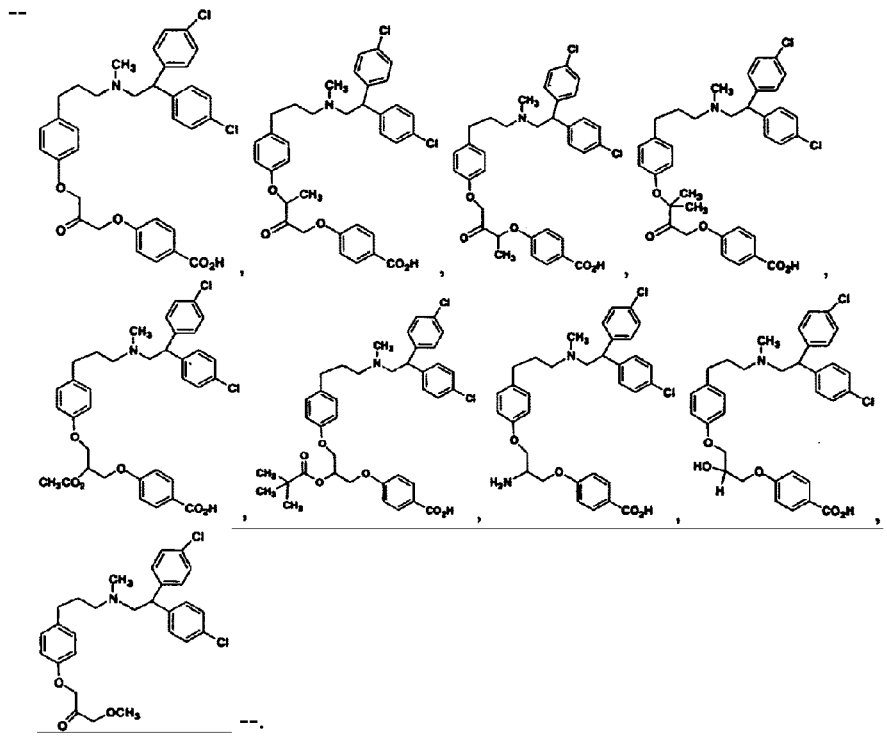

Lines 45-65, the formula should appear as follows:
--  --.
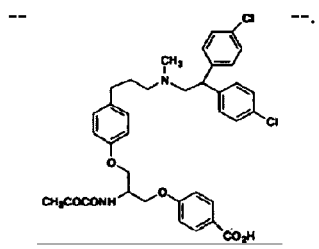

UNITED STATES PATENT AND TRADEMARK OFFICE
CERTIFICATE OF CORRECTION

PATENT NO. : 6,924,391 B2
DATED : August 2, 2005
INVENTOR(S) : Jacques Banville et al.

It is certified that error appears in the above-identified patent and that said Letters Patent is hereby corrected as shown below:

<u>Column 120,</u>
Lines 25-45, the formula should appear as follows:
-- 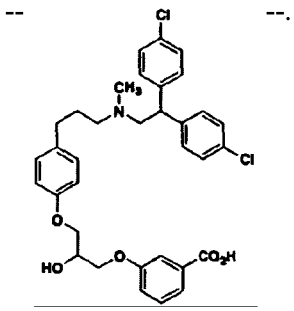 --.

<u>Column 122,</u>
Lines 24-45, the formula should appear as follows:
-- 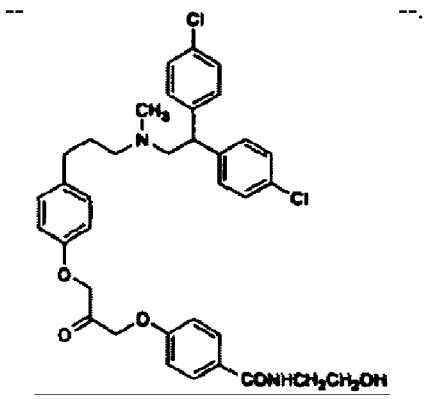 --.

Lines 45-65, the formula should appear as follows:
-- 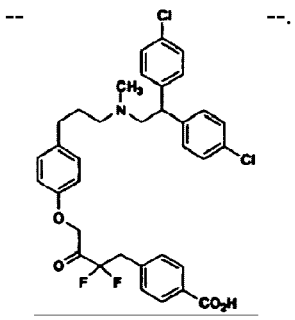 --.

UNITED STATES PATENT AND TRADEMARK OFFICE
CERTIFICATE OF CORRECTION

PATENT NO. : 6,924,391 B2
DATED : August 2, 2005
INVENTOR(S) : Jacques Banville et al.

It is certified that error appears in the above-identified patent and that said Letters Patent is hereby corrected as shown below:

Column 125,
Lines 20-40, the formula should appear as follows:
-- --.

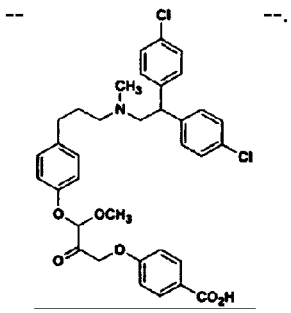

Signed and Sealed this

Sixth Day of June, 2006

JON W. DUDAS
*Director of the United States Patent and Trademark Office*